United States Patent
Tada et al.

(10) Patent No.: US 10,745,684 B2
(45) Date of Patent: Aug. 18, 2020

(54) RECOMBINANT YEAST AND A METHOD FOR PRODUCING ETHANOL USING THE SAME

(71) Applicant: TOYOTA JIDOSHA KABUSHIKI KAISHA, Toyota-shi, Aichi (JP)

(72) Inventors: Nobuki Tada, Nisshin (JP); Toru Onishi, Toyota (JP); Junji Ito, Nisshin (JP); Rie Hirao, Handa (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 16/051,846

(22) Filed: Aug. 1, 2018

(65) Prior Publication Data
US 2019/0040379 A1    Feb. 7, 2019

(30) Foreign Application Priority Data
Aug. 2, 2017  (JP) .................... 2017-150169

(51) Int. Cl.
*C12N 1/16*  (2006.01)
*C12P 7/06*  (2006.01)
(Continued)

(52) U.S. Cl.
CPC ............ *C12N 9/92* (2013.01); *C12N 1/16* (2013.01); *C12N 9/0008* (2013.01); *C12N 9/0036* (2013.01); *C12N 15/52* (2013.01); *C12N 15/81* (2013.01); *C12P 7/06* (2013.01); *C12P 7/08* (2013.01); *C12P 7/10* (2013.01); *C12Y 102/01003* (2013.01); *C12Y 106/99003* (2013.01); *C12Y 202/01006* (2013.01); *C12N 9/1022* (2013.01); *C12N 9/88* (2013.01);
(Continued)

(58) Field of Classification Search
None
See application file for complete search history.

(56) References Cited

U.S. PATENT DOCUMENTS 8,772,012 B2  7/2014  Katahira et al.
8,795,998 B2  8/2014  Pronk et al.
(Continued)

FOREIGN PATENT DOCUMENTS

CN  102712895 A  10/2012
CN  102791858 A  11/2012
(Continued)

OTHER PUBLICATIONS

Eleonora Bellissimi, et al., "Effects of acetic acid on the kinetics of xylose fermentation by an engineered, xylose-isomerase-based *Saccharomyces cerevisiae* strain", FEMS Yeast Res, 2009, pp. 358-364, vol. 9.
(Continued)

*Primary Examiner* — Richard C Ekstrom
(74) *Attorney, Agent, or Firm* — Sughrue Mion, PLLC

(57) ABSTRACT

An acetic acid metabolizing ability of a recombinant yeast strain having xylose-metabolizing ability is to be improved. In such a recombinant yeast strain having xylose-metabolizing ability, the acetaldehyde dehydrogenase gene has been introduced and a gene encoding NADH dehydrogenase involved in reoxidation of cytoplasmic NADH on the mitochondrial outer membrane has been suppressed.

11 Claims, 1 Drawing Sheet
Specification includes a Sequence Listing.

(51) Int. Cl.
| | |
|---|---|
| C12P 7/08 | (2006.01) |
| C12P 7/10 | (2006.01) |
| C12N 9/92 | (2006.01) |
| C12N 15/81 | (2006.01) |
| C12N 9/02 | (2006.01) |
| C12N 15/52 | (2006.01) |
| C12N 9/88 | (2006.01) |
| C12N 9/10 | (2006.01) |

(52) U.S. Cl.
CPC ............ C12Y 202/01001 (2013.01); C12Y 202/01002 (2013.01); C12Y 401/01001 (2013.01); C12Y 501/03001 (2013.01); C12Y 503/01005 (2013.01); C12Y 503/01006 (2013.01)

(56) References Cited

U.S. PATENT DOCUMENTS

| | | | |
|---|---|---|---|
| 2004/0142456 A1* | 7/2004 | Jeffries | C12N 9/0006 435/254.21 |
| 2005/0148055 A1 | 7/2005 | Walther et al. | |
| 2005/0153411 A1* | 7/2005 | Wahlbom | C12N 1/18 435/161 |
| 2010/0255553 A1* | 10/2010 | Srienc | C12N 1/18 435/165 |
| 2011/0027847 A1 | 2/2011 | Matsushika et al. | |
| 2011/0081698 A1 | 4/2011 | Noda et al. | |
| 2011/0137088 A1* | 6/2011 | Borden | C12P 7/065 568/840 |
| 2011/0165660 A1 | 7/2011 | Picataggio et al. | |
| 2012/0093884 A1 | 4/2012 | Vesikari et al. | |
| 2012/0295319 A1* | 11/2012 | Nevoigt | C12N 9/0006 435/161 |
| 2013/0095538 A1 | 4/2013 | Katahira et al. | |
| 2013/0224815 A1* | 8/2013 | Onishi | C12N 15/81 435/161 |
| 2014/0256011 A1* | 9/2014 | Zelle | C12N 15/81 435/161 |
| 2014/0273136 A1* | 9/2014 | Onishi | C12P 7/10 435/162 |
| 2015/0024444 A1 | 1/2015 | Lee et al. | |
| 2015/0087032 A1* | 3/2015 | Park | C12P 7/56 435/116 |
| 2015/0176032 A1* | 6/2015 | De Bont | C12N 1/22 435/161 |
| 2016/0002674 A1 | 1/2016 | Onishi et al. | |
| 2016/0122784 A1* | 5/2016 | Onishi | C12N 9/0006 435/161 |
| 2018/0127763 A1* | 5/2018 | Klaassen | C12N 9/0006 |

FOREIGN PATENT DOCUMENTS

| | | |
|---|---|---|
| JP | 2008-253153 A | 10/2008 |
| JP | 2009-195220 A | 9/2009 |
| JP | 2010-045999 A1 | 3/2010 |
| JP | 2010-239925 A | 10/2010 |
| JP | 2011-24500 A | 2/2011 |
| JP | 2011-147445 A | 8/2011 |
| JP | 2013-500006 A | 1/2013 |
| JP | 2013-540773 A | 11/2013 |
| WO | 03/078643 A1 | 9/2003 |
| WO | 2009-139349 A1 | 11/2009 |
| WO | 2011/010923 A1 | 1/2011 |
| WO | 2011078262 A1 | 6/2011 |
| WO | 2011/140386 A2 | 11/2011 |
| WO | 2012/058603 A1 | 3/2012 |
| WO | 2012067510 A1 | 5/2012 |
| WO | 2013061941 A1 | 5/2013 |
| WO | 2014/004616 A2 | 1/2014 |
| WO | 2014/074895 A2 | 5/2014 |
| WO | 2014/133092 A1 | 9/2014 |

OTHER PUBLICATIONS

Steve Helle, et al., "Effect of inhibitory compounds found in biomass hydrolysates on growth and xylose fermentation by a genetically engineered strain of S. cerevisiae", Enzyme and Microbial Technology, 2003, pp. 786-792, 33.

Alan Gilbert, et al., "Rapid Strain Improvement Through Optimized Evolution in the Cytostat", Biotechnology and Bioengineering, 2009, pp. 500-512, 103.

Jun-Guo Zhang, et al., "Improvement of acetic acid tolerance and fermentation performance of Saccharomyces cerevisiae by disruption of the FPS1 aquaglyceroporin gene", Biotechnol Lett, 2011, pp. 277-284, 33.

Victor Guadalupe Medina, et al., "Elimination of Glycerol Production in Anaerobic Cultures of a Saccharomyces cerevisiae Strain Engineered to Use Acetic Acid as an Electron Acceptor", Applied and Environmental Microbiology, Jan. 2010, pp. 190-195, vol. 76, No. 1.

Brooks M. Henningsen, et al., "Increasing Anaerobic Acetate Consumption and Ethanol Yields in Saccharomyces cerevisiae with NADPH-Specific Alcohol Dehydrogenase", Applied and Environmental Microbiology, Dec. 2015, pp. 8108-8117, vol. 81, No. 23.

Na Wei, et al., "Enhanced biofuel production through coupled acetic acid and xylose consumption by engineered yeast", Nature Communications, Oct. 8, 2013, pp. 1-8, 4:2580.

Liang Zhang, et al., "Improving the ethanol yield by reducing glycerol formation using cofactor regulation in Saccharomyces cerevisiae", Biotechnol Lett, 2011, pp. 1375-1380, vol. 33.

Communication dated Aug. 17, 2016, issued in U.S. Appl. No. 14/767,821.

Communication dated Oct. 27, 2016, issued in U.S. Appl. No. 14/767,821.

Communication dated Mar. 8, 2017, issued in U.S. Appl. No. 14/767,821.

Communication dated Jul. 18, 2017, issued in U.S. Appl. No. 14/767,821.

Communication dated Sep. 15, 2017, issued in U.S. Appl. No. 14/767,821.

Communication dated Jan. 22, 2018, issued in U.S. Appl. No. 14/767,821.

Communication dated May 7, 2018, issued in U.S. Appl. No. 14/767,821.

Communication dated Oct. 19, 2018, issued in U.S. Appl. No. 14/767,821.

Communication dated Jan. 30, 2019, issued in U.S. Appl. No. 14/767,821.

GenBank NCBI Reference Sequence XP_001703585.1, dual function alcohol dehydrogenase/acetaldehyde dehydrogenase [Chlamydomonas reinhardtii], May 2009, retrieved from https://www.ncbi.nlm.nih.gov/protein/XP 001703585.

Communication dated Mar. 4, 2019, issued in U.S. Appl. No. 14/767,821.

Dictionary definition of "assimilate" obtained from dictionary.com on May 2, 2018, 1 page (Year: 2018).

Magneschi et al., "A Mutant in the ADH1 Gene of Chlamydomonas reinhardtii Elicits Metabolic Restructuring during Anaerobiosis", Plant Physiol. 158:1293-1305, 2012.

Gomes et al., Greener J. Biol. Sci. 3:58-60, Jan. 2013 (Year: 2013).

MetaCyc Accession No. G-9110, obtained from http://akongo.psb.ugent.be/META/NEW-IMAGE?type=GENE&object=G-9110, last viewed on Jul. 12, 2017, 6 pages.

Johansson et al., FEMS Yeast Res. 2:277-282, 2002.

GenBank NCBI Reference Sequence WP_000301651.1, bifunctional acetaldehyde-CoA/alcohol dehydrogenase [Proteobacteria].

Communication dated Sep. 14, 2017, from the United States Patent and Trademark Office in counterpart U.S. Appl. No. 14/353,394.

Communication dated Jan. 11, 2018, from the United States Patent and Trademark Office in counterpart U.S. Appl. No. 14/353,394.

Communication dated Apr. 24, 2017, issued by the United States Patent and Trademark Office in U.S. Appl. No. 14/353,394.

Communication, dated Jan. 31, 2017, issued by the United States Patent and Trademark Office in U.S. Appl. No. 14/353,394.

(56) References Cited

OTHER PUBLICATIONS

Oh et al., "Effects of overexpression of acetaldehyde dehydrogenase 6 and acetyl-CoA synthetase 1 on xylitol production in recombinant *Saccharomyces cerevisiae*," Biocatalysis and Agricultural Biotechnology, vol. 1, pp. 11-19, 2012 (available on line Aug. 30, 2011), 2 pages total.

M. Sonderegger et al., "Metabolic Engineering of a Phosphoketolase Pathway for Pentose Catabolism in *Saccharomyces cerevisiae*," Applied and Environmental Microbiology (May 2004), vol. 70, pp. 2892-2897.

Communication dated Sep. 24, 2015, issued in U.S. Appl. No. 14/353,394.

\* cited by examiner

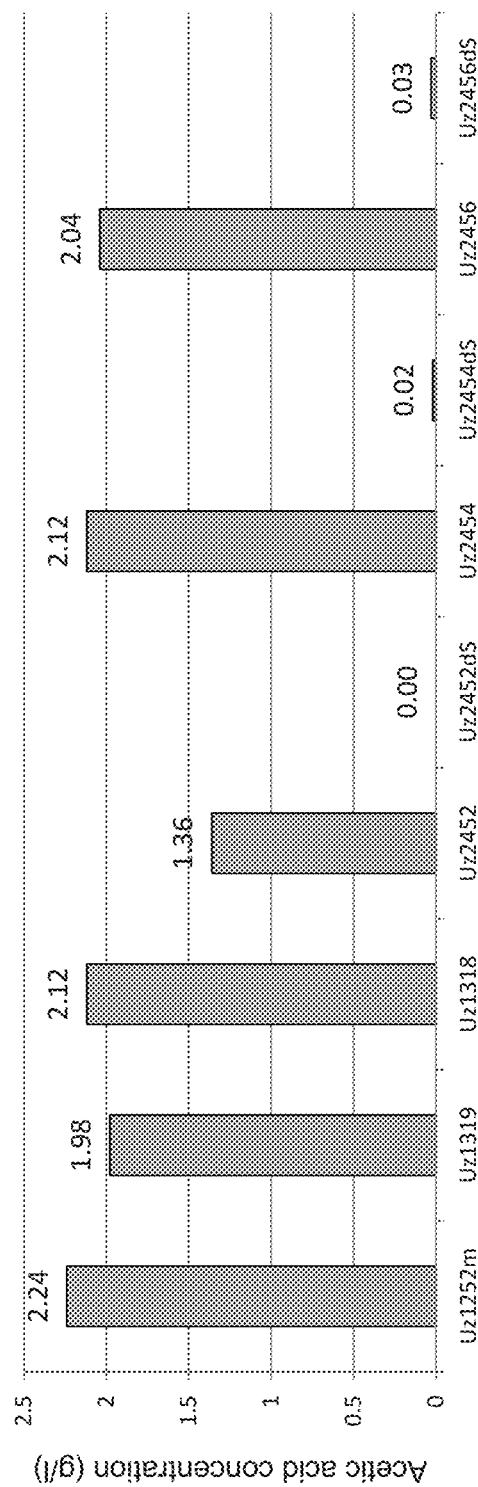

SEQUENCE LISTING

```
<160> NUMBER OF SEQ ID NOS: 102

<210> SEQ ID NO 1
<211> LENGTH: 1683
<212> TYPE: DNA
<213> ORGANISM: Saccharomyces cerevisiae
<220> FEATURE:
<221> NAME/KEY: CDS
<222> LOCATION: (1)..(1683)

<400> SEQUENCE: 1 atg att aga caa tca tta atg aaa aca gtg tgg gct aac tcc tcc agg      48
Met Ile Arg Gln Ser Leu Met Lys Thr Val Trp Ala Asn Ser Ser Arg
1               5                  10                  15 ttt agc cta cag agc aag tcg ggg ctt gtg aaa tat gcc aaa aat aga      96
Phe Ser Leu Gln Ser Lys Ser Gly Leu Val Lys Tyr Ala Lys Asn Arg
            20                  25                  30 tcg ttc cat gca gca aga aat ttg cta gag gac aag aaa gtc att ttg     144
Ser Phe His Ala Ala Arg Asn Leu Leu Glu Asp Lys Lys Val Ile Leu
```

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  | 45 |  |  |  |  |  |

```
caa aaa gtg gcg ccc act act ggc gtt gtt gcg aag cag tcc ttt ttc      192
Gln Lys Val Ala Pro Thr Thr Gly Val Val Ala Lys Gln Ser Phe Phe
    50              55              60 aag aga act ggg aaa ttt act ttg aag gct tta ttg tat tct gcc ctc      240
Lys Arg Thr Gly Lys Phe Thr Leu Lys Ala Leu Leu Tyr Ser Ala Leu
65              70              75              80 gcg ggt acg gct tac gtt tca tac tca ctt tac cga gaa gct aac cct      288
Ala Gly Thr Ala Tyr Val Ser Tyr Ser Leu Tyr Arg Glu Ala Asn Pro
                85              90              95 tct acc caa gtt cct caa tcg gac act ttt cca aac ggt tca aag agg      336
Ser Thr Gln Val Pro Gln Ser Asp Thr Phe Pro Asn Gly Ser Lys Arg
        100             105             110 aag act ttg gta att ctg ggc tcc ggt tgg ggt tct gtg tcg ctt ttg      384
Lys Thr Leu Val Ile Leu Gly Ser Gly Trp Gly Ser Val Ser Leu Leu
115             120             125 aaa aat ttg gac acc acg ttg tat aat gtt gtt gtt gtt tct cca aga      432
Lys Asn Leu Asp Thr Thr Leu Tyr Asn Val Val Val Val Ser Pro Arg
    130             135             140 aat tat ttt ctt ttt act ccg cta ttg cca tct acc cca gtt ggt acc      480
Asn Tyr Phe Leu Phe Thr Pro Leu Leu Pro Ser Thr Pro Val Gly Thr
145             150             155             160 atc gaa ttg aaa tct att gtt gaa cct gtc agg act att gct aga aga      528
Ile Glu Leu Lys Ser Ile Val Glu Pro Val Arg Thr Ile Ala Arg Arg
                165             170             175 tcg cac ggt gaa gtc cat tac tat gaa gct gaa gcg tac gac gtt gat      576
Ser His Gly Glu Val His Tyr Tyr Glu Ala Glu Ala Tyr Asp Val Asp
        180             185             190 cct gaa aac aaa aca att aag gtc aaa tct tcc gct aag aat aac gac      624
Pro Glu Asn Lys Thr Ile Lys Val Lys Ser Ser Ala Lys Asn Asn Asp
195             200             205 tac gac ttg gac ttg aaa tac gac tat ctg gtt gtc ggt gtg ggt gct      672
Tyr Asp Leu Asp Leu Lys Tyr Asp Tyr Leu Val Val Gly Val Gly Ala
    210             215             220 caa cca aac act ttt ggt act ccg gga gtt tat gaa tat tct tct ttc      720
Gln Pro Asn Thr Phe Gly Thr Pro Gly Val Tyr Glu Tyr Ser Ser Phe
225             230             235             240 ttg aag gaa ata tcc gac gct caa gag atc aga tta aaa att atg tcc      768
Leu Lys Glu Ile Ser Asp Ala Gln Glu Ile Arg Leu Lys Ile Met Ser
                245             250             255 agt att gag aaa gct gcc tcc cta tct cca aaa gat cct gag aga gca      816
Ser Ile Glu Lys Ala Ala Ser Leu Ser Pro Lys Asp Pro Glu Arg Ala
        260             265             270 aga ttg ttg agc ttt gtt gtc gtt ggt ggt ggt ccc acc ggt gtc gaa      864
Arg Leu Leu Ser Phe Val Val Val Gly Gly Gly Pro Thr Gly Val Glu
275             280             285 ttt gcc gct gaa ttg aga gat tat gtt gac cag gac ttg aga aaa tgg      912
Phe Ala Ala Glu Leu Arg Asp Tyr Val Asp Gln Asp Leu Arg Lys Trp
    290             295             300 atg ccc gaa ttg agt aaa gaa att aaa gtc act ttg gtg gag gct ttg      960
Met Pro Glu Leu Ser Lys Glu Ile Lys Val Thr Leu Val Glu Ala Leu
305             310             315             320 cca aac att ttg aac atg ttt gac aag tat ctc gtt gac tat gct caa     1008
Pro Asn Ile Leu Asn Met Phe Asp Lys Tyr Leu Val Asp Tyr Ala Gln
                325             330             335 gat tta ttc aaa gag gaa aaa atc gat tta aga ttg aaa aca atg gtt     1056
Asp Leu Phe Lys Glu Glu Lys Ile Asp Leu Arg Leu Lys Thr Met Val
        340             345             350 aag aaa gtt gac gct acc act ata act gcc aaa act ggc gat ggt gac     1104
```

```
Lys Lys Val Asp Ala Thr Thr Ile Thr Ala Lys Thr Gly Asp Gly Asp
            355                 360                 365 att gaa aat ata ccg tat ggt gta tta gtt tgg gct aca ggt aat gcg      1152
Ile Glu Asn Ile Pro Tyr Gly Val Leu Val Trp Ala Thr Gly Asn Ala
        370                 375                 380 cca aga gaa gtg tct aag aac cta atg act aaa tta gag gaa cag gac      1200
Pro Arg Glu Val Ser Lys Asn Leu Met Thr Lys Leu Glu Glu Gln Asp
385                 390                 395                 400 tca aga cgt ggt ttg ttg ata gat aac aaa ctt caa ctt ttg ggt gct      1248
Ser Arg Arg Gly Leu Leu Ile Asp Asn Lys Leu Gln Leu Leu Gly Ala
                405                 410                 415 aag gga tct att ttt gct atc ggc gat tgt acc ttc cac cct ggc ttg      1296
Lys Gly Ser Ile Phe Ala Ile Gly Asp Cys Thr Phe His Pro Gly Leu
            420                 425                 430 ttc cct acc gct caa gtt gcc cac caa gaa ggt gaa tac ttg gct cag      1344
Phe Pro Thr Ala Gln Val Ala His Gln Glu Gly Glu Tyr Leu Ala Gln
        435                 440                 445 tat ttc aag aaa gct tat aaa atc gat caa ttg aac tgg aaa atg acc      1392
Tyr Phe Lys Lys Ala Tyr Lys Ile Asp Gln Leu Asn Trp Lys Met Thr
450                 455                 460 cat gct aaa gac gat tca gaa gtc gct aga tta aag aac caa ata gtc      1440
His Ala Lys Asp Asp Ser Glu Val Ala Arg Leu Lys Asn Gln Ile Val
465                 470                 475                 480 aaa acg caa tcg caa att gaa gac ttc aag tac aac cat aag ggt gct      1488
Lys Thr Gln Ser Gln Ile Glu Asp Phe Lys Tyr Asn His Lys Gly Ala
                485                 490                 495 ctg gct tat att ggt tca gat aaa gcc att gct gat ctt gcc gtt ggt      1536
Leu Ala Tyr Ile Gly Ser Asp Lys Ala Ile Ala Asp Leu Ala Val Gly
            500                 505                 510 gaa gcc aaa tat agg tta gcc ggc tca ttc acc ttc cta ttc tgg aaa      1584
Glu Ala Lys Tyr Arg Leu Ala Gly Ser Phe Thr Phe Leu Phe Trp Lys
        515                 520                 525 tct gct tat ttg gca atg tgt cta tcc ttt aga aac aga gtt ctt gtc      1632
Ser Ala Tyr Leu Ala Met Cys Leu Ser Phe Arg Asn Arg Val Leu Val
530                 535                 540 gct atg gat tgg gct aaa gtt tat ttc ttg ggt aga gat tca tct atc      1680
Ala Met Asp Trp Ala Lys Val Tyr Phe Leu Gly Arg Asp Ser Ser Ile
545                 550                 555                 560 tag                                                                  1683

<210> SEQ ID NO 2
<211> LENGTH: 560
<212> TYPE: PRT
<213> ORGANISM: Saccharomyces cerevisiae

<400> SEQUENCE: 2

Met Ile Arg Gln Ser Leu Met Lys Thr Val Trp Ala Asn Ser Ser Arg
1               5                   10                  15

Phe Ser Leu Gln Ser Lys Ser Gly Leu Val Lys Tyr Ala Lys Asn Arg
            20                  25                  30

Ser Phe His Ala Ala Arg Asn Leu Glu Asp Lys Lys Val Ile Leu
        35                  40                  45

Gln Lys Val Ala Pro Thr Thr Gly Val Val Ala Lys Gln Ser Phe Phe
    50                  55                  60

Lys Arg Thr Gly Lys Phe Thr Leu Lys Ala Leu Leu Tyr Ser Ala Leu
65                  70                  75                  80

Ala Gly Thr Ala Tyr Val Ser Tyr Ser Leu Tyr Arg Glu Ala Asn Pro
                85                  90                  95
```

-continued

```
Ser Thr Gln Val Pro Gln Ser Asp Thr Phe Pro Asn Gly Ser Lys Arg
                100                 105                 110
Lys Thr Leu Val Ile Leu Gly Ser Gly Trp Gly Ser Val Ser Leu Leu
            115                 120                 125
Lys Asn Leu Asp Thr Thr Leu Tyr Asn Val Val Val Ser Pro Arg
130                 135                 140
Asn Tyr Phe Leu Phe Thr Pro Leu Leu Pro Ser Thr Pro Val Gly Thr
145                 150                 155                 160
Ile Glu Leu Lys Ser Ile Val Glu Pro Val Arg Thr Ile Ala Arg Arg
                165                 170                 175
Ser His Gly Glu Val His Tyr Tyr Glu Ala Glu Ala Tyr Asp Val Asp
            180                 185                 190
Pro Glu Asn Lys Thr Ile Lys Val Lys Ser Ser Ala Lys Asn Asn Asp
        195                 200                 205
Tyr Asp Leu Asp Leu Lys Tyr Asp Tyr Leu Val Val Gly Val Gly Ala
210                 215                 220
Gln Pro Asn Thr Phe Gly Thr Pro Gly Val Tyr Glu Tyr Ser Ser Phe
225                 230                 235                 240
Leu Lys Glu Ile Ser Asp Ala Gln Glu Ile Arg Leu Lys Ile Met Ser
                245                 250                 255
Ser Ile Glu Lys Ala Ala Ser Leu Ser Pro Lys Asp Pro Glu Arg Ala
            260                 265                 270
Arg Leu Leu Ser Phe Val Val Gly Gly Pro Thr Gly Val Glu
        275                 280                 285
Phe Ala Ala Glu Leu Arg Asp Tyr Val Asp Gln Asp Leu Arg Lys Trp
290                 295                 300
Met Pro Glu Leu Ser Lys Glu Ile Lys Val Thr Leu Val Glu Ala Leu
305                 310                 315                 320
Pro Asn Ile Leu Asn Met Phe Asp Lys Tyr Leu Val Asp Tyr Ala Gln
                325                 330                 335
Asp Leu Phe Lys Glu Glu Lys Ile Asp Leu Arg Leu Lys Thr Met Val
            340                 345                 350
Lys Lys Val Asp Ala Thr Thr Ile Thr Ala Lys Thr Gly Asp Gly Asp
        355                 360                 365
Ile Glu Asn Ile Pro Tyr Gly Val Leu Val Trp Ala Thr Gly Asn Ala
370                 375                 380
Pro Arg Glu Val Ser Lys Asn Leu Met Thr Lys Leu Glu Glu Gln Asp
385                 390                 395                 400
Ser Arg Arg Gly Leu Leu Ile Asp Asn Lys Leu Gln Leu Leu Gly Ala
                405                 410                 415
Lys Gly Ser Ile Phe Ala Ile Gly Asp Cys Thr Phe His Pro Gly Leu
            420                 425                 430
Phe Pro Thr Ala Gln Val Ala His Gln Glu Gly Glu Tyr Leu Ala Gln
        435                 440                 445
Tyr Phe Lys Lys Ala Tyr Lys Ile Asp Gln Leu Asn Trp Lys Met Thr
450                 455                 460
His Ala Lys Asp Asp Ser Glu Val Ala Arg Leu Lys Asn Gln Ile Val
465                 470                 475                 480
Lys Thr Gln Ser Gln Ile Glu Asp Phe Lys Tyr Asn His Lys Gly Ala
                485                 490                 495
Leu Ala Tyr Ile Gly Ser Asp Lys Ala Ile Ala Asp Leu Ala Val Gly
            500                 505                 510
Glu Ala Lys Tyr Arg Leu Ala Gly Ser Phe Thr Phe Leu Phe Trp Lys
```

```
                515                 520                 525
Ser Ala Tyr Leu Ala Met Cys Leu Ser Phe Arg Asn Arg Val Leu Val
    530                 535                 540

Ala Met Asp Trp Ala Lys Val Tyr Phe Leu Gly Arg Asp Ser Ser Ile
545                 550                 555                 560

<210> SEQ ID NO 3
<211> LENGTH: 1638
<212> TYPE: DNA
<213> ORGANISM: Saccharomyces cerevisiae
<220> FEATURE:
<221> NAME/KEY: CDS
<222> LOCATION: (1)..(1638)

<400> SEQUENCE: 3 atg ctg ccc aga ctt ggt ttt gcg agg act gct agg tcc ata cac cgt      48
Met Leu Pro Arg Leu Gly Phe Ala Arg Thr Ala Arg Ser Ile His Arg
1               5                  10                  15 ttc aag atg acc cag atc tct aaa cct ttt ttc cat tcc act gaa gtt      96
Phe Lys Met Thr Gln Ile Ser Lys Pro Phe Phe His Ser Thr Glu Val
                20                  25                  30 ggt aag ccc gga cca cag cag aag cta tcg aaa tct tac act gcg gta     144
Gly Lys Pro Gly Pro Gln Gln Lys Leu Ser Lys Ser Tyr Thr Ala Val
            35                  40                  45 ttc aag aaa tgg ttt gtc aga ggt tta aag tta acc ttt tac acg acg     192
Phe Lys Lys Trp Phe Val Arg Gly Leu Lys Leu Thr Phe Tyr Thr Thr
        50                  55                  60 ttg gcc ggc aca ttg tat gtg tca tac gag ctg tac aaa gaa tcg aac     240
Leu Ala Gly Thr Leu Tyr Val Ser Tyr Glu Leu Tyr Lys Glu Ser Asn
65                  70                  75                  80 cca ccc aaa cag gtt ccc caa tcg acc gct ttt gct aat ggt ttg aaa     288
Pro Pro Lys Gln Val Pro Gln Ser Thr Ala Phe Ala Asn Gly Leu Lys
                85                  90                  95 aag aag gag ctg gtt att ttg ggt aca ggc tgg ggc gcc ata tct ctt     336
Lys Lys Glu Leu Val Ile Leu Gly Thr Gly Trp Gly Ala Ile Ser Leu
            100                 105                 110 ttg aag aaa tta gac acg tct ttg tat aac gtg acc gtg gtg tcg cca     384
Leu Lys Lys Leu Asp Thr Ser Leu Tyr Asn Val Thr Val Val Ser Pro
        115                 120                 125 aga agc ttc ttt ttg ttc aca ccg tta tta ccc tca acg cct gtg ggt     432
Arg Ser Phe Phe Leu Phe Thr Pro Leu Leu Pro Ser Thr Pro Val Gly
130                 135                 140 acg ata gag atg aag tct att gtc gaa ccg gtt aga tcg atc gct aga     480
Thr Ile Glu Met Lys Ser Ile Val Glu Pro Val Arg Ser Ile Ala Arg
145                 150                 155                 160 aga acg cct gga gaa gtt cac tac att gag gcg gaa gcg ttg gac gtt     528
Arg Thr Pro Gly Glu Val His Tyr Ile Glu Ala Glu Ala Leu Asp Val
                165                 170                 175 gat cca aag gcc aaa aaa gta atg gtg caa tcg gtg tca gag gac gaa     576
Asp Pro Lys Ala Lys Lys Val Met Val Gln Ser Val Ser Glu Asp Glu
            180                 185                 190 tat ttc gtt tcg agc tta agt tac gat tat ctt gtt gtt agt gta ggc     624
Tyr Phe Val Ser Ser Leu Ser Tyr Asp Tyr Leu Val Val Ser Val Gly
        195                 200                 205 gct aaa acc act act ttt aac att ccc ggg gtc tat ggc aat gct aac     672
Ala Lys Thr Thr Thr Phe Asn Ile Pro Gly Val Tyr Gly Asn Ala Asn
    210                 215                 220 ttc ttg aaa gag att gaa gat gct caa aat att cgt atg aag tta atg     720
Phe Leu Lys Glu Ile Glu Asp Ala Gln Asn Ile Arg Met Lys Leu Met
225                 230                 235                 240
```

```
aaa acc ata gaa cag gca agt tca ttt cct gtg aac gat ccg gaa agg      768
Lys Thr Ile Glu Gln Ala Ser Ser Phe Pro Val Asn Asp Pro Glu Arg
            245                 250                 255 aag cga tta tta acg ttc gtg gtt gtt gga ggg ggc cct acg ggg gtt      816
Lys Arg Leu Leu Thr Phe Val Val Val Gly Gly Gly Pro Thr Gly Val
        260                 265                 270 gaa ttt gcc gcc gaa ctg caa gat tac atc aat caa gat ttg agg aag      864
Glu Phe Ala Ala Glu Leu Gln Asp Tyr Ile Asn Gln Asp Leu Arg Lys
    275                 280                 285 tgg atg ccc gac tta agt aaa gaa atg aag gtt atc tta att gaa gcc      912
Trp Met Pro Asp Leu Ser Lys Glu Met Lys Val Ile Leu Ile Glu Ala
290                 295                 300 ctg cct aat atc cta aac atg ttc gat aag acg ttg atc aag tat gcc      960
Leu Pro Asn Ile Leu Asn Met Phe Asp Lys Thr Leu Ile Lys Tyr Ala
305                 310                 315                 320 gag gac ctt ttt gcc aga gat gaa att gac ttg caa gtg aat act gcc     1008
Glu Asp Leu Phe Ala Arg Asp Glu Ile Asp Leu Gln Val Asn Thr Ala
            325                 330                 335 gtg aaa gtc gta gag cca acc tat ata cgc act ctg caa aac ggc caa     1056
Val Lys Val Val Glu Pro Thr Tyr Ile Arg Thr Leu Gln Asn Gly Gln
        340                 345                 350 aca aac acg gat atc gaa tac ggg atg ctg gtt tgg gcc acg gga aat     1104
Thr Asn Thr Asp Ile Glu Tyr Gly Met Leu Val Trp Ala Thr Gly Asn
    355                 360                 365 gaa cca atc gat ttt tca aag aca ctg atg agt aga ata ccg gag caa     1152
Glu Pro Ile Asp Phe Ser Lys Thr Leu Met Ser Arg Ile Pro Glu Gln
370                 375                 380 act aat agg cgt ggt ctg tta att aat gac aag ttg gag ctt ctc ggt     1200
Thr Asn Arg Arg Gly Leu Leu Ile Asn Asp Lys Leu Glu Leu Leu Gly
385                 390                 395                 400 tct gag aat tcg att tat gca att ggt gat tgt acc gca cac acg ggt     1248
Ser Glu Asn Ser Ile Tyr Ala Ile Gly Asp Cys Thr Ala His Thr Gly
            405                 410                 415 ttc ttt ccc acg gca caa gtt gca cat cag gaa ggc gaa tac ttg gcc     1296
Phe Phe Pro Thr Ala Gln Val Ala His Gln Glu Gly Glu Tyr Leu Ala
        420                 425                 430 aag atc ttg gat aaa aaa tta cag ata gaa caa ttg gaa tgg gac atg     1344
Lys Ile Leu Asp Lys Lys Leu Gln Ile Glu Gln Leu Glu Trp Asp Met
    435                 440                 445 ctc aac agt acc gat gaa act gag gta tca cgt cta caa aaa gag gtt     1392
Leu Asn Ser Thr Asp Glu Thr Glu Val Ser Arg Leu Gln Lys Glu Val
450                 455                 460 aat ttg agg aaa tct aag ttg gat aag ttc aac tac aag cat atg ggt     1440
Asn Leu Arg Lys Ser Lys Leu Asp Lys Phe Asn Tyr Lys His Met Gly
465                 470                 475                 480 gcc ctt gcg tac atc ggc tct gaa acc gca att gca gat ttg cat atg     1488
Ala Leu Ala Tyr Ile Gly Ser Glu Thr Ala Ile Ala Asp Leu His Met
            485                 490                 495 ggc gac tca tca tac cag ttg aaa ggt atg ttt gcc ttc ttg ttt tgg     1536
Gly Asp Ser Ser Tyr Gln Leu Lys Gly Met Phe Ala Phe Leu Phe Trp
        500                 505                 510 aaa tcc gct tat ttg gcc atg tgt ctc tct atc agg aat agg att tta     1584
Lys Ser Ala Tyr Leu Ala Met Cys Leu Ser Ile Arg Asn Arg Ile Leu
    515                 520                 525 att gcc atg gac tgg acc aaa gtt tac ttt ctt gga agg gat tcc tcc     1632
Ile Ala Met Asp Trp Thr Lys Val Tyr Phe Leu Gly Arg Asp Ser Ser
530                 535                 540 gtg tag                                                              1638
Val
545
```

<210> SEQ ID NO 4
<211> LENGTH: 545
<212> TYPE: PRT
<213> ORGANISM: Saccharomyces cerevisiae

<400> SEQUENCE: 4

Met Leu Pro Arg Leu Gly Phe Ala Arg Thr Ala Arg Ser Ile His Arg
1               5                   10                  15

Phe Lys Met Thr Gln Ile Ser Lys Pro Phe His Ser Thr Glu Val
            20                  25                  30

Gly Lys Pro Gly Pro Gln Gln Lys Leu Ser Lys Ser Tyr Thr Ala Val
        35                  40                  45

Phe Lys Lys Trp Phe Val Arg Gly Leu Lys Leu Thr Phe Tyr Thr Thr
50                  55                  60

Leu Ala Gly Thr Leu Tyr Val Ser Tyr Glu Leu Tyr Lys Glu Ser Asn
65                  70                  75                  80

Pro Pro Lys Gln Val Pro Gln Ser Thr Ala Phe Ala Asn Gly Leu Lys
                85                  90                  95

Lys Lys Glu Leu Val Ile Leu Gly Thr Gly Trp Gly Ala Ile Ser Leu
            100                 105                 110

Leu Lys Lys Leu Asp Thr Ser Leu Tyr Asn Val Thr Val Val Ser Pro
        115                 120                 125

Arg Ser Phe Phe Leu Phe Thr Pro Leu Leu Pro Ser Thr Pro Val Gly
    130                 135                 140

Thr Ile Glu Met Lys Ser Ile Val Glu Pro Val Arg Ser Ile Ala Arg
145                 150                 155                 160

Arg Thr Pro Gly Glu Val His Tyr Ile Glu Ala Glu Ala Leu Asp Val
                165                 170                 175

Asp Pro Lys Ala Lys Lys Val Met Val Gln Ser Val Ser Glu Asp Glu
            180                 185                 190

Tyr Phe Val Ser Ser Leu Ser Tyr Asp Tyr Leu Val Val Ser Val Gly
        195                 200                 205

Ala Lys Thr Thr Thr Phe Asn Ile Pro Gly Val Tyr Gly Asn Ala Asn
    210                 215                 220

Phe Leu Lys Glu Ile Glu Asp Ala Gln Asn Ile Arg Met Lys Leu Met
225                 230                 235                 240

Lys Thr Ile Glu Gln Ala Ser Ser Phe Pro Val Asn Asp Pro Glu Arg
                245                 250                 255

Lys Arg Leu Leu Thr Phe Val Val Val Gly Gly Gly Pro Thr Gly Val
            260                 265                 270

Glu Phe Ala Ala Glu Leu Gln Asp Tyr Ile Asn Gln Asp Leu Arg Lys
        275                 280                 285

Trp Met Pro Asp Leu Ser Lys Glu Met Lys Val Ile Leu Ile Glu Ala
    290                 295                 300

Leu Pro Asn Ile Leu Asn Met Phe Asp Lys Thr Leu Ile Lys Tyr Ala
305                 310                 315                 320

Glu Asp Leu Phe Ala Arg Asp Glu Ile Asp Leu Gln Val Asn Thr Ala
                325                 330                 335

Val Lys Val Val Glu Pro Thr Tyr Ile Arg Thr Leu Gln Asn Gly Gln
            340                 345                 350

Thr Asn Thr Asp Ile Glu Tyr Gly Met Leu Val Trp Ala Thr Gly Asn
        355                 360                 365

Glu Pro Ile Asp Phe Ser Lys Thr Leu Met Ser Arg Ile Pro Glu Gln

```
                370               375               380
Thr Asn Arg Arg Gly Leu Leu Ile Asn Asp Lys Leu Glu Leu Leu Gly
385                 390                 395                 400

Ser Glu Asn Ser Ile Tyr Ala Ile Gly Asp Cys Thr Ala His Thr Gly
                405                 410                 415

Phe Phe Pro Thr Ala Gln Val Ala His Gln Glu Gly Glu Tyr Leu Ala
            420                 425                 430

Lys Ile Leu Asp Lys Lys Leu Gln Ile Glu Gln Leu Gly Trp Asp Met
        435                 440                 445

Leu Asn Ser Thr Asp Glu Thr Glu Val Ser Arg Leu Gln Lys Glu Val
    450                 455                 460

Asn Leu Arg Lys Ser Lys Leu Asp Lys Phe Asn Tyr Lys His Met Gly
465                 470                 475                 480

Ala Leu Ala Tyr Ile Gly Ser Glu Thr Ala Ile Ala Asp Leu His Met
                485                 490                 495

Gly Asp Ser Ser Tyr Gln Leu Lys Gly Met Phe Ala Phe Leu Phe Trp
            500                 505                 510

Lys Ser Ala Tyr Leu Ala Met Cys Leu Ser Ile Arg Asn Arg Ile Leu
        515                 520                 525

Ile Ala Met Asp Trp Thr Lys Val Tyr Phe Leu Gly Arg Asp Ser Ser
    530                 535                 540

Val
545

<210> SEQ ID NO 5
<211> LENGTH: 1320
<212> TYPE: DNA
<213> ORGANISM: Unknown
<220> FEATURE:
<223> OTHER INFORMATION: Obtained from Intestinal Protist of
      Reticulitermes speratus
<220> FEATURE:
<221> NAME/KEY: CDS
<222> LOCATION: (1)..(1320)

<400> SEQUENCE: 5 atg tct caa att ttt aag gat atc cca gtt att aaa tat gaa ggt cca         48
Met Ser Gln Ile Phe Lys Asp Ile Pro Val Ile Lys Tyr Glu Gly Pro
1               5                   10                  15 gct tcc aag aat cct ttg agt ttc aaa tac tac gat gca aac aag gtt         96
Ala Ser Lys Asn Pro Leu Ser Phe Lys Tyr Tyr Asp Ala Asn Lys Val
                20                  25                  30 att gat ggt aaa cca atg aag gaa cat ttg aga tac gca atg gct tgg        144
Ile Asp Gly Lys Pro Met Lys Glu His Leu Arg Tyr Ala Met Ala Trp
            35                  40                  45 tgg cat aat ttg tgt gct acc ggt caa gat atg ttt ggt cct ggt act        192
Trp His Asn Leu Cys Ala Thr Gly Gln Asp Met Phe Gly Pro Gly Thr
        50                  55                  60 gca gat aaa tcc ttc ggt agt aag aca gtt ggt acc atg gaa cat gca        240
Ala Asp Lys Ser Phe Gly Ser Lys Thr Val Gly Thr Met Glu His Ala
65                  70                  75                  80 cat gct aaa gtt gat gct ggt ttt gaa ttc atg tcc aag ttg ggt gtt        288
His Ala Lys Val Asp Ala Gly Phe Glu Phe Met Ser Lys Leu Gly Val
                85                  90                  95 gaa tac ttc tgt ttc cat gat gct gat ttg gtt cca gaa gca gat act        336
Glu Tyr Phe Cys Phe His Asp Ala Asp Leu Val Pro Glu Ala Asp Thr
                100                 105                 110 ttg agt gaa aca aac aaa aga ttg gat gaa atc gct gaa cat atc gtt        384
Leu Ser Glu Thr Asn Lys Arg Leu Asp Glu Ile Ala Glu His Ile Val
```

```
           115                 120                 125
gct aag caa aag gca act ggt att aaa tgt ttg tgg ggt aca gca aat    432
Ala Lys Gln Lys Ala Thr Gly Ile Lys Cys Leu Trp Gly Thr Ala Asn
    130                 135                 140 ttg ttt tct aac cct aga ttc tta aat ggt tct ggt tct tca aac tca    480
Leu Phe Ser Asn Pro Arg Phe Leu Asn Gly Ser Gly Ser Ser Asn Ser
145                 150                 155                 160 gct gat gtt tat gca tac gct gca gct caa att aaa aag gct ttg gat    528
Ala Asp Val Tyr Ala Tyr Ala Ala Ala Gln Ile Lys Lys Ala Leu Asp
            165                 170                 175 ttg act gtt aaa ttt ggt ggt gtt ggt tat gtt ttc tgg ggt ggt aga    576
Leu Thr Val Lys Phe Gly Gly Val Gly Tyr Val Phe Trp Gly Gly Arg
        180                 185                 190 gaa ggt tac gaa acc ttg ttg aac act gat gtt aag ttc gaa caa gaa    624
Glu Gly Tyr Glu Thr Leu Leu Asn Thr Asp Val Lys Phe Glu Gln Glu
    195                 200                 205 aac atc gct aac ttg atg cat ttg gca gtt act tac ggt aga tca atc    672
Asn Ile Ala Asn Leu Met His Leu Ala Val Thr Tyr Gly Arg Ser Ile
210                 215                 220 ggt ttt aaa ggt gac ttc tac att gaa cca aaa cct aag gaa cca aca    720
Gly Phe Lys Gly Asp Phe Tyr Ile Glu Pro Lys Pro Lys Glu Pro Thr
225                 230                 235                 240 aag cat caa tat gat ttt gat gca gct act aca att ggt ttc att aga    768
Lys His Gln Tyr Asp Phe Asp Ala Ala Thr Thr Ile Gly Phe Ile Arg
            245                 250                 255 caa tac ggt ttg gaa aag gat ttc aag ttg aac atc gaa gca aac cat    816
Gln Tyr Gly Leu Glu Lys Asp Phe Lys Leu Asn Ile Glu Ala Asn His
        260                 265                 270 gct aca tta gca ggt cat acc ttc caa cat gat ttg aga atc tct gct    864
Ala Thr Leu Ala Gly His Thr Phe Gln His Asp Leu Arg Ile Ser Ala
    275                 280                 285 att aat ggc atg tta ggt tca gtt gat gca aac aca ggt gac cca ttg    912
Ile Asn Gly Met Leu Gly Ser Val Asp Ala Asn Thr Gly Asp Pro Leu
290                 295                 300 tta ggt tgg gat acc gat gaa ttt cct tat tcc gtt tac gat acc act    960
Leu Gly Trp Asp Thr Asp Glu Phe Pro Tyr Ser Val Tyr Asp Thr Thr
305                 310                 315                 320 ttg gct atg tac gaa att att aag gca ggt ggt ttg acc ggt ggt ttg    1008
Leu Ala Met Tyr Glu Ile Ile Lys Ala Gly Gly Leu Thr Gly Gly Leu
            325                 330                 335 aat ttt gat tcc aag gtt aga aga cca agt tac aca cat gaa gat ttg    1056
Asn Phe Asp Ser Lys Val Arg Arg Pro Ser Tyr Thr His Glu Asp Leu
        340                 345                 350 ttt tac ggt ttc att ttg ggt atg gat tct ttc gct ttg ggt ttg att    1104
Phe Tyr Gly Phe Ile Leu Gly Met Asp Ser Phe Ala Leu Gly Leu Ile
    355                 360                 365 aaa gca aag gct ttg att gca gat ggt aga ttg gat tca ttc gtt aag    1152
Lys Ala Lys Ala Leu Ile Ala Asp Gly Arg Leu Asp Ser Phe Val Lys
370                 375                 380 gat aga tac gct tct tac ggt tca ggt att ggt gct aag att aga gat    1200
Asp Arg Tyr Ala Ser Tyr Gly Ser Gly Ile Gly Ala Lys Ile Arg Asp
385                 390                 395                 400 cat tct gca act ttg gaa gaa tta gca gct tat gca tta gct aaa gat    1248
His Ser Ala Thr Leu Glu Glu Leu Ala Ala Tyr Ala Leu Ala Lys Asp
            405                 410                 415 aca gtt gct ttg cct ggt tcc ggt aga caa gaa tac tta gaa agt att    1296
Thr Val Ala Leu Pro Gly Ser Gly Arg Gln Glu Tyr Leu Glu Ser Ile
        420                 425                 430 att aac caa att ttg ttt caa taa                                    1320
```

Ile Asn Gln Ile Leu Phe Gln
        435

<210> SEQ ID NO 6
<211> LENGTH: 439
<212> TYPE: PRT
<213> ORGANISM: Unknown
<220> FEATURE:
<223> OTHER INFORMATION: Synthetic Construct

<400> SEQUENCE: 6

Met Ser Gln Ile Phe Lys Asp Ile Pro Val Ile Lys Tyr Glu Gly Pro
1               5                   10                  15

Ala Ser Lys Asn Pro Leu Ser Phe Lys Tyr Tyr Asp Ala Asn Lys Val
            20                  25                  30

Ile Asp Gly Lys Pro Met Lys Glu His Leu Arg Tyr Ala Met Ala Trp
        35                  40                  45

Trp His Asn Leu Cys Ala Thr Gly Gln Asp Met Phe Gly Pro Gly Thr
    50                  55                  60

Ala Asp Lys Ser Phe Gly Ser Lys Thr Val Gly Thr Met Glu His Ala
65                  70                  75                  80

His Ala Lys Val Asp Ala Gly Phe Glu Phe Met Ser Lys Leu Gly Val
                85                  90                  95

Glu Tyr Phe Cys Phe His Asp Ala Asp Leu Val Pro Glu Ala Asp Thr
            100                 105                 110

Leu Ser Glu Thr Asn Lys Arg Leu Asp Glu Ile Ala Glu His Ile Val
        115                 120                 125

Ala Lys Gln Lys Ala Thr Gly Ile Lys Cys Leu Trp Gly Thr Ala Asn
    130                 135                 140

Leu Phe Ser Asn Pro Arg Phe Leu Asn Gly Ser Gly Ser Ser Asn Ser
145                 150                 155                 160

Ala Asp Val Tyr Ala Tyr Ala Ala Ala Gln Ile Lys Lys Ala Leu Asp
                165                 170                 175

Leu Thr Val Lys Phe Gly Gly Val Gly Tyr Val Phe Trp Gly Gly Arg
            180                 185                 190

Glu Gly Tyr Glu Thr Leu Leu Asn Thr Asp Val Lys Phe Glu Gln Glu
        195                 200                 205

Asn Ile Ala Asn Leu Met His Leu Ala Val Thr Tyr Gly Arg Ser Ile
    210                 215                 220

Gly Phe Lys Gly Asp Phe Tyr Ile Glu Pro Lys Pro Lys Glu Pro Thr
225                 230                 235                 240

Lys His Gln Tyr Asp Phe Asp Ala Ala Thr Thr Ile Gly Phe Ile Arg
                245                 250                 255

Gln Tyr Gly Leu Glu Lys Asp Phe Lys Leu Asn Ile Glu Ala Asn His
            260                 265                 270

Ala Thr Leu Ala Gly His Thr Phe Gln His Asp Leu Arg Ile Ser Ala
        275                 280                 285

Ile Asn Gly Met Leu Gly Ser Val Asp Ala Asn Thr Gly Asp Pro Leu
    290                 295                 300

Leu Gly Trp Asp Thr Asp Glu Phe Pro Tyr Ser Val Tyr Asp Thr Thr
305                 310                 315                 320

Leu Ala Met Tyr Glu Ile Ile Lys Ala Gly Gly Leu Thr Gly Gly Leu
                325                 330                 335

Asn Phe Asp Ser Lys Val Arg Arg Pro Ser Tyr Thr Glu Asp Leu
            340                 345                 350

```
Phe Tyr Gly Phe Ile Leu Gly Met Asp Ser Phe Ala Leu Gly Leu Ile
            355                 360                 365

Lys Ala Lys Ala Leu Ile Ala Asp Gly Arg Leu Asp Ser Phe Val Lys
        370                 375                 380

Asp Arg Tyr Ala Ser Tyr Gly Ser Gly Ile Gly Ala Lys Ile Arg Asp
385                 390                 395                 400

His Ser Ala Thr Leu Glu Glu Leu Ala Ala Tyr Ala Leu Ala Lys Asp
                405                 410                 415

Thr Val Ala Leu Pro Gly Ser Gly Arg Gln Tyr Leu Glu Ser Ile
            420                 425                 430

Ile Asn Gln Ile Leu Phe Gln
            435

<210> SEQ ID NO 7
<211> LENGTH: 951
<212> TYPE: DNA
<213> ORGANISM: Escherichia coli
<220> FEATURE:
<221> NAME/KEY: CDS
<222> LOCATION: (1)..(951)

<400> SEQUENCE: 7 atg tca aag aga aaa gtt gct att atc ggt agt gga aac atc ggt act       48
Met Ser Lys Arg Lys Val Ala Ile Ile Gly Ser Gly Asn Ile Gly Thr
1               5                   10                  15 gat ttg atg atc aag atc ctt aga cat gga caa cac ttg gaa atg gct       96
Asp Leu Met Ile Lys Ile Leu Arg His Gly Gln His Leu Glu Met Ala
            20                  25                  30 gtt atg gtc ggt atc gat cct cag tca gac gga ctt gct aga gcc aga      144
Val Met Val Gly Ile Asp Pro Gln Ser Asp Gly Leu Ala Arg Ala Arg
        35                  40                  45 aga atg ggt gtt gct act aca cat gaa ggt gtt att gga ttg atg aac      192
Arg Met Gly Val Ala Thr Thr His Glu Gly Val Ile Gly Leu Met Asn
    50                  55                  60 atg cca gag ttt gca gat att gac atc gtt ttc gat gct aca agt gca      240
Met Pro Glu Phe Ala Asp Ile Asp Ile Val Phe Asp Ala Thr Ser Ala
65                  70                  75                  80 ggt gct cac gtt aag aat gac gct gcc ttg aga gaa gct aaa cct gat      288
Gly Ala His Val Lys Asn Asp Ala Ala Leu Arg Glu Ala Lys Pro Asp
                85                  90                  95 att aga ttg atc gac ctt acc cca gca gct att gga cca tac tgt gtt      336
Ile Arg Leu Ile Asp Leu Thr Pro Ala Ala Ile Gly Pro Tyr Cys Val
            100                 105                 110 cct gtt gtc aac ttg gag gcc aat gtt gat caa ctt aac gtt aat atg      384
Pro Val Val Asn Leu Glu Ala Asn Val Asp Gln Leu Asn Val Asn Met
        115                 120                 125 gtc aca tgc ggt gga cag gct acc att cct atg gtt gcc gca gtc tct      432
Val Thr Cys Gly Gly Gln Ala Thr Ile Pro Met Val Ala Ala Val Ser
    130                 135                 140 aga gtt gct aga gtc cat tat gcc gaa att atc gca tcc atc gct tca      480
Arg Val Ala Arg Val His Tyr Ala Glu Ile Ile Ala Ser Ile Ala Ser
145                 150                 155                 160 aag agt gca ggt cca gga acc aga gct aac att gac gaa ttc act gag      528
Lys Ser Ala Gly Pro Gly Thr Arg Ala Asn Ile Asp Glu Phe Thr Glu
                165                 170                 175 acc act tct aga gct atc gaa gtt gtc ggt gga gct gcc aag ggt aaa      576
Thr Thr Ser Arg Ala Ile Glu Val Val Gly Gly Ala Ala Lys Gly Lys
            180                 185                 190 gcc att atc gtt ttg aat cct gca gag cca cct ctt atg atg aga gat      624
Ala Ile Ile Val Leu Asn Pro Ala Glu Pro Pro Leu Met Met Arg Asp
```

-continued

| | | | | | | | | | | | | | | |
|---|---|---|---|---|---|---|---|---|---|---|---|---|---|---|
| | | 195 | | | | 200 | | | | 205 | | | | |
| act | gtt | tac | gtc | ttg | tct | gac | gaa | gct | tcc | caa | gat | gac | att | gag gcc | 672 |
| Thr | Val | Tyr | Val | Leu | Ser | Asp | Glu | Ala | Ser | Gln | Asp | Asp | Ile | Glu Ala |
| 210 | | | | | 215 | | | | | 220 | | | | |
| tct | atc | aac | gaa | atg | gcc | gag | gca | gtt | cag | gct | tac | gtc | cca | ggt tat | 720 |
| Ser | Ile | Asn | Glu | Met | Ala | Glu | Ala | Val | Gln | Ala | Tyr | Val | Pro | Gly Tyr |
| 225 | | | | | 230 | | | | | 235 | | | | 240 |
| aga | ttg | aag | caa | aga | gtt | cag | ttt | gag | gtc | att | cca | caa | gat | aaa cct | 768 |
| Arg | Leu | Lys | Gln | Arg | Val | Gln | Phe | Glu | Val | Ile | Pro | Gln | Asp | Lys Pro |
| | | | | 245 | | | | | 250 | | | | | 255 |
| gtt | aat | ttg | cca | ggt | gtc | gga | cag | ttc | tcc | gga | ttg | aaa | aca | gct gtt | 816 |
| Val | Asn | Leu | Pro | Gly | Val | Gly | Gln | Phe | Ser | Gly | Leu | Lys | Thr | Ala Val |
| | | | 260 | | | | | 265 | | | | | 270 | |
| tgg | ctt | gaa | gtc | gag | ggt | gca | gct | cac | tac | ttg | cca | gct | tat | gcc gga | 864 |
| Trp | Leu | Glu | Val | Glu | Gly | Ala | Ala | His | Tyr | Leu | Pro | Ala | Tyr | Ala Gly |
| | | 275 | | | | | 280 | | | | | 285 | | |
| aac | ctt | gac | att | atg | act | tct | tcc | gca | ttg | gct | aca | gcc | gaa | aag atg | 912 |
| Asn | Leu | Asp | Ile | Met | Thr | Ser | Ser | Ala | Leu | Ala | Thr | Ala | Glu | Lys Met |
| | 290 | | | | | 295 | | | | | 300 | | | |
| gct | caa | tct | ctt | gcc | aga | aaa | gca | gga | gag | gcc | gca | taa | | | 951 |
| Ala | Gln | Ser | Leu | Ala | Arg | Lys | Ala | Gly | Glu | Ala | Ala | | | |
| 305 | | | | | 310 | | | | | 315 | | | | |

<210> SEQ ID NO 8
<211> LENGTH: 316
<212> TYPE: PRT
<213> ORGANISM: Escherichia coli

<400> SEQUENCE: 8

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
            20                  25                  30

Val Met Val Gly Ile Asp Pro Gln Ser Asp Gly Leu Ala Arg Ala Arg
        35                  40                  45

Arg Met Gly Val Ala Thr Thr His Glu Gly Val Ile Gly Leu Met Asn
    50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
    210                 215                 220

```
Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
            245                 250                 255

Val Asn Leu Pro Gly Val Gly Gln Phe Ser Gly Leu Lys Thr Ala Val
                260                 265                 270

Trp Leu Glu Val Glu Gly Ala Ala His Tyr Leu Pro Ala Tyr Ala Gly
            275                 280                 285

Asn Leu Asp Ile Met Thr Ser Ser Ala Leu Ala Thr Ala Glu Lys Met
                290                 295                 300

Ala Gln Ser Leu Ala Arg Lys Ala Gly Glu Ala Ala
305                 310                 315

<210> SEQ ID NO 9
<211> LENGTH: 2676
<212> TYPE: DNA
<213> ORGANISM: Escherichia coli
<220> FEATURE:
<221> NAME/KEY: CDS
<222> LOCATION: (1)..(2676)

<400> SEQUENCE: 9 atg gca gtt acg aac gtt gca gag ctt aat gcc ctt gtg gag agg gtt      48
Met Ala Val Thr Asn Val Ala Glu Leu Asn Ala Leu Val Glu Arg Val
1               5                   10                  15 aag aaa gca caa agg gaa tac gcc agc ttc acg caa gaa caa gtt gac      96
Lys Lys Ala Gln Arg Glu Tyr Ala Ser Phe Thr Gln Glu Gln Val Asp
            20                  25                  30 aag att ttc agg gca gcc gcg cta gcg gca gct gat gcg aga ata ccc     144
Lys Ile Phe Arg Ala Ala Ala Leu Ala Ala Ala Asp Ala Arg Ile Pro
        35                  40                  45 ctt gct aag atg gca gtc gca gaa agc gga atg gga att gtg gaa gat     192
Leu Ala Lys Met Ala Val Ala Glu Ser Gly Met Gly Ile Val Glu Asp
    50                  55                  60 aag gtc atc aag aat cat ttc gct tct gag tat atc tac aac gcg tat     240
Lys Val Ile Lys Asn His Phe Ala Ser Glu Tyr Ile Tyr Asn Ala Tyr
65                  70                  75                  80 aag gat gag aag act tgc ggc gtc tta tct gag gac gat aca ttc ggc     288
Lys Asp Glu Lys Thr Cys Gly Val Leu Ser Glu Asp Asp Thr Phe Gly
            85                  90                  95 aca ata act atc gct gaa cct ata ggg atc atc tgt ggt ata gtt cca     336
Thr Ile Thr Ile Ala Glu Pro Ile Gly Ile Ile Cys Gly Ile Val Pro
        100                 105                 110 act acg aac cct acc tca act gct ata ttc aag agt ctt att tct ttg     384
Thr Thr Asn Pro Thr Ser Thr Ala Ile Phe Lys Ser Leu Ile Ser Leu
    115                 120                 125 aaa acc cgt aac gct atc atc ttt tct cca cat cca aga gcc aag gac     432
Lys Thr Arg Asn Ala Ile Ile Phe Ser Pro His Pro Arg Ala Lys Asp
130                 135                 140 gcc acc aac aag gcg gcg gac atc gtg ctg cag gcg gcc atc gcg gcg     480
Ala Thr Asn Lys Ala Ala Asp Ile Val Leu Gln Ala Ala Ile Ala Ala
145                 150                 155                 160 ggc gcg cct aag gat cta att ggc tgg atc gac caa cct agc gtt gaa     528
Gly Ala Pro Lys Asp Leu Ile Gly Trp Ile Asp Gln Pro Ser Val Glu
            165                 170                 175 ctt tcc aat gct ctt atg cac cat cct gat att aat ttg ata ctt gcg     576
Leu Ser Asn Ala Leu Met His His Pro Asp Ile Asn Leu Ile Leu Ala
        180                 185                 190 act gga ggc cct ggg atg gta aag gcc gct tat agc agc ggt aag ccc     624
```

```
                Thr Gly Gly Pro Gly Met Val Lys Ala Ala Tyr Ser Ser Gly Lys Pro
                                195                 200                 205 gcc atc ggt gtt ggc gct gga aat acg ccg gta gtc att gat gag acc            672
Ala Ile Gly Val Gly Ala Gly Asn Thr Pro Val Val Ile Asp Glu Thr
210                 215                 220 gcc gac att aag agg gca gtc gcg tca gtt ttg atg tct aag act ttt            720
Ala Asp Ile Lys Arg Ala Val Ala Ser Val Leu Met Ser Lys Thr Phe
225                 230                 235                 240 gac aat gga gta atc tgc gcg tca gag cag tcc gtt gtc gtt gtg gat            768
Asp Asn Gly Val Ile Cys Ala Ser Glu Gln Ser Val Val Val Val Asp
                245                 250                 255 tca gta tac gac gcg gtc aga gaa agg ttc gcg act cac gga ggg tac            816
Ser Val Tyr Asp Ala Val Arg Glu Arg Phe Ala Thr His Gly Gly Tyr
                260                 265                 270 cta ctt caa ggg aag gag ttg aaa gcc gtc cag gac gtt atc ctt aag            864
Leu Leu Gln Gly Lys Glu Leu Lys Ala Val Gln Asp Val Ile Leu Lys
                275                 280                 285 aat ggt gca ttg aac gcc gcc att gta ggc caa cca gcg tat aaa ata            912
Asn Gly Ala Leu Asn Ala Ala Ile Val Gly Gln Pro Ala Tyr Lys Ile
290                 295                 300 gcc gaa ctt gcg ggc ttt agc gta cca gaa aac act aaa ata ctt att            960
Ala Glu Leu Ala Gly Phe Ser Val Pro Glu Asn Thr Lys Ile Leu Ile
305                 310                 315                 320 ggt gaa gtc acc gtg gtt gat gag tca gaa ccc ttc gcc cat gag aaa           1008
Gly Glu Val Thr Val Val Asp Glu Ser Glu Pro Phe Ala His Glu Lys
                325                 330                 335 ctt tcc cca aca ctg gcg atg tac aga gcg aag gac ttt gaa gat gca           1056
Leu Ser Pro Thr Leu Ala Met Tyr Arg Ala Lys Asp Phe Glu Asp Ala
                340                 345                 350 gtg gaa aaa gcc gaa aag ctt gtt gca atg ggc ggt atc ggc cac aca           1104
Val Glu Lys Ala Glu Lys Leu Val Ala Met Gly Gly Ile Gly His Thr
                355                 360                 365 agc tgc ctt tac aca gat cag gat aac caa cca gca aga gtt agt tat           1152
Ser Cys Leu Tyr Thr Asp Gln Asp Asn Gln Pro Ala Arg Val Ser Tyr
370                 375                 380 ttc ggc cag aaa atg aag acg gct agg ata cta atc aac acc ccg gcc           1200
Phe Gly Gln Lys Met Lys Thr Ala Arg Ile Leu Ile Asn Thr Pro Ala
385                 390                 395                 400 agc caa gga ggc att ggt gac ctg tat aac ttc aag ttg gct cct tct           1248
Ser Gln Gly Gly Ile Gly Asp Leu Tyr Asn Phe Lys Leu Ala Pro Ser
                405                 410                 415 ctt aca ttg ggc tgt ggt tcc tgg ggc gga aac tct atc tct gag aac           1296
Leu Thr Leu Gly Cys Gly Ser Trp Gly Gly Asn Ser Ile Ser Glu Asn
                420                 425                 430 gtt gga cct aag cat ctt atc aat aag aaa acc gtc gct aag cgt gct           1344
Val Gly Pro Lys His Leu Ile Asn Lys Lys Thr Val Ala Lys Arg Ala
                435                 440                 445 gag aac atg ctt tgg cac aaa ctg ccg aag tca atc tat ttc cgt agg           1392
Glu Asn Met Leu Trp His Lys Leu Pro Lys Ser Ile Tyr Phe Arg Arg
450                 455                 460 ggc tcc ctg cct atc gcg tta gat gaa gtc atc acc gat ggg cat aag           1440
Gly Ser Leu Pro Ile Ala Leu Asp Glu Val Ile Thr Asp Gly His Lys
465                 470                 475                 480 aga gca cta atc gtc aca gat agg ttc cta ttc aac aac ggt tac gca           1488
Arg Ala Leu Ile Val Thr Asp Arg Phe Leu Phe Asn Asn Gly Tyr Ala
                485                 490                 495 gac caa atc acg tct gtt ctg aaa gcg gcc ggt gtc gaa aca gag gtg           1536
Asp Gln Ile Thr Ser Val Leu Lys Ala Ala Gly Val Glu Thr Glu Val
                500                 505                 510
```

-continued

| | | |
|---|---|---|
| ttc ttc gaa gtg gaa gcc gac ccg aca tta agt att gtc agg aaa gga<br>Phe Phe Glu Val Glu Ala Asp Pro Thr Leu Ser Ile Val Arg Lys Gly<br>515 520 525 | | 1584 |
| gct gag ctt gcg aat agt ttt aag ccg gat gtc atc atc gct ttg gga<br>Ala Glu Leu Ala Asn Ser Phe Lys Pro Asp Val Ile Ile Ala Leu Gly<br>530 535 540 | | 1632 |
| gga gga tcc ccg atg gat gct gct aag atc atg tgg gtc atg tat gaa<br>Gly Gly Ser Pro Met Asp Ala Ala Lys Ile Met Trp Val Met Tyr Glu<br>545 550 555 560 | | 1680 |
| cac ccg gag aca cac ttt gaa gag ttg gcg ttg aga ttc atg gat att<br>His Pro Glu Thr His Phe Glu Glu Leu Ala Leu Arg Phe Met Asp Ile<br>565 570 575 | | 1728 |
| agg aaa agg atc tat aaa ttc cct aag atg gga gtg aaa gcc aag atg<br>Arg Lys Arg Ile Tyr Lys Phe Pro Lys Met Gly Val Lys Ala Lys Met<br>580 585 590 | | 1776 |
| ata gca gtg acg acc acc agt gga acc ggg agt gaa gtg act ccg ttt<br>Ile Ala Val Thr Thr Thr Ser Gly Thr Gly Ser Glu Val Thr Pro Phe<br>595 600 605 | | 1824 |
| gcg gtt gtt act gac gac gct acg ggc cag aag tat ccc cta gcc gac<br>Ala Val Val Thr Asp Asp Ala Thr Gly Gln Lys Tyr Pro Leu Ala Asp<br>610 615 620 | | 1872 |
| tat gca ttg acg ccg gat atg gcg att gtg gac gcg aac ctg gtt atg<br>Tyr Ala Leu Thr Pro Asp Met Ala Ile Val Asp Ala Asn Leu Val Met<br>625 630 635 640 | | 1920 |
| gat atg cca aag tca ctt tgc gca ttc ggt gga ctt gac gca gtt aca<br>Asp Met Pro Lys Ser Leu Cys Ala Phe Gly Gly Leu Asp Ala Val Thr<br>645 650 655 | | 1968 |
| cat gca atg gag gca tat gtg tcc gtg ctt gct tca gag ttt agc gat<br>His Ala Met Glu Ala Tyr Val Ser Val Leu Ala Ser Glu Phe Ser Asp<br>660 665 670 | | 2016 |
| gga cag gca ctt caa gcc ttg aag tta cta aag gaa tac ctt ccc gca<br>Gly Gln Ala Leu Gln Ala Leu Lys Leu Leu Lys Glu Tyr Leu Pro Ala<br>675 680 685 | | 2064 |
| tct tac cat gag ggc agc aag aac cct gtt gcc cgt gag aga gta cat<br>Ser Tyr His Glu Gly Ser Lys Asn Pro Val Ala Arg Glu Arg Val His<br>690 695 700 | | 2112 |
| agt gcg gct acc att gcc ggt atc gca ttc gct aat gct ttc ctg ggt<br>Ser Ala Ala Thr Ile Ala Gly Ile Ala Phe Ala Asn Ala Phe Leu Gly<br>705 710 715 720 | | 2160 |
| gtg tgt cat tca atg gcc cat aag ctt gga tcc cag ttt cac atc cca<br>Val Cys His Ser Met Ala His Lys Leu Gly Ser Gln Phe His Ile Pro<br>725 730 735 | | 2208 |
| cac gga tta gcc aac gct ctt ctt ata tgt aac gtc atc cgt tat aat<br>His Gly Leu Ala Asn Ala Leu Leu Ile Cys Asn Val Ile Arg Tyr Asn<br>740 745 750 | | 2256 |
| gcc aac gac aac cct aca aag caa acc gca ttc tca caa tat gac agg<br>Ala Asn Asp Asn Pro Thr Lys Gln Thr Ala Phe Ser Gln Tyr Asp Arg<br>755 760 765 | | 2304 |
| ccg cag gcg agg cgt cgt tat gca gaa ata gcc gat cac cta ggc tta<br>Pro Gln Ala Arg Arg Arg Tyr Ala Glu Ile Ala Asp His Leu Gly Leu<br>770 775 780 | | 2352 |
| tcc gcg cca gga gat cgt aca gct gct aag att gaa aag ttg ctt gcg<br>Ser Ala Pro Gly Asp Arg Thr Ala Ala Lys Ile Glu Lys Leu Leu Ala<br>785 790 795 800 | | 2400 |
| tgg tta gaa acg ctt aag gcc gaa cta ggc att cca aag tct att aga<br>Trp Leu Glu Thr Leu Lys Ala Glu Leu Gly Ile Pro Lys Ser Ile Arg<br>805 810 815 | | 2448 |
| gag gcg gga gtt caa gag gcg gat ttc ctt gct aac gtg gac aag ctt<br>Glu Ala Gly Val Gln Glu Ala Asp Phe Leu Ala Asn Val Asp Lys Leu<br>820 825 830 | | 2496 |

```
agc gaa gat gca ttc gat gat cag tgc act gga gcc aac ccg aga tat      2544
Ser Glu Asp Ala Phe Asp Asp Gln Cys Thr Gly Ala Asn Pro Arg Tyr
        835             840                 845 cct ctg att tca gaa ttg aag caa att tta ctt gat aca tac tat ggg      2592
Pro Leu Ile Ser Glu Leu Lys Gln Ile Leu Leu Asp Thr Tyr Tyr Gly
850                 855                 860 aga gac tac gtt gag gga gag acc gca gcg aag aag gag gcg gcg ccg      2640
Arg Asp Tyr Val Glu Gly Glu Thr Ala Ala Lys Lys Glu Ala Ala Pro
865                 870                 875                 880 gct aag gcc gag aag aaa gca aag aaa tca gct taa                      2676
Ala Lys Ala Glu Lys Lys Ala Lys Lys Ser Ala
                885                 890
```

<210> SEQ ID NO 10
<211> LENGTH: 891
<212> TYPE: PRT
<213> ORGANISM: Escherichia coli

<400> SEQUENCE: 10

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Thr Phe Gly
            85                  90                  95

Thr Ile Thr Ile Ala Glu Pro Ile Gly Ile Ile Cys Gly Ile Val Pro
        100                 105                 110

Thr Thr Asn Pro Thr Ser Thr Ala Ile Phe Lys Ser Leu Ile Ser Leu
    115                 120                 125

Lys Thr Arg Asn Ala Ile Ile Phe Ser Pro His Pro Arg Ala Lys Asp
130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
            165                 170                 175

Leu Ser Asn Ala Leu Met His His Pro Asp Ile Asn Leu Ile Leu Ala
        180                 185                 190

Thr Gly Gly Pro Gly Met Val Lys Ala Ala Tyr Ser Ser Gly Lys Pro
    195                 200                 205

Ala Ile Gly Val Gly Ala Gly Asn Thr Pro Val Val Ile Asp Glu Thr
210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
            245                 250                 255

Ser Val Tyr Asp Ala Val Arg Glu Arg Phe Ala Thr His Gly Gly Tyr
        260                 265                 270

Leu Leu Gln Gly Lys Glu Leu Lys Ala Val Gln Asp Val Ile Leu Lys
    275                 280                 285
```

Asn Gly Ala Leu Asn Ala Ala Ile Val Gly Gln Pro Ala Tyr Lys Ile
290                 295                 300

Ala Glu Leu Ala Gly Phe Ser Val Pro Glu Asn Thr Lys Ile Leu Ile
305                 310                 315                 320

Gly Glu Val Thr Val Asp Glu Ser Glu Pro Phe Ala His Glu Lys
                325                 330                 335

Leu Ser Pro Thr Leu Ala Met Tyr Arg Ala Lys Asp Phe Glu Asp Ala
                340                 345                 350

Val Glu Lys Ala Glu Lys Leu Val Ala Met Gly Gly Ile Gly His Thr
                355                 360                 365

Ser Cys Leu Tyr Thr Asp Gln Asp Asn Gln Pro Ala Arg Val Ser Tyr
370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
                420                 425                 430

Val Gly Pro Lys His Leu Ile Asn Lys Lys Thr Val Ala Lys Arg Ala
                435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
                500                 505                 510

Phe Phe Glu Val Glu Ala Asp Pro Thr Leu Ser Ile Val Arg Lys Gly
                515                 520                 525

Ala Glu Leu Ala Asn Ser Phe Lys Pro Asp Val Ile Ile Ala Leu Gly
                530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
                595                 600                 605

Ala Val Val Thr Asp Asp Ala Thr Gly Gln Lys Tyr Pro Leu Ala Asp
                610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
                675                 680                 685

Ser Tyr His Glu Gly Ser Lys Asn Pro Val Ala Arg Glu Arg Val His
                690                 695                 700

Ser Ala Ala Thr Ile Ala Gly Ile Ala Phe Ala Asn Ala Phe Leu Gly

```
                    705                 710                 715                 720
        Val Cys His Ser Met Ala His Lys Leu Gly Ser Gln Phe His Ile Pro
                        725                 730                 735

His Gly Leu Ala Asn Ala Leu Leu Ile Cys Asn Val Ile Arg Tyr Asn
                    740                 745                 750

Ala Asn Asp Asn Pro Thr Lys Gln Thr Ala Phe Ser Gln Tyr Asp Arg
                    755                 760                 765

Pro Gln Ala Arg Arg Arg Tyr Ala Glu Ile Ala Asp His Leu Gly Leu
                    770                 775                 780

Ser Ala Pro Gly Asp Arg Thr Ala Ala Lys Ile Glu Lys Leu Leu Ala
        785                 790                 795                 800

Trp Leu Glu Thr Leu Lys Ala Glu Leu Gly Ile Pro Lys Ser Ile Arg
                        805                 810                 815

Glu Ala Gly Val Gln Glu Ala Asp Phe Leu Ala Asn Val Asp Lys Leu
                    820                 825                 830

Ser Glu Asp Ala Phe Asp Asp Gln Cys Thr Gly Ala Asn Pro Arg Tyr
                    835                 840                 845

Pro Leu Ile Ser Glu Leu Lys Gln Ile Leu Leu Asp Thr Tyr Tyr Gly
                    850                 855                 860

Arg Asp Tyr Val Glu Gly Glu Thr Ala Ala Lys Lys Glu Ala Ala Pro
        865                 870                 875                 880

Ala Lys Ala Glu Lys Lys Ala Lys Lys Ser Ala
                        885                 890

<210> SEQ ID NO 11
<211> LENGTH: 1047
<212> TYPE: DNA
<213> ORGANISM: Saccharomyces cerevisiae
<220> FEATURE:
<221> NAME/KEY: CDS
<222> LOCATION: (1)..(1047)

<400> SEQUENCE: 11 atg tct atc cca gaa act caa aaa ggt gtt atc ttc tac gaa tcc cac        48
Met Ser Ile Pro Glu Thr Gln Lys Gly Val Ile Phe Tyr Glu Ser His
1               5                   10                  15 ggt aag ttg gaa tac aaa gat att cca gtt cca aag cca aag gcc aac        96
Gly Lys Leu Glu Tyr Lys Asp Ile Pro Val Pro Lys Pro Lys Ala Asn
            20                  25                  30 gaa ttg ttg atc aac gtt aaa tac tct ggt gtc tgt cac act gac ttg       144
Glu Leu Leu Ile Asn Val Lys Tyr Ser Gly Val Cys His Thr Asp Leu
        35                  40                  45 cac gct tgg cac ggt gac tgg cca ttg cca gtt aag cta cca tta gtc       192
His Ala Trp His Gly Asp Trp Pro Leu Pro Val Lys Leu Pro Leu Val
    50                  55                  60 ggt ggt cac gaa ggt gcc ggt gtc gtt gtc ggc atg ggt gaa aac gtt       240
Gly Gly His Glu Gly Ala Gly Val Val Val Gly Met Gly Glu Asn Val
65                  70                  75                  80 aag ggc tgg aag atc ggt gac tac gcc ggt atc aaa tgg ttg aac ggt       288
Lys Gly Trp Lys Ile Gly Asp Tyr Ala Gly Ile Lys Trp Leu Asn Gly
                85                  90                  95 tct tgt atg gcc tgt gaa tac tgt gaa ttg ggt aac gaa tcc aac tgt       336
Ser Cys Met Ala Cys Glu Tyr Cys Glu Leu Gly Asn Glu Ser Asn Cys
            100                 105                 110 cct cac gct gac ttg tct ggt tac acc cac gac ggt tct ttc caa caa       384
Pro His Ala Asp Leu Ser Gly Tyr Thr His Asp Gly Ser Phe Gln Gln
        115                 120                 125 tac gct acc gct gac gct gtt caa gcc gct cac att cct caa ggt acc       432
```

```
Tyr Ala Thr Ala Asp Ala Val Gln Ala His Ile Pro Gln Gly Thr
    130                 135                 140 gac ttg gcc caa gtc gcc ccc atc ttg tgt gct ggt atc acc gtc tac      480
Asp Leu Ala Gln Val Ala Pro Ile Leu Cys Ala Gly Ile Thr Val Tyr
145                 150                 155                 160 aag gct ttg aag tct gct aac ttg atg gcc ggt cac tgg gtt gct atc      528
Lys Ala Leu Lys Ser Ala Asn Leu Met Ala Gly His Trp Val Ala Ile
                165                 170                 175 tcc ggt gct gct ggt ggt cta ggt tct ttg gct gtt caa tac gcc aag      576
Ser Gly Ala Ala Gly Gly Leu Gly Ser Leu Ala Val Gln Tyr Ala Lys
            180                 185                 190 gct atg ggt tac aga gtc ttg ggt att gac ggt ggt gaa ggt aag gaa      624
Ala Met Gly Tyr Arg Val Leu Gly Ile Asp Gly Gly Glu Gly Lys Glu
        195                 200                 205 gaa tta ttc aga tcc atc ggt ggt gaa gtc ttc att gac ttc act aag      672
Glu Leu Phe Arg Ser Ile Gly Gly Glu Val Phe Ile Asp Phe Thr Lys
    210                 215                 220 gaa aag gac att gtc ggt gct gtt cta aag gcc act gac ggt ggt gct      720
Glu Lys Asp Ile Val Gly Ala Val Leu Lys Ala Thr Asp Gly Gly Ala
225                 230                 235                 240 cac ggt gtc atc aac gtt tcc gtt tcc gaa gcc gct att gaa gct tct      768
His Gly Val Ile Asn Val Ser Val Ser Glu Ala Ala Ile Glu Ala Ser
                245                 250                 255 acc aga tac gtt aga gct aac ggt acc acc gtt ttg gtc ggt atg cca      816
Thr Arg Tyr Val Arg Ala Asn Gly Thr Thr Val Leu Val Gly Met Pro
            260                 265                 270 gct ggt gcc aag tgt tgt tct gat gtc ttc aac caa gtc gtc aag tcc      864
Ala Gly Ala Lys Cys Cys Ser Asp Val Phe Asn Gln Val Val Lys Ser
        275                 280                 285 atc tct att gtt ggt tct tac gtc ggt aac aga gct gac acc aga gaa      912
Ile Ser Ile Val Gly Ser Tyr Val Gly Asn Arg Ala Asp Thr Arg Glu
    290                 295                 300 gct ttg gac ttc ttc gcc aga ggt ttg gtc aag tct cca atc aag gtt      960
Ala Leu Asp Phe Phe Ala Arg Gly Leu Val Lys Ser Pro Ile Lys Val
305                 310                 315                 320 gtc ggc ttg tct acc ttg cca gaa att tac gaa aag atg gaa aag ggt     1008
Val Gly Leu Ser Thr Leu Pro Glu Ile Tyr Glu Lys Met Glu Lys Gly
                325                 330                 335 caa atc gtt ggt aga tac gtt gtt gac act tct aaa taa                 1047
Gln Ile Val Gly Arg Tyr Val Val Asp Thr Ser Lys
            340                 345

<210> SEQ ID NO 12
<211> LENGTH: 348
<212> TYPE: PRT
<213> ORGANISM: Saccharomyces cerevisiae

<400> SEQUENCE: 12

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
                20                  25                  30

Glu Leu Leu Ile Asn Val Lys Tyr Ser Gly Val Cys His Thr Asp Leu
            35                  40                  45

His Ala Trp His Gly Asp Trp Pro Leu Pro Val Lys Leu Pro Leu Val
        50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
```

```
            85                  90                  95
Ser Cys Met Ala Cys Glu Tyr Cys Glu Leu Gly Asn Glu Ser Asn Cys
        100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
                180                 185                 190

Ala Met Gly Tyr Arg Val Leu Gly Ile Asp Gly Gly Glu Gly Lys Glu
                195                 200                 205

Glu Leu Phe Arg Ser Ile Gly Gly Glu Val Phe Ile Asp Phe Thr Lys
        210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
                260                 265                 270

Ala Gly Ala Lys Cys Cys Ser Asp Val Phe Asn Gln Val Val Lys Ser
                275                 280                 285

Ile Ser Ile Val Gly Ser Tyr Val Gly Asn Arg Ala Asp Thr Arg Glu
        290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
                340                 345

<210> SEQ ID NO 13
<211> LENGTH: 1047
<212> TYPE: DNA
<213> ORGANISM: Saccharomyces cerevisiae
<220> FEATURE:
<221> NAME/KEY: CDS
<222> LOCATION: (1)..(1047)

<400> SEQUENCE: 13 atg tct att cca gaa act caa aaa gcc att atc ttc tac gaa tcc aac     48
Met Ser Ile Pro Glu Thr Gln Lys Ala Ile Ile Phe Tyr Glu Ser Asn
1               5                   10                  15 ggc aag ttg gag cat aag gat atc cca gtt cca aag cca aag ccc aac     96
Gly Lys Leu Glu His Lys Asp Ile Pro Val Pro Lys Pro Lys Pro Asn
            20                  25                  30 gaa ttg tta atc aac gtc aag tac tct ggt gtc tgc cac acc gat ttg    144
Glu Leu Leu Ile Asn Val Lys Tyr Ser Gly Val Cys His Thr Asp Leu
        35                  40                  45 cac gct tgg cat ggt gac tgg cca ttg cca act aag tta cca tta gtt    192
His Ala Trp His Gly Asp Trp Pro Leu Pro Thr Lys Leu Pro Leu Val
    50                  55                  60 ggt ggt cac gaa ggt gcc ggt gtc gtt gtc ggc atg ggt gaa aac gtt    240
Gly Gly His Glu Gly Ala Gly Val Val Val Gly Met Gly Glu Asn Val
```

| | | |
|---|---|---|
| aag ggc tgg aag atc ggt gac tac gcc ggt atc aaa tgg ttg aac ggt<br>Lys Gly Trp Lys Ile Gly Asp Tyr Ala Gly Ile Lys Trp Leu Asn Gly<br>85 90 95 | | 288 |
| tct tgt atg gcc tgt gaa tac tgt gaa ttg ggt aac gaa tcc aac tgt<br>Ser Cys Met Ala Cys Glu Tyr Cys Glu Leu Gly Asn Glu Ser Asn Cys<br>100 105 110 | | 336 |
| cct cac gct gac ttg tct ggt tac acc cac gac ggt tct ttc caa gaa<br>Pro His Ala Asp Leu Ser Gly Tyr Thr His Asp Gly Ser Phe Gln Glu<br>115 120 125 | | 384 |
| tac gct acc gct gac gct gtt caa gcc gct cac att cct caa ggt act<br>Tyr Ala Thr Ala Asp Ala Val Gln Ala Ala His Ile Pro Gln Gly Thr<br>130 135 140 | | 432 |
| gac ttg gct gaa gtc gcg cca atc ttg tgt gct ggt atc acc gta tac<br>Asp Leu Ala Glu Val Ala Pro Ile Leu Cys Ala Gly Ile Thr Val Tyr<br>145 150 155 160 | | 480 |
| aag gct ttg aag tct gcc aac ttg aga gca ggc cac tgg gcg gcc att<br>Lys Ala Leu Lys Ser Ala Asn Leu Arg Ala Gly His Trp Ala Ala Ile<br>165 170 175 | | 528 |
| tct ggt gct gct ggt ggt cta ggt tct ttg gct gtt caa tat gct aag<br>Ser Gly Ala Ala Gly Gly Leu Gly Ser Leu Ala Val Gln Tyr Ala Lys<br>180 185 190 | | 576 |
| gcg atg ggt tac aga gtc tta ggt att gat ggt ggt cca gga aag gaa<br>Ala Met Gly Tyr Arg Val Leu Gly Ile Asp Gly Gly Pro Gly Lys Glu<br>195 200 205 | | 624 |
| gaa ttg ttt acc tcg ctc ggt ggt gaa gta ttc atc gac ttc acc aaa<br>Glu Leu Phe Thr Ser Leu Gly Gly Glu Val Phe Ile Asp Phe Thr Lys<br>210 215 220 | | 672 |
| gag aag gac att gtt agc gca gtc gtt aag gct acc aac ggc ggt gcc<br>Glu Lys Asp Ile Val Ser Ala Val Val Lys Ala Thr Asn Gly Gly Ala<br>225 230 235 240 | | 720 |
| cac ggt atc atc aat gtt tcc gtt tcc gaa gcc gct atc gaa gct tct<br>His Gly Ile Ile Asn Val Ser Val Ser Glu Ala Ala Ile Glu Ala Ser<br>245 250 255 | | 768 |
| acc aga tac tgt agg gcg aac ggt act gtt gtc ttg gtt ggt ttg cca<br>Thr Arg Tyr Cys Arg Ala Asn Gly Thr Val Val Leu Val Gly Leu Pro<br>260 265 270 | | 816 |
| gcc ggt gca aag tgc tcc tct gat gtc ttc aac cac gtt gtc aag tct<br>Ala Gly Ala Lys Cys Ser Ser Asp Val Phe Asn His Val Val Lys Ser<br>275 280 285 | | 864 |
| atc tcc att gtc ggc tct tac gtg ggg aac aga gct gat acc aga gaa<br>Ile Ser Ile Val Gly Ser Tyr Val Gly Asn Arg Ala Asp Thr Arg Glu<br>290 295 300 | | 912 |
| gcc tta gat ttc ttt gcc aga ggt cta gtc aag tct cca ata aag gta<br>Ala Leu Asp Phe Phe Ala Arg Gly Leu Val Lys Ser Pro Ile Lys Val<br>305 310 315 320 | | 960 |
| gtt ggc tta tcc agt tta cca gaa att tac gaa aag atg gag aag ggc<br>Val Gly Leu Ser Ser Leu Pro Glu Ile Tyr Glu Lys Met Glu Lys Gly<br>325 330 335 | | 1008 |
| caa att gct ggt aga tac gtt gtt gac act tct aaa taa<br>Gln Ile Ala Gly Arg Tyr Val Val Asp Thr Ser Lys<br>340 345 | | 1047 |

<210> SEQ ID NO 14
<211> LENGTH: 348
<212> TYPE: PRT
<213> ORGANISM: Saccharomyces cerevisiae

<400> SEQUENCE: 14

Met Ser Ile Pro Glu Thr Gln Lys Ala Ile Ile Phe Tyr Glu Ser Asn

```
                1               5                      10                      15
            Gly Lys Leu Glu His Lys Asp Ile Pro Val Pro Lys Pro Lys Pro Asn
                        20                      25                      30
            Glu Leu Leu Ile Asn Val Lys Tyr Ser Gly Val Cys His Thr Asp Leu
                                35                      40                      45
            His Ala Trp His Gly Asp Trp Pro Leu Pro Thr Lys Leu Pro Leu Val
                        50                      55                      60
            Gly Gly His Glu Gly Ala Gly Val Val Gly Met Gly Glu Asn Val
             65                     70                      75                      80
            Lys Gly Trp Lys Ile Gly Asp Tyr Ala Gly Ile Lys Trp Leu Asn Gly
                                85                      90                      95
            Ser Cys Met Ala Cys Glu Tyr Cys Glu Leu Gly Asn Glu Ser Asn Cys
                        100                     105                     110
            Pro His Ala Asp Leu Ser Gly Tyr Thr His Asp Gly Ser Phe Gln Glu
                        115                     120                     125
            Tyr Ala Thr Ala Asp Ala Val Gln Ala Ala His Ile Pro Gln Gly Thr
                        130                     135                     140
            Asp Leu Ala Glu Val Ala Pro Ile Leu Cys Ala Gly Ile Thr Val Tyr
            145                     150                     155                     160
            Lys Ala Leu Lys Ser Ala Asn Leu Arg Ala Gly His Trp Ala Ala Ile
                                165                     170                     175
            Ser Gly Ala Ala Gly Gly Leu Gly Ser Leu Ala Val Gln Tyr Ala Lys
                        180                     185                     190
            Ala Met Gly Tyr Arg Val Leu Gly Ile Asp Gly Gly Pro Gly Lys Glu
                        195                     200                     205
            Glu Leu Phe Thr Ser Leu Gly Gly Glu Val Phe Ile Asp Phe Thr Lys
                        210                     215                     220
            Glu Lys Asp Ile Val Ser Ala Val Val Lys Ala Thr Asn Gly Gly Ala
            225                     230                     235                     240
            His Gly Ile Ile Asn Val Ser Val Ser Glu Ala Ala Ile Glu Ala Ser
                                245                     250                     255
            Thr Arg Tyr Cys Arg Ala Asn Gly Thr Val Val Leu Val Gly Leu Pro
                        260                     265                     270
            Ala Gly Ala Lys Cys Ser Ser Asp Val Phe Asn His Val Val Lys Ser
                        275                     280                     285
            Ile Ser Ile Val Gly Ser Tyr Val Gly Asn Arg Ala Asp Thr Arg Glu
                        290                     295                     300
            Ala Leu Asp Phe Phe Ala Arg Gly Leu Val Lys Ser Pro Ile Lys Val
            305                     310                     315                     320
            Val Gly Leu Ser Ser Leu Pro Glu Ile Tyr Glu Lys Met Glu Lys Gly
                                325                     330                     335
            Gln Ile Ala Gly Arg Tyr Val Val Asp Thr Ser Lys
                        340                     345

<210> SEQ ID NO 15
<211> LENGTH: 1404
<212> TYPE: DNA
<213> ORGANISM: Escherichia coli
<220> FEATURE:
<221> NAME/KEY: CDS
<222> LOCATION: (1)..(1404)

<400> SEQUENCE: 15 atg aac caa caa gac ata gaa caa gta gta aag gca gta tta tta aag     48
Met Asn Gln Gln Asp Ile Glu Gln Val Val Lys Ala Val Leu Leu Lys
 1               5                  10                  15
```

| | | |
|---|---|---|
| atg caa tcc tct gac aca cca cca gcc gca gta cac gaa atg ggt gta<br>Met Gln Ser Ser Asp Thr Pro Pro Ala Ala Val His Glu Met Gly Val<br>20                      25                  30 | | 96 |
| ttt gcc tct ttg gat gac gct gtt gct gca gcc aaa ata gct caa caa<br>Phe Ala Ser Leu Asp Asp Ala Val Ala Ala Ala Lys Ile Ala Gln Gln<br>35                      40                  45 | | 144 |
| ggt ttg aag tca gtt gca atg aga caa tta gcc atc gct gca att aga<br>Gly Leu Lys Ser Val Ala Met Arg Gln Leu Ala Ile Ala Ala Ile Arg<br>50                      55                  60 | | 192 |
| gaa gct ggt gaa aaa cat gca aga gat ttg gcc gaa tta gct gtc tcc<br>Glu Ala Gly Glu Lys His Ala Arg Asp Leu Ala Glu Leu Ala Val Ser<br>65                      70                  75                  80 | | 240 |
| gaa acc ggt atg ggt aga gta gaa gac aaa ttc gct aag aat gtt gct<br>Glu Thr Gly Met Gly Arg Val Glu Asp Lys Phe Ala Lys Asn Val Ala<br>                      85                  90                  95 | | 288 |
| caa gca aga ggt act cca ggt gtt gaa tgt ttg agt cct caa gtc tta<br>Gln Ala Arg Gly Thr Pro Gly Val Glu Cys Leu Ser Pro Gln Val Leu<br>100                     105                 110 | | 336 |
| act ggt gac aac ggt ttg aca ttg atc gaa aac gca cca tgg ggt gtt<br>Thr Gly Asp Asn Gly Leu Thr Leu Ile Glu Asn Ala Pro Trp Gly Val<br>115                     120                 125 | | 384 |
| gtc gcc tct gtt act cca tca aca aat cct gcc gct act gtc atc aat<br>Val Ala Ser Val Thr Pro Ser Thr Asn Pro Ala Ala Thr Val Ile Asn<br>130                     135                 140 | | 432 |
| aac gct ata tct ttg atc gca gcc ggt aac tca gtt att ttt gca cca<br>Asn Ala Ile Ser Leu Ile Ala Ala Gly Asn Ser Val Ile Phe Ala Pro<br>145                     150                 155                 160 | | 480 |
| cat cct gct gct aag aaa gtt tcc caa aga gct atc aca ttg ttg aac<br>His Pro Ala Ala Lys Lys Val Ser Gln Arg Ala Ile Thr Leu Leu Asn<br>                     165                 170                 175 | | 528 |
| caa gca atc gtt gcc gct ggt ggt cca gaa aat ttg tta gtc acc gta<br>Gln Ala Ile Val Ala Ala Gly Gly Pro Glu Asn Leu Leu Val Thr Val<br>180                     185                 190 | | 576 |
| gcc aac cct gat ata gaa act gca caa aga ttg ttc aag ttc cct ggt<br>Ala Asn Pro Asp Ile Glu Thr Ala Gln Arg Leu Phe Lys Phe Pro Gly<br>195                     200                 205 | | 624 |
| atc ggt ttg tta gta gtt aca ggt ggt gaa gct gtc gta gaa gca gcc<br>Ile Gly Leu Leu Val Val Thr Gly Gly Glu Ala Val Val Glu Ala Ala<br>210                     215                 220 | | 672 |
| aga aaa cac acc aat aag aga ttg att gct gca ggt gct ggt aac cca<br>Arg Lys His Thr Asn Lys Arg Leu Ile Ala Ala Gly Ala Gly Asn Pro<br>225                     230                 235                 240 | | 720 |
| cct gtt gtc gta gat gaa act gca gac tta gcc aga gcc gct caa tcc<br>Pro Val Val Val Asp Glu Thr Ala Asp Leu Ala Arg Ala Ala Gln Ser<br>                     245                 250                 255 | | 768 |
| att gtt aag ggt gct agt ttc gat aac aac ata ata tgc gca gac gaa<br>Ile Val Lys Gly Ala Ser Phe Asp Asn Asn Ile Ile Cys Ala Asp Glu<br>260                     265                 270 | | 816 |
| aag gta ttg ata gtt gtc gat tct gtt gct gac gaa ttg atg aga tta<br>Lys Val Leu Ile Val Val Asp Ser Val Ala Asp Glu Leu Met Arg Leu<br>275                     280                 285 | | 864 |
| atg gaa ggt caa cat gca gtt aaa ttg act gct gaa caa gca caa caa<br>Met Glu Gly Gln His Ala Val Lys Leu Thr Ala Glu Gln Ala Gln Gln<br>290                     295                 300 | | 912 |
| ttg caa cca gtt ttg ttg aag aac ata gat gaa aga ggc aag ggt aca<br>Leu Gln Pro Val Leu Leu Lys Asn Ile Asp Glu Arg Gly Lys Gly Thr<br>305                     310                 315                 320 | | 960 |
| gtc tca aga gat tgg gtt ggt aga gac gct ggc aag att gca gcc gct<br>Val Ser Arg Asp Trp Val Gly Arg Asp Ala Gly Lys Ile Ala Ala Ala | | 1008 |

```
                    325                 330                 335
ata ggt tta aag gtc cca caa gaa act aga ttg ttg ttc gta gaa act      1056
Ile Gly Leu Lys Val Pro Gln Glu Thr Arg Leu Leu Phe Val Glu Thr
            340                 345                 350 aca gcc gaa cat cct ttc gct gtc aca gaa ttg atg atg cca gta tta      1104
Thr Ala Glu His Pro Phe Ala Val Thr Glu Leu Met Met Pro Val Leu
            355                 360                 365 cct gta gtt aga gta gct aat gtt gcc gat gct atc gca ttg gcc gtt      1152
Pro Val Val Arg Val Ala Asn Val Ala Asp Ala Ile Ala Leu Ala Val
370                 375                 380 aaa tta gaa ggt ggt tgt cat cac aca gca gcc atg cac tcc aga aac      1200
Lys Leu Glu Gly Gly Cys His His Thr Ala Ala Met His Ser Arg Asn
385                 390                 395                 400 atc gaa aac atg aac caa atg gct aac gca atc gac acc agt att ttt      1248
Ile Glu Asn Met Asn Gln Met Ala Asn Ala Ile Asp Thr Ser Ile Phe
            405                 410                 415 gtt aag aac ggt cca tgc ata gct ggt ttg ggt tta ggt ggt gaa ggt      1296
Val Lys Asn Gly Pro Cys Ile Ala Gly Leu Gly Leu Gly Gly Glu Gly
            420                 425                 430 tgg acc act atg aca atc aca acc cct acc ggt gaa ggt gtt acc tct      1344
Trp Thr Thr Met Thr Ile Thr Thr Pro Thr Gly Glu Gly Val Thr Ser
            435                 440                 445 gct aga act ttt gtc aga ttg aga aga tgt gtt tta gtc gat gca ttc      1392
Ala Arg Thr Phe Val Arg Leu Arg Arg Cys Val Leu Val Asp Ala Phe
450                 455                 460 aga att gtt tag                                                       1404
Arg Ile Val
465

<210> SEQ ID NO 16
<211> LENGTH: 467
<212> TYPE: PRT
<213> ORGANISM: Escherichia coli

<400> SEQUENCE: 16

Met Asn Gln Gln Asp Ile Glu Gln Val Val Lys Ala Val Leu Leu Lys
1               5                   10                  15

Met Gln Ser Ser Asp Thr Pro Pro Ala Ala Val His Glu Met Gly Val
            20                  25                  30

Phe Ala Ser Leu Asp Asp Ala Val Ala Ala Ala Lys Ile Ala Gln Gln
        35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175
```

```
Gln Ala Ile Val Ala Ala Gly Gly Pro Glu Asn Leu Leu Val Thr Val
            180                 185                 190
Ala Asn Pro Asp Ile Glu Thr Ala Gln Arg Leu Phe Lys Phe Pro Gly
        195                 200                 205
Ile Gly Leu Leu Val Val Thr Gly Gly Glu Ala Val Val Glu Ala Ala
    210                 215                 220
Arg Lys His Thr Asn Lys Arg Leu Ile Ala Ala Gly Ala Gly Asn Pro
225                 230                 235                 240
Pro Val Val Val Asp Glu Thr Ala Asp Leu Ala Arg Ala Ala Gln Ser
                245                 250                 255
Ile Val Lys Gly Ala Ser Phe Asp Asn Asn Ile Ile Cys Ala Asp Glu
            260                 265                 270
Lys Val Leu Ile Val Val Asp Ser Val Ala Asp Glu Leu Met Arg Leu
        275                 280                 285
Met Glu Gly Gln His Ala Val Lys Leu Thr Ala Glu Gln Ala Gln Gln
    290                 295                 300
Leu Gln Pro Val Leu Leu Lys Asn Ile Asp Glu Arg Gly Lys Gly Thr
305                 310                 315                 320
Val Ser Arg Asp Trp Val Gly Arg Asp Ala Gly Lys Ile Ala Ala Ala
                325                 330                 335
Ile Gly Leu Lys Val Pro Gln Glu Thr Arg Leu Leu Phe Val Glu Thr
            340                 345                 350
Thr Ala Glu His Pro Phe Ala Val Thr Glu Leu Met Met Pro Val Leu
        355                 360                 365
Pro Val Val Arg Val Ala Asn Val Ala Asp Ala Ile Ala Leu Ala Val
    370                 375                 380
Lys Leu Glu Gly Gly Cys His His Thr Ala Ala Met His Ser Arg Asn
385                 390                 395                 400
Ile Glu Asn Met Asn Gln Met Ala Asn Ala Ile Asp Thr Ser Ile Phe
                405                 410                 415
Val Lys Asn Gly Pro Cys Ile Ala Gly Leu Gly Leu Gly Gly Glu Gly
            420                 425                 430
Trp Thr Thr Met Thr Ile Thr Thr Pro Thr Gly Glu Gly Val Thr Ser
        435                 440                 445
Ala Arg Thr Phe Val Arg Leu Arg Arg Cys Val Leu Val Asp Ala Phe
    450                 455                 460
Arg Ile Val
465

<210> SEQ ID NO 17
<211> LENGTH: 21
<212> TYPE: DNA
<213> ORGANISM: Artificial
<220> FEATURE:
<223> OTHER INFORMATION: Synthetic DNA

<400> SEQUENCE: 17
tgggaatatt accgctcgaa g                                          21

<210> SEQ ID NO 18
<211> LENGTH: 29
<212> TYPE: DNA
<213> ORGANISM: Artificial
<220> FEATURE:
<223> OTHER INFORMATION: Synthetic DNA

<400> SEQUENCE: 18
```

```
ctttaaaaaa tttccaattt tcctttacg                                         29
```

<210> SEQ ID NO 19
<211> LENGTH: 33
<212> TYPE: DNA
<213> ORGANISM: Artificial
<220> FEATURE:
<223> OTHER INFORMATION: Synthetic DNA

<400> SEQUENCE: 19

```
ggaaattttt taaagtcgca gccacgggtc aac                                    33
```

<210> SEQ ID NO 20
<211> LENGTH: 50
<212> TYPE: DNA
<213> ORGANISM: Artificial
<220> FEATURE:
<223> OTHER INFORMATION: Synthetic DNA

<400> SEQUENCE: 20

```
gtgaattgag tcatttttta ttattagtct tttttttttt tgacaatatc                  50
```

<210> SEQ ID NO 21
<211> LENGTH: 31
<212> TYPE: DNA
<213> ORGANISM: Artificial
<220> FEATURE:
<223> OTHER INFORMATION: Synthetic DNA

<400> SEQUENCE: 21

```
atgactcaat tcactgacat tgataagcta g                                      31
```

<210> SEQ ID NO 22
<211> LENGTH: 37
<212> TYPE: DNA
<213> ORGANISM: Artificial
<220> FEATURE:
<223> OTHER INFORMATION: Synthetic DNA

<400> SEQUENCE: 22

```
ccttaaatca acgtcatatt ctttattggc tttatac                                37
```

<210> SEQ ID NO 23
<211> LENGTH: 24
<212> TYPE: DNA
<213> ORGANISM: Artificial
<220> FEATURE:
<223> OTHER INFORMATION: Synthetic DNA

<400> SEQUENCE: 23

```
gacgttgatt taaggtggtt ccgg                                              24
```

<210> SEQ ID NO 24
<211> LENGTH: 25
<212> TYPE: DNA
<213> ORGANISM: Artificial
<220> FEATURE:
<223> OTHER INFORMATION: Synthetic DNA

<400> SEQUENCE: 24

```
atgtctgaac cagctcaaaa gaaac                                             25
```

<210> SEQ ID NO 25
<211> LENGTH: 52
<212> TYPE: DNA
<213> ORGANISM: Artificial

```
<220> FEATURE:
<223> OTHER INFORMATION: Synthetic DNA

<400> SEQUENCE: 25
agctggttca gacattttga atatgtatta cttggttatg gttatatatg ac        52

<210> SEQ ID NO 26
<211> LENGTH: 25
<212> TYPE: DNA
<213> ORGANISM: Artificial
<220> FEATURE:
<223> OTHER INFORMATION: Synthetic DNA

<400> SEQUENCE: 26
actggtagag agcgactttg tatgc                                       25

<210> SEQ ID NO 27
<211> LENGTH: 41
<212> TYPE: DNA
<213> ORGANISM: Artificial
<220> FEATURE:
<223> OTHER INFORMATION: Synthetic DNA

<400> SEQUENCE: 27
caaagtcgct ctctaccagt cgctttcaat tcatttgggt g                     41

<210> SEQ ID NO 28
<211> LENGTH: 26
<212> TYPE: DNA
<213> ORGANISM: Artificial
<220> FEATURE:
<223> OTHER INFORMATION: Synthetic DNA

<400> SEQUENCE: 28
tgtatatgag atagttgatt gtatgc                                      26

<210> SEQ ID NO 29
<211> LENGTH: 39
<212> TYPE: DNA
<213> ORGANISM: Artificial
<220> FEATURE:
<223> OTHER INFORMATION: Synthetic DNA

<400> SEQUENCE: 29
actatctcat atacaatggt caaaccaatt atagctccc                        39

<210> SEQ ID NO 30
<211> LENGTH: 25
<212> TYPE: DNA
<213> ORGANISM: Artificial
<220> FEATURE:
<223> OTHER INFORMATION: Synthetic DNA

<400> SEQUENCE: 30
aaatggatat tgatctagat ggcgg                                       25

<210> SEQ ID NO 31
<211> LENGTH: 41
<212> TYPE: DNA
<213> ORGANISM: Artificial
<220> FEATURE:
<223> OTHER INFORMATION: Synthetic DNA

<400> SEQUENCE: 31
gatcaatatc catttcttgg tgtgtcatcg gtagtaacgc c                     41
```

<210> SEQ ID NO 32
<211> LENGTH: 35
<212> TYPE: DNA
<213> ORGANISM: Artificial
<220> FEATURE:
<223> OTHER INFORMATION: Synthetic DNA

<400> SEQUENCE: 32
agttttaatt acaaaatggc tgccggtgtc ccaaa                        35

<210> SEQ ID NO 33
<211> LENGTH: 36
<212> TYPE: DNA
<213> ORGANISM: Artificial
<220> FEATURE:
<223> OTHER INFORMATION: Synthetic DNA

<400> SEQUENCE: 33
ttgtaattaa aacttagatt agattgctat gctttc                       36

<210> SEQ ID NO 34
<211> LENGTH: 18
<212> TYPE: DNA
<213> ORGANISM: Artificial
<220> FEATURE:
<223> OTHER INFORMATION: Synthetic DNA

<400> SEQUENCE: 34
aggaacagcc gtcaaggg                                           18

<210> SEQ ID NO 35
<211> LENGTH: 35
<212> TYPE: DNA
<213> ORGANISM: Artificial
<220> FEATURE:
<223> OTHER INFORMATION: Synthetic DNA

<400> SEQUENCE: 35
ttgacggctg ttcctcttcc cttttacagt gcttc                        35

<210> SEQ ID NO 36
<211> LENGTH: 32
<212> TYPE: DNA
<213> ORGANISM: Artificial
<220> FEATURE:
<223> OTHER INFORMATION: Synthetic DNA

<400> SEQUENCE: 36
tttgttttgt gtgtaaattt agtgaagtac tg                           32

<210> SEQ ID NO 37
<211> LENGTH: 41
<212> TYPE: DNA
<213> ORGANISM: Artificial
<220> FEATURE:
<223> OTHER INFORMATION: Synthetic DNA

<400> SEQUENCE: 37
tacacacaaa acaaaatgtc tcaaattttt aaggatatcc c                 41

<210> SEQ ID NO 38
<211> LENGTH: 39
<212> TYPE: DNA
<213> ORGANISM: Artificial
<220> FEATURE:
<223> OTHER INFORMATION: Synthetic DNA

<400> SEQUENCE: 38
agcgctctta ctttagcgat cgcactagtt tattgaaac                                    39

<210> SEQ ID NO 39
<211> LENGTH: 28
<212> TYPE: DNA
<213> ORGANISM: Artificial
<220> FEATURE:
<223> OTHER INFORMATION: Synthetic DNA

<400> SEQUENCE: 39
taaagtaaga gcgctacatt ggtctacc                                                28

<210> SEQ ID NO 40
<211> LENGTH: 36
<212> TYPE: DNA
<213> ORGANISM: Artificial
<220> FEATURE:
<223> OTHER INFORMATION: Synthetic DNA

<400> SEQUENCE: 40
taacattcaa cgctattact ccgcaacgct tttctg                                       36

<210> SEQ ID NO 41
<211> LENGTH: 26
<212> TYPE: DNA
<213> ORGANISM: Artificial
<220> FEATURE:
<223> OTHER INFORMATION: Synthetic DNA

<400> SEQUENCE: 41
tagcgttgaa tgttagcgtc aacaac                                                  26

<210> SEQ ID NO 42
<211> LENGTH: 41
<212> TYPE: DNA
<213> ORGANISM: Artificial
<220> FEATURE:
<223> OTHER INFORMATION: Synthetic DNA

<400> SEQUENCE: 42
tttgtttgtt tatgtgtgtt tattcgaaac taagttcttg g                                 41

<210> SEQ ID NO 43
<211> LENGTH: 42
<212> TYPE: DNA
<213> ORGANISM: Artificial
<220> FEATURE:
<223> OTHER INFORMATION: Synthetic DNA

<400> SEQUENCE: 43
acataaacaa acaaaatgtt gtgttcagta attcagagac ag                                42

<210> SEQ ID NO 44
<211> LENGTH: 39
<212> TYPE: DNA
<213> ORGANISM: Artificial
<220> FEATURE:
<223> OTHER INFORMATION: Synthetic DNA

<400> SEQUENCE: 44
aaataatcgg tgtcattaga tgagagtctt ttccagttc                                    39

<210> SEQ ID NO 45

```
<211> LENGTH: 25
<212> TYPE: DNA
<213> ORGANISM: Artificial
<220> FEATURE:
<223> OTHER INFORMATION: Synthetic DNA

<400> SEQUENCE: 45
tgacaccgat tatttaaagc tgcag                                            25

<210> SEQ ID NO 46
<211> LENGTH: 18
<212> TYPE: DNA
<213> ORGANISM: Artificial
<220> FEATURE:
<223> OTHER INFORMATION: Synthetic DNA

<400> SEQUENCE: 46
agagcgcgcc tcgttcag                                                    18

<210> SEQ ID NO 47
<211> LENGTH: 33
<212> TYPE: DNA
<213> ORGANISM: Artificial
<220> FEATURE:
<223> OTHER INFORMATION: Synthetic DNA

<400> SEQUENCE: 47
aacgaggcgc gctctaattc cgctgtatag ctc                                   33

<210> SEQ ID NO 48
<211> LENGTH: 45
<212> TYPE: DNA
<213> ORGANISM: Artificial
<220> FEATURE:
<223> OTHER INFORMATION: Synthetic DNA

<400> SEQUENCE: 48
ataatgtatg ctatacgaag ttatagggaa agatatgagc tatac                      45

<210> SEQ ID NO 49
<211> LENGTH: 43
<212> TYPE: DNA
<213> ORGANISM: Artificial
<220> FEATURE:
<223> OTHER INFORMATION: Synthetic DNA

<400> SEQUENCE: 49
tatagcatac attatacgaa gttatacgac atcgtcgaat atg                        43

<210> SEQ ID NO 50
<211> LENGTH: 33
<212> TYPE: DNA
<213> ORGANISM: Artificial
<220> FEATURE:
<223> OTHER INFORMATION: Synthetic DNA

<400> SEQUENCE: 50
tattaattta gtgtgtgtat ttgtgtttgt gtg                                   33

<210> SEQ ID NO 51
<211> LENGTH: 34
<212> TYPE: DNA
<213> ORGANISM: Artificial
<220> FEATURE:
<223> OTHER INFORMATION: Synthetic DNA

<400> SEQUENCE: 51
```

```
cacactaaat taataatgag ccatattcaa cggg                          34

<210> SEQ ID NO 52
<211> LENGTH: 38
<212> TYPE: DNA
<213> ORGANISM: Artificial
<220> FEATURE:
<223> OTHER INFORMATION: Synthetic DNA

<400> SEQUENCE: 52
tttagtagac atgcattaca accaattaac caattctg                      38

<210> SEQ ID NO 53
<211> LENGTH: 37
<212> TYPE: DNA
<213> ORGANISM: Artificial
<220> FEATURE:
<223> OTHER INFORMATION: Synthetic DNA

<400> SEQUENCE: 53
tgcatgtcta ctaaactcac aaattagagc ttcaatt                       37

<210> SEQ ID NO 54
<211> LENGTH: 54
<212> TYPE: DNA
<213> ORGANISM: Artificial
<220> FEATURE:
<223> OTHER INFORMATION: Synthetic DNA

<400> SEQUENCE: 54
ataatgtatg ctatacgaag ttatgggtaa taactgatat aattaaattg aagc    54

<210> SEQ ID NO 55
<211> LENGTH: 47
<212> TYPE: DNA
<213> ORGANISM: Artificial
<220> FEATURE:
<223> OTHER INFORMATION: Synthetic DNA

<400> SEQUENCE: 55
tatagcatac attatacgaa gttattgaca ccgattattt aaagctg            47

<210> SEQ ID NO 56
<211> LENGTH: 39
<212> TYPE: DNA
<213> ORGANISM: Artificial
<220> FEATURE:
<223> OTHER INFORMATION: Synthetic DNA

<400> SEQUENCE: 56
attttactgg ctggagtatg ctgcagcttt aaataatcg                     39

<210> SEQ ID NO 57
<211> LENGTH: 26
<212> TYPE: DNA
<213> ORGANISM: Artificial
<220> FEATURE:
<223> OTHER INFORMATION: Synthetic DNA

<400> SEQUENCE: 57
tccagccagt aaaatccata ctcaac                                   26

<210> SEQ ID NO 58
<211> LENGTH: 20
<212> TYPE: DNA
```

```
<213> ORGANISM: Artificial
<220> FEATURE:
<223> OTHER INFORMATION: Synthetic DNA

<400> SEQUENCE: 58 gtcttttgc cagccagtcc                                              20

<210> SEQ ID NO 59
<211> LENGTH: 33
<212> TYPE: DNA
<213> ORGANISM: Artificial
<220> FEATURE:
<223> OTHER INFORMATION: Synthetic DNA

<400> SEQUENCE: 59
cacaccttcc cccttgatcc tctagagtcg acc                              33

<210> SEQ ID NO 60
<211> LENGTH: 35
<212> TYPE: DNA
<213> ORGANISM: Artificial
<220> FEATURE:
<223> OTHER INFORMATION: Synthetic DNA

<400> SEQUENCE: 60
gcggtaatat tcccagatcc ccgggtaccg agctc                            35

<210> SEQ ID NO 61
<211> LENGTH: 33
<212> TYPE: DNA
<213> ORGANISM: Artificial
<220> FEATURE:
<223> OTHER INFORMATION: Synthetic DNA

<400> SEQUENCE: 61
cggtacccgg ggatcctatg ggacttccgg gaa                              33

<210> SEQ ID NO 62
<211> LENGTH: 46
<212> TYPE: DNA
<213> ORGANISM: Artificial
<220> FEATURE:
<223> OTHER INFORMATION: Synthetic DNA

<400> SEQUENCE: 62
taacattcaa cgctatgtgt attacgatat agttaatagt tgatag                46

<210> SEQ ID NO 63
<211> LENGTH: 26
<212> TYPE: DNA
<213> ORGANISM: Artificial
<220> FEATURE:
<223> OTHER INFORMATION: Synthetic DNA

<400> SEQUENCE: 63
tagcgttgaa tgttagcgtc aacaac                                      26

<210> SEQ ID NO 64
<211> LENGTH: 41
<212> TYPE: DNA
<213> ORGANISM: Artificial
<220> FEATURE:
<223> OTHER INFORMATION: Synthetic DNA

<400> SEQUENCE: 64
tttgtttgtt tatgtgtgtt tattcgaaac taagttcttg g                     41
```

<210> SEQ ID NO 65
<211> LENGTH: 40
<212> TYPE: DNA
<213> ORGANISM: Artificial
<220> FEATURE:
<223> OTHER INFORMATION: Synthetic DNA

<400> SEQUENCE: 65
acataaacaa acaaaatgtc tatcccagaa actcaaaaag                    40

<210> SEQ ID NO 66
<211> LENGTH: 30
<212> TYPE: DNA
<213> ORGANISM: Artificial
<220> FEATURE:
<223> OTHER INFORMATION: Synthetic DNA

<400> SEQUENCE: 66
ttgtcctctg aggacataaa atacacaccg                              30

<210> SEQ ID NO 67
<211> LENGTH: 34
<212> TYPE: DNA
<213> ORGANISM: Artificial
<220> FEATURE:
<223> OTHER INFORMATION: Synthetic DNA

<400> SEQUENCE: 67
gtcctcagag gacaattact ccgcaacgct tttc                         34

<210> SEQ ID NO 68
<211> LENGTH: 37
<212> TYPE: DNA
<213> ORGANISM: Artificial
<220> FEATURE:
<223> OTHER INFORMATION: Synthetic DNA

<400> SEQUENCE: 68
ggagaggccg cataataaag taagagcgct acattgg                      37

<210> SEQ ID NO 69
<211> LENGTH: 18
<212> TYPE: DNA
<213> ORGANISM: Artificial
<220> FEATURE:
<223> OTHER INFORMATION: Synthetic DNA

<400> SEQUENCE: 69
ttatgcggcc tctcctgc                                           18

<210> SEQ ID NO 70
<211> LENGTH: 43
<212> TYPE: DNA
<213> ORGANISM: Artificial
<220> FEATURE:
<223> OTHER INFORMATION: Synthetic DNA

<400> SEQUENCE: 70
agactaataa taaaaatgtc aaagagaaaa gttgctatta tcg                43

<210> SEQ ID NO 71
<211> LENGTH: 47
<212> TYPE: DNA
<213> ORGANISM: Artificial
<220> FEATURE:

<223> OTHER INFORMATION: Synthetic DNA

<400> SEQUENCE: 71
tttttattat tagtcttttt ttttttttgac aatatctgta tgatttg                47

<210> SEQ ID NO 72
<211> LENGTH: 33
<212> TYPE: DNA
<213> ORGANISM: Artificial
<220> FEATURE:
<223> OTHER INFORMATION: Synthetic DNA

<400> SEQUENCE: 72
ggagattacc gaatctcgct cgcagccacg ggt                                33

<210> SEQ ID NO 73
<211> LENGTH: 21
<212> TYPE: DNA
<213> ORGANISM: Artificial
<220> FEATURE:
<223> OTHER INFORMATION: Synthetic DNA

<400> SEQUENCE: 73
gattcggtaa tctccgagca g                                             21

<210> SEQ ID NO 74
<211> LENGTH: 41
<212> TYPE: DNA
<213> ORGANISM: Artificial
<220> FEATURE:
<223> OTHER INFORMATION: Synthetic DNA

<400> SEQUENCE: 74
acataagaga tccgcgggta ataactgata taattaaatt g                       41

<210> SEQ ID NO 75
<211> LENGTH: 35
<212> TYPE: DNA
<213> ORGANISM: Artificial
<220> FEATURE:
<223> OTHER INFORMATION: Synthetic DNA

<400> SEQUENCE: 75
gcggatctct tatgtcttta cgatttatag ttttc                              35

<210> SEQ ID NO 76
<211> LENGTH: 20
<212> TYPE: DNA
<213> ORGANISM: Artificial
<220> FEATURE:
<223> OTHER INFORMATION: Synthetic DNA

<400> SEQUENCE: 76
gagggttggg cattcatcag                                               20

<210> SEQ ID NO 77
<211> LENGTH: 32
<212> TYPE: DNA
<213> ORGANISM: Artificial
<220> FEATURE:
<223> OTHER INFORMATION: Synthetic DNA

<400> SEQUENCE: 77
aatgcccaac cctcgatcct ctagagtcga cc                                 32

<210> SEQ ID NO 78
<211> LENGTH: 18
<212> TYPE: DNA
<213> ORGANISM: Artificial
<220> FEATURE:
<223> OTHER INFORMATION: Synthetic DNA

<400> SEQUENCE: 78
gatccccggg taccgagc                                                 18

<210> SEQ ID NO 79
<211> LENGTH: 37
<212> TYPE: DNA
<213> ORGANISM: Artificial
<220> FEATURE:
<223> OTHER INFORMATION: Synthetic DNA

<400> SEQUENCE: 79
ttttattatt agtctttttt tttttgaca atatctg                             37

<210> SEQ ID NO 80
<211> LENGTH: 28
<212> TYPE: DNA
<213> ORGANISM: Artificial
<220> FEATURE:
<223> OTHER INFORMATION: Synthetic DNA

<400> SEQUENCE: 80
taaagtaaga gcgctacatt ggtctacc                                      28

<210> SEQ ID NO 81
<211> LENGTH: 40
<212> TYPE: DNA
<213> ORGANISM: Artificial
<220> FEATURE:
<223> OTHER INFORMATION: Synthetic DNA

<400> SEQUENCE: 81
agcgctctta ctttattaag ctgatttctt tgctttcttc                         40

<210> SEQ ID NO 82
<211> LENGTH: 37
<212> TYPE: DNA
<213> ORGANISM: Artificial
<220> FEATURE:
<223> OTHER INFORMATION: Synthetic DNA

<400> SEQUENCE: 82
agactaataa taaaaatggc agttacgaac gttgcag                            37

<210> SEQ ID NO 83
<211> LENGTH: 46
<212> TYPE: DNA
<213> ORGANISM: Artificial
<220> FEATURE:
<223> OTHER INFORMATION: Synthetic DNA

<400> SEQUENCE: 83
cggtacccgg ggatcatttt gatgctgatg ttgatgtata gtaaac                  46

<210> SEQ ID NO 84
<211> LENGTH: 53
<212> TYPE: DNA
<213> ORGANISM: Artificial
<220> FEATURE:
<223> OTHER INFORMATION: Synthetic DNA

<400> SEQUENCE: 84
aagatatgag ctatacagcg gaattcaatc gacacactta tagttctagc ccc    53

<210> SEQ ID NO 85
<211> LENGTH: 22
<212> TYPE: DNA
<213> ORGANISM: Artificial
<220> FEATURE:
<223> OTHER INFORMATION: Synthetic DNA

<400> SEQUENCE: 85
agaggcatag cggcaaacta ag    22

<210> SEQ ID NO 86
<211> LENGTH: 25
<212> TYPE: DNA
<213> ORGANISM: Artificial
<220> FEATURE:
<223> OTHER INFORMATION: Synthetic DNA

<400> SEQUENCE: 86
gcggattgag agcaaatcgt taagt    25

<210> SEQ ID NO 87
<211> LENGTH: 39
<212> TYPE: DNA
<213> ORGANISM: Artificial
<220> FEATURE:
<223> OTHER INFORMATION: Synthetic DNA

<400> SEQUENCE: 87
ttgctctcaa tccgcctaaa caattctgaa tgcatcgac    39

<210> SEQ ID NO 88
<211> LENGTH: 40
<212> TYPE: DNA
<213> ORGANISM: Artificial
<220> FEATURE:
<223> OTHER INFORMATION: Synthetic DNA

<400> SEQUENCE: 88
acataaacaa acaaaatgaa ccaacaagac atagaacaag    40

<210> SEQ ID NO 89
<211> LENGTH: 55
<212> TYPE: DNA
<213> ORGANISM: Artificial
<220> FEATURE:
<223> OTHER INFORMATION: Synthetic DNA

<400> SEQUENCE: 89
tttgtttgtt tatgtgtgtt tattcgaaac taagttcttg gtgttttaaa actaa    55

<210> SEQ ID NO 90
<211> LENGTH: 26
<212> TYPE: DNA
<213> ORGANISM: Artificial
<220> FEATURE:
<223> OTHER INFORMATION: Synthetic DNA

<400> SEQUENCE: 90
tagcgttgaa tgttagcgtc aacaac    26

<210> SEQ ID NO 91
<211> LENGTH: 27

<212> TYPE: DNA
<213> ORGANISM: Artificial
<220> FEATURE:
<223> OTHER INFORMATION: Synthetic DNA

<400> SEQUENCE: 91
aattccgctg tatagctcat atctttc                                       27

<210> SEQ ID NO 92
<211> LENGTH: 25
<212> TYPE: DNA
<213> ORGANISM: Artificial
<220> FEATURE:
<223> OTHER INFORMATION: Synthetic DNA

<400> SEQUENCE: 92
gtatgctgca gctttaaata atcgg                                         25

<210> SEQ ID NO 93
<211> LENGTH: 40
<212> TYPE: DNA
<213> ORGANISM: Artificial
<220> FEATURE:
<223> OTHER INFORMATION: Synthetic DNA

<400> SEQUENCE: 93
aaagctgcag catacgcaga ggccttgtcc cttttttatg                         40

<210> SEQ ID NO 94
<211> LENGTH: 37
<212> TYPE: DNA
<213> ORGANISM: Artificial
<220> FEATURE:
<223> OTHER INFORMATION: Synthetic DNA

<400> SEQUENCE: 94
cgactctaga ggatccagtc gaggcatgaa gtggaag                            37

<210> SEQ ID NO 95
<211> LENGTH: 25
<212> TYPE: DNA
<213> ORGANISM: Artificial
<220> FEATURE:
<223> OTHER INFORMATION: Synthetic DNA

<400> SEQUENCE: 95
gatcctctag agtcgacctg caggc                                         25

<210> SEQ ID NO 96
<211> LENGTH: 18
<212> TYPE: DNA
<213> ORGANISM: Artificial
<220> FEATURE:
<223> OTHER INFORMATION: Synthetic DNA

<400> SEQUENCE: 96
gatccccggg taccgagc                                                 18

<210> SEQ ID NO 97
<211> LENGTH: 20
<212> TYPE: DNA
<213> ORGANISM: Artificial
<220> FEATURE:
<223> OTHER INFORMATION: Synthetic DNA

```
<400> SEQUENCE: 97
aggctactgc gccaattgat                                               20

<210> SEQ ID NO 98
<211> LENGTH: 20
<212> TYPE: DNA
<213> ORGANISM: Artificial
<220> FEATURE:
<223> OTHER INFORMATION: Synthetic DNA

<400> SEQUENCE: 98
tgccctacac gttcgctatg                                               20

<210> SEQ ID NO 99
<211> LENGTH: 29
<212> TYPE: DNA
<213> ORGANISM: Artificial
<220> FEATURE:
<223> OTHER INFORMATION: Synthetic DNA

<400> SEQUENCE: 99 ggtttttct ccttgacgtt aaagtatag                                      29

<210> SEQ ID NO 100
<211> LENGTH: 26
<212> TYPE: DNA
<213> ORGANISM: Artificial
<220> FEATURE:
<223> OTHER INFORMATION: Synthetic DNA

<400> SEQUENCE: 100
ttagttatgt cacgcttaca ttcacg                                        26

<210> SEQ ID NO 101
<211> LENGTH: 22
<212> TYPE: DNA
<213> ORGANISM: Artificial
<220> FEATURE:
<223> OTHER INFORMATION: Synthetic DNA

<400> SEQUENCE: 101
atgtctaact tgttgactgt tc                                            22

<210> SEQ ID NO 102
<211> LENGTH: 23
<212> TYPE: DNA
<213> ORGANISM: Artificial
<220> FEATURE:
<223> OTHER INFORMATION: Synthetic DNA

<400> SEQUENCE: 102
tcaatcacca tcttccaaca atc                                           23
```

RECOMBINANT YEAST AND A METHOD FOR PRODUCING ETHANOL USING THE SAME

CROSS REFERENCE TO RELATED APPLICATIONS

The present application claims priority from Japanese patent application JP 2017-150169 filed on Aug. 2, 2017, the content of which is hereby incorporated by reference into this application.

BACKGROUND

Technical Field

The present disclosure relates to a recombinant yeast strain having xylose-metabolizing ability and a method for producing ethanol using the same.

Background Art

A cellulosic biomass is an effective starting material for a useful alcohol, such as ethanol, or an organic acid. In order to increase the amount of ethanol produced with the use of a cellulosic biomass, yeast strains capable of utilizing a xylose, which is a pentose, as a substrate have been developed. For example, JP 2009-195220 A discloses a recombinant yeast strain resulting from incorporation of a xylose reductase gene and a xylitol dehydrogenase gene derived from *Pichia stipitis* and a xylulokinase gene derived from *S. cerevisiae* into its chromosome.

It is known that a large amount of acetic acid is contained in a hydrolysate of a cellulosic biomass and that acetic acid inhibits ethanol fermentation by a yeast strain. In the case of a yeast strain into which a xylose-assimilating gene has been introduced, in particular, acetic acid is known to inhibit ethanol fermentation carried out with the use of xylose as a saccharide source at a significant level (FEMS Yeast Research, vol. 9, 2009, 358-364, and Enzyme and Microbial Technology 33, 2003, 786-792).

A mash (moromi) resulting from fermentation of a cellulosic biomass saccharified with a cellulase is mainly composed of unfermented residue, poorly fermentable residue, enzymes, and fermenting microorganisms. Use of a mash-containing reaction solution for the subsequent fermentation process enables the reuse of fermenting microorganisms, reduction of the quantity of fermenting microorganisms to be introduced, and cost reduction. In such a case, however, acetic acid contained in the mash is simultaneously introduced, the concentration of acetic acid contained in a fermentation medium is then increased via repeated use of fermenting microorganisms, and this may inhibit ethanol fermentation. According to a continuous fermentation technique, the mash in a fermentation tank is transferred to a flash tank in which a reduced pressure level is maintained, ethanol is removed from the flash tank, and the mash is returned to the fermentation tank. In such a technique, it is difficult to remove acetic acid from the mash, and inhibition of acetic acid-mediated fermentation is accordingly a serious issue of concern. Accordingly, it would be very critical to reduce the amount of acetic acid in the fermentation liquor during the process of fermentation, from the viewpoint of cost reduction.

In order to prevent fermentation from being inhibited by acetic acid, there are reports concerning ethanol fermentation ability in the presence of acetic acid that has been improved by means of LPP1 or ENA1 gene overexpression (Biotechnol. Bioeng., 2009, 103 (3): 500-512) or FPS1 gene disruption (Biotechnol. Lett., 2011, 33: 277-284) of *Saccharomyces cerevisiae*, which is a strain generally used for ethanol fermentation. However, such literatures report the results concerning ethanol fermentation conducted with the use of a glucose substrate, and the effects on ethanol fermentation conducted with the use of a xylose substrate, which is inhibited by acetic acid at a significant level, remain unknown. Even if the mutant yeast strains reported in such literatures were used, the amount of acetic acid carry-over, which would be problematic at the time of the reuse of fermenting microorganisms or continuous fermentation, would not be reduced. Even if the ethanol fermentation ability is improved in the presence of acetic acid, in addition, it is necessary that acetic acid contained in the medium be metabolized and degraded. Otherwise, the amount of acetic acid would be increased because of the presence of acetic acid produced by the yeast strain, as the reuse of microorganisms is repeated.

Alternatively, inhibition of fermentation by acetic acid may be avoided by metabolization of acetic acid in a medium simultaneously with ethanol fermentation. However, acetic acid metabolism is an aerobic reaction, which overlaps the metabolic pathway of ethanol. While acetic acid metabolism may be achieved by conducting fermentation under aerobic conditions, accordingly, ethanol as a target substance would also be metabolized.

As a means for metabolizing acetic acid under anaerobic conditions in which ethanol is not metabolized, assimilation of acetic acid achieved by introduction of the mhpF gene encoding acetaldehyde dehydrogenase (EC 1.2.1.10) into a *Saccharomyces cerevisiae* strain in which the GPD1 and GPD2 genes of the pathway of glycerin production had been destroyed has been reported (Appl. Environ. Microbiol., 2010, 76: 190-195, WO 2011/010923, Appl. Environ. Microbiol., 2015, 81: 8108-8117, WO 2011/140386, and WO 2014/074895). Acetaldehyde dehydrogenase catalyzes the reversible reaction described below.

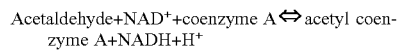

The pathway of glycerin production mediated by the GPD1 and GPD2 genes is a pathway that oxidizes excessive coenzyme NADH resulting from metabolism into $NAD^+$, as shown in the following chemical reaction.

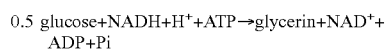

The reaction pathway is destructed by disrupting the GPD1 and GPD2 genes, excessive coenzyme NADH is supplied through introduction of mhpF, and the reaction proceeds as shown below.

Acetyl coenzyme A is synthesized from acetic acid by acetyl-CoA synthetase, and acetaldehyde is converted into ethanol. Eventually, excessive coenzyme NADH is oxidized and acetic acid is metabolized, as shown in the following chemical reaction.

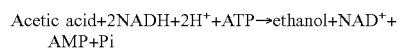

As described above, it is necessary to destroy the glycerin pathway in order to impart acetic acid metabolizing ability to a yeast strain. However, the GPD1- and GPD2-disrupted strain is known to have significantly lowered fermentation ability, and utility at the industrial level is low. Neither Appl. Environ. Microbiol., 2010 76: 190-195 nor WO 2011/010923 concerns the xylose-assimilating yeast strain, and, accordingly, whether or not the strain of interest would be effective at the time of xylose assimilation is unknown.

Instead of disruption of the GPD1 and GPD2 genes, the xylose reductase (XR) and the xylitol dehydrogenase (XDH) genes constituting the metabolic pathway of xylose are introduced to induce an oxidation-reduction imbalance in the cells due to coenzyme dependency between XR and XDH. Thus, excessive coenzyme NADH is supplied (Nat. Commun., 2013; 4: 2580). Specifically, XR mainly uses NADPH as a coenzyme when converting xylose into xylitol (conversion of NADPH into NADP$^+$). In contrast, XDH uses NAD$^+$ as a coenzyme when converting xylitol into xylulose (conversion of NAD$^+$ into NADH). Thus, the imbalance is present in terms of coenzyme requirements between these enzymes, and NADH is accumulated. As a result of ethanol fermentation from xylose in yeast strains into which XR and XDH had been introduced, however, an intermediate metabolite (i.e., xylitol) is accumulated. While acetic acid is metabolized, an ethanol yield from carbohydrate is poor. Accordingly, introduction of such enzymes is not practical.

A strain resulting from introduction of the mhpF gene into a strain that was not subjected to GPD1 or GPD2 gene disruption has also been reported (Biotechnol. Lett., 2011, 33: 1375-1380). While Biotechnol. Lett., 2011, 33: 1375-1380 reports that the amount of acetic acid production is reduced upon introduction of the mhpF gene, it does not report that acetic acid in the medium would be reduced. In addition, Biotechnol. Lett., 2011, 33: 1375-1380 does not relate to a xylose-assimilating yeast strain.

Also, there are reports concerning a xylose-assimilating yeast strain resulting from introduction of a xylose isomerase (XI) gene (derived from the intestinal protozoa of termites) (JP 2011-147445 A) and a strain resulting from further introduction of the acetaldehyde dehydrogenase gene (derived from *Bifidobacterium adolescentis*) into a xylose-assimilating yeast strain comprising a XI gene (derived from *Piromyces* sp. E2) introduced thereinto (JP 2010-239925 A), although the above literature does not report acetic acid assimilation at the time of xylose assimilation.

Meanwhile, the NDE1 gene and the NDE2 gene encode NADH dehydrogenases for reoxidation of cytoplasmic NADH on the mitochondrial outer membrane of the cells. Concerning the NDE1 gene and the NDE2 gene, NDE gene suppression is reported to improve the productivity of lactic acid (US 2015/0024444), xylitol (US 2005/0148055 A1), and isobutanol (WO 2014/004616 A2) produced by yeast cells.

According to conventional techniques, as described above, acetic acid would not be efficiently metabolized or degraded under conditions in which ethanol fermentation and xylose assimilation take place simultaneously. WO 2014/133092 A1 discloses a technique for imparting acetic acid metabolizing ability to a recombinant yeast strain having xylose-metabolizing ability by introducing a particular acetaldehyde dehydrogenase gene thereinto. However, it was difficult for the recombinant yeast strain disclosed in WO 2014/133092 A1 to efficiently metabolize acetic acid accumulated in the medium.

SUMMARY

Under the above circumstances, in particular, the present disclosure relates to improving acetic acid metabolizing ability of a recombinant yeast strain having xylose-metabolizing ability and providing a method for producing ethanol using a recombinant yeast strain with an excellent acetic acid metabolizing ability.

As a result of concentrated studies conducted by the inventors of the present disclosure, suppression of a gene encoding NADH dehydrogenase involved in reoxidation of cytoplasmic NADH on the mitochondrial outer membrane was found to improve acetic acid metabolic ability in the recombinant yeast strain resulting from introduction of a particular acetaldehyde dehydrogenase gene into a yeast strain having a xylose-metabolizing ability. This has led to the completion of the present disclosure.

The present disclosure includes the following.

(1) A recombinant yeast strain having xylose-metabolizing ability comprising the acetaldehyde dehydrogenase gene introduced thereinto, wherein a gene encoding NADH dehydrogenase involved in reoxidation of cytoplasmic NADH on the mitochondrial outer membrane is suppressed.

(2) The recombinant yeast strain according to (1), wherein the gene encoding NADH dehydrogenase encodes a protein (a) or (b) below:

(a) a protein comprising the amino acid sequence as shown in SEQ ID NO: 2 or 4; or (b) a protein comprising an amino acid sequence exhibiting 70% or higher identity with the amino acid sequence as shown in SEQ ID NO: 2 or 4 and having enzymatic activity of catalyzing a reaction of converting NADH into NAD$^+$.

(3) The recombinant yeast strain according to (1) comprising a xylose isomerase gene introduced thereinto.

(4) The recombinant yeast strain according to (3), wherein the xylose isomerase gene encodes a protein (a) or (b) below:

(a) a protein comprising the amino acid sequence as shown in SEQ ID NO: 6; or (b) a protein comprising an amino acid sequence exhibiting 70% or higher identity with the amino acid sequence as shown in SEQ ID NO: 6 and having enzymatic activity of converting xylose into xylulose.

(5) The recombinant yeast strain according to (1), which further comprises a xylulokinase gene introduced thereinto.

(6) The recombinant yeast strain according to (1), which comprises a gene encoding an enzyme selected from a group of enzymes constituting a non-oxidative process in the pentose phosphate pathway introduced thereinto.

(7) The recombinant yeast strain according to (6), wherein the group of enzymes constituting a non-oxidative process in the pentose phosphate pathway includes ribose-5-phosphate isomerase, ribulose-5-phosphate-3-epimerase, transketolase, and transaldolase.

(8) The recombinant yeast strain according to (1), which allows high-level expression of the alcohol dehydrogenase gene having activity of converting acetaldehyde into ethanol.

(9) The recombinant yeast strain according to (1), which shows a lowered expression level of the alcohol dehydrogenase gene having activity of converting ethanol into acetaldehyde.

(10) A method for producing ethanol comprising a step of culturing the recombinant yeast strain according to any of (1) to (9) in a xylose-containing medium to perform ethanol fermentation.

(11) The method for producing ethanol according to (10), wherein the medium contains cellulose and the ethanol fermentation proceeds simultaneously with saccharification by at least the cellulose.

Effects

The recombinant yeast strain of the present disclosure has excellent acetic acid metabolizing activity. Accordingly, it can lower the concentration of acetic acid in the medium. According to the method for producing ethanol with the use of the recombinant yeast strain of the present disclosure, acetic acid concentration in a medium can be lowered, and inhibition of fermentation caused by acetic acid can be effectively avoided. As a result, the method for producing ethanol of the present disclosure is capable of maintaining high efficiency for ethanol fermentation performed with the use of xylose as a saccharide source and achieving excellent ethanol yield. Accordingly, the method for producing ethanol of the present disclosure enables reduction of the amount of acetic acid carry-over at the time of, for example, reuse of the recombinant yeast strain or use thereof for continuous culture, thereby allowing maintenance of an excellent ethanol yield.

BRIEF DESCRIPTION OF THE DRAWINGS

FIG. 1 is a characteristic diagram showing the results of measurement of acetic acid concentration and ethanol concentration in a medium with the use of the mutant strain resulting from NADH dehydrogenase gene suppression and a control strain prepared in the examples.

DETAILED DESCRIPTION

Hereafter, the present disclosure is described in greater detail with reference to the drawings and the examples.

A recombinant yeast strain used in the method for producing ethanol of the present disclosure has a xylose-metabolizing ability and comprises the acetaldehyde dehydrogenase gene introduced thereinto, which results from suppression of a gene encoding NADH dehydrogenase involved in reoxidation of cytoplasmic NADH on the mitochondrial outer membrane. The recombinant yeast strain of the present disclosure can metabolize acetic acid contained in a medium. According to the method for producing ethanol using the recombinant yeast strain of the present disclosure, accordingly, acetic acid concentration in a medium is lowered as ethanol fermentation proceeds.

<Recombinant Yeast Strain>

A recombinant yeast strain used in the method for producing ethanol of the present disclosure has xylose-metabolizing ability, which results from introduction of the acetaldehyde dehydrogenase gene and suppression of a gene encoding NADH dehydrogenase involved in reoxidation of cytoplasmic NADH on the mitochondrial outer membrane (hereafter, it is referred to as the "NADH dehydrogenase gene"). The term "yeast strain having xylose-metabolizing ability" refers to: a yeast strain to which xylose-metabolizing ability has been imparted as a result of introduction of a xylose metabolism-associated gene into a yeast strain that does not inherently has xylose-metabolizing ability; and a yeast strain inherently comprising a xylose metabolism-associated gene and having xylose-metabolizing ability. More specifically, a yeast strain having xylose-metabolizing ability can be a yeast strain to which xylose-metabolizing ability has been imparted as a result of introduction of a xylose isomerase gene into a yeast strain that does not inherently have xylose-metabolizing ability or a yeast strain to which xylose-metabolizing ability has been imparted as a result of introduction of another xylose metabolism-associated gene.

In the recombinant yeast strain of the present disclosure, the NADH dehydrogenase gene is suppressed. When the NADH dehydrogenase gene is to be suppressed, a yeast strain is modified to show a lowered expression level of the NADH dehydrogenase gene. The NADH dehydrogenase gene is not particularly limited, and examples thereof include the NDE1 gene and the NDH2 gene of *Saccharomyces cerevisiae*. SEQ ID NO: 1 and SEQ ID NO: 2 show the nucleotide sequence of the coding region of the NDE1 gene and the amino acid sequence of a protein encoded by such gene, respectively. Also, SEQ ID NO: 3 and SEQ ID NO: 4 show the nucleotide sequence of the coding region of the NDE2 gene and the amino acid sequence of a protein encoded by such gene, respectively.

The NADH dehydrogenase genes are not limited to the genes identified by SEQ ID NOs: 1 to 4. It may be a paralogous gene or a homologous gene in the narrow sense having different nucleotide and amino acid sequences.

The NADH dehydrogenase genes are not limited to the genes identified by SEQ ID NOs: 1 to 4. For example, it may be a gene comprising an amino acid sequence having 70% or higher, preferably 80% or higher, more preferably 90% or higher, and most preferably 95% or higher sequence similarity to or identity with the amino acid sequence as shown in SEQ ID NO: 2 or 4 and encoding a protein having NADH dehydrogenase activity (i.e., an activity of catalyzing a reaction of converting NADH into $NAD^+$). The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by the amino acid residues.

Further, the NADH dehydrogenase genes are not limited to the genes identified by SEQ ID NOs: 1 to 4. For example, it may be a gene comprising an amino acid sequence derived from the amino acid sequence as shown in SEQ ID NO: 2 or 4 by substitution, deletion, insertion, or addition of one or several amino acids and encoding a protein having NADH dehydrogenase activity (i.e., an activity of catalyzing a reaction of converting NADH into $NAD^+$). The term "several" used herein refers to, for example, 2 to 50, preferably 2 to 30, more preferably 2 to 15, and most preferably 2 to 7.

Furthermore, the NADH dehydrogenase genes are not limited to the genes identified by SEQ ID NOs: 1 to 4. For example, it may be a gene hybridizing under stringent conditions to the full-length sequence or a partial sequence of a complementary strand of DNA comprising the nucleotide sequence as shown in SEQ ID NO: 1 or 3 and encoding a protein having NADH dehydrogenase activity (i.e., an activity of catalyzing a reaction of converting NADH into $NAD^+$). Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42° C. to 68° C. and preferably 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 1 or 3 or a gene encoding an amino acid sequence that differs from the sequence as shown in SEQ ID NO: 2 or 4 would function as the NADH dehydrogenase gene may be determined by, for example, preparing an expression vector comprising the gene of interest incorporated into an adequate site between a promoter and a terminator, transforming an *E. coli* host using such expression vector, and assaying the NADH dehydrogenase activity (i.e., an activity of catalyzing a reaction of converting NADH into $NAD^+$) of the protein expressed. The term "NADH dehydrogenase activity" is synonymous with "oxidoreductase activity" of transferring 2 electrons from NADH to ubiquinone (CoQ). NADH dehydrogenase catalyzes a reaction of converting NADH and decyl ubiquinone into $NAD^+$ and decyl ubiquinol, respectively. Accordingly, the NADH dehydrogenase activity can be evaluated based on, for example, the amount of NADH decrease determined based on a change in the absorbance at 340 nm.

The recombinant yeast strain of the present disclosure has xylose-metabolizing ability; that is, it is capable of assimilating xylose contained in a medium to produce ethanol. Xylose contained in a medium may be obtained by saccharification of xylan or hemicellulose comprising xylose as a constituent sugar. Alternatively, it may be supplied to a medium as a result of saccharification of xylan or hemicellulose contained in a medium by a saccharification-enzyme. The latter case refers to the so-called simultaneous saccharification and fermentation process.

Examples of yeast strains having xylose-metabolizing ability include a yeast strain to which xylose-metabolizing ability has been imparted as a result of introduction of a xylose isomerase gene into a yeast strain that does not inherently has xylose-metabolizing ability and a yeast strain to which xylose-assimilating ability has been imparted as a result of introduction of another xylose assimilation-associated gene.

The xylose isomerase gene (the XI gene) is not particularly limited, and a gene originating from any organism species may be used. For example, a plurality of the xylose isomerase genes derived from the intestinal protozoa of termites disclosed in JP 2011-147445 A can be used without particular limitation. Examples of the xylose isomerase genes that can be used include a gene derived from the anaerobic fungus *Piromyces* sp. strain E2 (JP 2005-514951 A), a gene derived from the anaerobic fungus *Cyllamyces aberensis*, a gene derived from a bacterial strain (i.e., *Bacteroides thetaiotaomicron*), a gene derived from a bacterial strain (i.e., *Clostridium phytofermentans*), and a gene derived from the *Streptomyces murinus* cluster.

Specifically, use of a xylose isomerase gene derived from the intestinal protozoa of *Reticulitermes speratus* as the xylose isomerase gene is preferable. The nucleotide sequence of the coding region of the xylose isomerase gene derived from the intestinal protozoa of *Reticulitermes spera-* *tus* and the amino acid sequence of a protein encoded by such gene are as shown in SEQ ID NOs: 5 and 6, respectively.

The xylose isomerase genes are not limited to the genes identified by SEQ ID NO: 5 and SEQ ID NO: 6. It may be a paralogous gene or a homologous gene in the narrow sense having different nucleotide and amino acid sequences.

The xylose isomerase genes are not limited to the genes identified by SEQ ID NO: 5 and SEQ ID NO: 6. For example, it may be a gene comprising an amino acid sequence having 70% or higher, preferably 80% or higher, more preferably 90% or higher, and most preferably 95% or higher sequence similarity to or identity with the amino acid sequence as shown in SEQ ID NO: 6 and encoding a protein having xylose isomerase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the xylose isomerase genes are not limited to the genes identified by SEQ ID NO: 5 and SEQ ID NO: 6. For example, it may be a gene comprising an amino acid sequence derived from the amino acid sequence as shown in SEQ ID NO: 6 by substitution, deletion, insertion, or addition of one or several amino acids and encoding a protein having xylose isomerase activity. The term "several" used herein refers to, for example, 2 to 30, preferably 2 to 20, more preferably 2 to 10, and most preferably 2 to 5.

Furthermore, the xylose isomerase genes are not limited to the genes identified by SEQ ID NO: 5 and SEQ ID NO: 6. For example, it may be a gene hybridizing under stringent conditions to the full-length sequence or a partial sequence of a complementary strand of DNA comprising the nucleotide sequence as shown in SEQ ID NO: 5 and encoding a protein having xylose isomerase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42° C. to 68° C. and preferably 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 5 or a gene encoding an amino acid sequence that differs from the sequence as shown in SEQ ID NO: 6 would function as a xylose isomerase gene may be determined by, for example, preparing an expression vector comprising the gene of interest incorporated into an adequate site between a promoter and a terminator, transforming an *E. coli* host using such expression vector, and assaying the xylose isomerase activity of the protein expressed. The term "xylose isomerase activity" refers to activity of isomerizing xylose into xylulose. Accordingly, xylose isomerase activity can be evaluated by preparing a xylose-containing solution as a substrate, allowing the target protein to react at an adequate temperature, and measuring the amount of xylose that has decreased and/or the amount of xylulose that has been generated.

It is particularly preferable to use, as a xylose isomerase gene, a gene comprising an amino acid sequence resulting from introduction of a particular mutation into a particular amino acid residue in the amino acid sequence as shown in SEQ ID NO: 6 and encoding mutant xylose isomerase with improved xylose isomerase activity. A specific example of a gene encoding mutant xylose isomerase is a gene encoding an amino acid sequence resulting from substitution of asparagine with cysteine at position 337 in the amino acid sequence as shown in SEQ ID NO: 6. Xylose isomerase activity of such mutant xylose isomerase is superior to that of wild-type xylose isomerase. In addition, mutant xylose isomerase is not limited to the xylose isomerase resulting from substitution of asparagine with cysteine at position 337. It may be xylose isomerase resulting from substitution of asparagine at position 337 with an amino acid other than cysteine, xylose isomerase resulting from substitution of asparagine at position 337 and another amino acid with other amino acids, or xylose isomerase resulting from substitution of an amino acid other than cysteine at position 337.

Meanwhile, examples of xylose metabolism-associated genes other than the xylose isomerase gene include a xylose reductase gene encoding a xylose reductase that converts xylose into xylitol, a xylitol dehydrogenase gene encoding a xylitol dehydrogenase that converts xylitol into xylulose, and a xylulokinase gene encoding a xylulokinase that phosphorylates xylulose to produce xylulose 5-phosphate. Xylulose 5-phosphate produced by a xylulokinase enters the pentose phosphate pathway, and it is then metabolized therein.

Examples of xylose metabolism-associated genes include, but are not particularly limited to, a xylose reductase gene and a xylitol dehydrogenase gene derived from *Pichia stipitis* and a xylulokinase gene derived from *Saccharomyces cerevisiae* (see Eliasson A. et al., Appl. Environ. Microbiol., 66: 3381-3386; and Toivari M. N. et al., Metab. Eng., 3: 236-249). In addition, xylose reductase genes derived from *Candida tropicalis* and *Candida prapsilosis*, xylitol dehydrogenase genes derived from *Candida tropicalis* and *Candida prapsilosis*, and a xylulokinase gene derived from *Pichia stipitis* can be used.

Examples of yeast strains that inherently have xylose-metabolizing ability include, but are not particularly limited to, *Pichia stipitis, Candida tropicalis*, and *Candida prapsilosis*.

An acetaldehyde dehydrogenase gene to be introduced into a yeast strain having xylose-metabolizing ability is not particularly limited, and a gene derived from any organism species may be used. When acetaldehyde dehydrogenase genes derived from organisms other than a fungus such as yeast (e.g., genes derived from bacteria, animals, plants, insects, or algae) are used, it is preferable that the nucleotide sequence of the gene be modified in accordance with the frequency of codon usage in a yeast strain into which the gene of interest is to be introduced.

More specifically, the mhpF gene of *E. coli* or the ALDH1 gene of *Entamoeba histolytica* as disclosed in Applied and Environmental Microbiology, May 2004, pp. 2892-2897, Vol. 70, No. 5 can be used as the acetaldehyde dehydrogenase genes. The nucleotide sequence of the mhpF gene of *E. coli* and the amino acid sequence of a protein encoded by the mhpF gene are shown in SEQ ID NOs: 7 and 8, respectively.

The acetaldehyde dehydrogenase genes are not limited to the genes identified by SEQ ID NOs: 7 and 8. It may be a paralogous gene or a homologous gene in the narrow sense having different nucleotide and amino acid sequences as long as it encodes an enzyme defined with EC No. 1.2.1.10. Examples of the acetaldehyde dehydrogenase genes include an adhE gene of *E. coli*, an acetaldehyde dehydrogenase gene derived from *Clostridium beijerinckii*, and an acetaldehyde dehydrogenase gene derived from *Chlamydomonas reinhardtii*. Here, the nucleotide sequence of the adhE gene of *E. coli* and the amino acid sequence of a protein encoded by the adhE gene are as shown in SEQ ID NOs: 9 and 10, respectively.

The acetaldehyde dehydrogenase genes are not limited to the genes identified by SEQ ID NOs: 7, 8, 9, and 10. For example, it may be a gene comprising an amino acid sequence having 70% or higher, preferably 80% or higher, more preferably 90% or higher, and most preferably 95% or higher sequence similarity to or identity with the amino acid sequence as shown in SEQ ID NO: 8 or 10 and encoding a protein having acetaldehyde dehydrogenase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the acetaldehyde dehydrogenase genes are not limited to the genes identified by SEQ ID NOs: 7, 8, 9, and 10. For example, it may be a gene comprising an amino acid sequence derived from the amino acid sequence as shown in SEQ ID NO: 8 or 10 by substitution, deletion, insertion, or addition of one or several amino acids and encoding a protein having acetaldehyde dehydrogenase activity. The term "several" used herein refers to, for example, 2 to 30, preferably 2 to 20, more preferably 2 to 10, and most preferably 2 to 5.

Furthermore, the acetaldehyde dehydrogenase genes are not limited to the genes identified by SEQ ID NOs: 7, 8, 9, and 10. For example, it may be a gene hybridizing under stringent conditions to the full-length sequence or a partial sequence of a complementary strand of DNA comprising the nucleotide sequence as shown in SEQ ID NO: 7 or 9 and encoding a protein having acetaldehyde dehydrogenase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42° C. to 68° C. and preferably 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 7 or 9 or a gene encoding an amino acid sequence that differs from the sequence as shown in SEQ ID NO: 8 or 10 would function as the acetaldehyde dehydrogenase gene may be determined by, for example, preparing an expression vector comprising the gene of interest incorporated into an adequate site between a promoter and a terminator, transforming an E. coli host using such expression vector, and assaying the acetaldehyde dehydrogenase of the protein expressed. Acetaldehyde dehydrogenase activity can be assayed by preparing a solution containing acetaldehyde, CoA, and NAD⁺ as substrates, allowing the target protein to react at adequate temperature, and converting the generated acetyl phosphate into acetyl phosphate with the aid of a phosphate acetyl transferase or spectroscopically assaying the generated NADH.

The recombinant yeast strain of the present disclosure may further comprise other gene(s) introduced thereinto, and such other gene(s) are not particularly limited. For example, a gene involved in the sugar metabolism of glucose may be introduced into such recombinant yeast strain. For example, a recombinant yeast strain can have β-glucosidase activity resulting from the introduction of the β-glucosidase gene.

The term "β-glucosidase activity" used herein refers to the activity of catalyzing a hydrolysis reaction of a β-glycoside bond of a sugar. Specifically, β-glucosidase is capable of degrading a cellooligosaccharide, such as cellobiose, into glucose. The β-glucosidase gene can be introduced in the form of a cell-surface display gene. The term "cell-surface display gene" used herein refers to a gene that is modified to display a protein to be encoded by the gene on a cell surface. For example, a cell-surface display β-glucosidase gene is a gene resulting from fusion of a 3-glucosidase gene with a cell-surface localized protein gene. A cell-surface localized protein is fixed and present on a yeast cell surface layer. Examples include agglutinative proteins, such as α- or a-agglutinin and FLO proteins. In general, a cell-surface localized protein comprises an N-terminal secretory signal sequence and a C-terminal GPI anchor attachment recognition signal. While a cell-surface localized protein shares properties with a secretory protein in terms of the presence of a secretory signal, its secretory signal differs in that the cell-surface localized protein is transported while fixed to a cell membrane through a GPI anchor. When a cell-surface localized protein passes through a cell membrane, a GPI anchor attachment recognition signal sequence is selectively cut, it binds to a GPI anchor at a newly protruded C-terminal region, and it is then fixed to the cell membrane. Thereafter, the root of the GPI anchor is cut by phosphatidylinositol-dependent phospholipase C (PI-PLC). Subsequently, a protein separated from the cell membrane is integrated into a cell wall, fixed onto a cell surface layer, and then localized on a cell surface layer (see, for example, JP 2006-174767 A).

The β-glucosidase gene is not particularly limited, and an example is a β-glucosidase gene derived from Aspergillus aculeatus (Mural, et al., Appl. Environ. Microbiol., 64: 4857-4861). In addition, a β-glucosidase gene derived from Aspergillus oryzae, a β-glucosidase gene derived from Clostridium cellulovorans, and a β-glucosidase gene derived from Saccharomycopsis fibligera can be used.

In addition to or other than the β-glucosidase gene, a gene encoding another cellulase-constituting enzyme may have been introduced into a recombinant yeast strain used in the method for producing ethanol of the present disclosure. Examples of cellulase-constituting enzymes other than β-glucosidase include exo-cellobiohydrolases that liberate cellobiose from the terminus of crystalline cellulose (CBH1 and CBH2) and endo-glucanase (EG) that cannot degrade crystalline cellulose but cleaves a non-crystalline cellulose (amorphous cellulose) chain at random.

Examples of other genes to be introduced into a recombinant yeast strain include an alcohol dehydrogenase gene (the ADH1 gene) having activity of converting acetaldehyde into ethanol, an acetyl-CoA synthetase gene (the ACS1 gene) having activity of converting acetic acid into acetyl-CoA, and genes having activity of converting acetaldehyde into acetic acid (i.e., the ALD4, ALD5, and ALD6 genes). The alcohol dehydrogenase gene (the ADH2 gene) having activity of converting ethanol into acetaldehyde may be disrupted.

In addition, it is preferable that a recombinant yeast strain used in the method for producing ethanol of the present disclosure allow high-level expression of the alcohol dehydrogenase gene (the ADH1 gene) having activity of converting acetaldehyde into ethanol. In order to realize high-level expression of such gene, for example, a promoter of the inherent gene may be replaced with a promoter intended for high-level expression, or an expression vector enabling expression of such gene may be introduced into a yeast strain.

The nucleotide sequence of the ADH1 gene of Saccharomyces cerevisiae and the amino acid sequence of a protein encoded by such gene are shown in SEQ ID NOs: 11 and 12, respectively. The alcohol dehydrogenase gene to be expressed at high level is not limited to the genes identified by SEQ ID NOs: 11 and 12. It may be a paralogous gene or a homologous gene in the narrow sense having different nucleotide and amino acid sequences.

The alcohol dehydrogenase genes are not limited to the genes identified by SEQ ID NOs: 11 and 12. For example, it may be a gene comprising an amino acid sequence having 70% or higher, preferably 80% or higher, more preferably 90% or higher, and most preferably 95% or higher sequence similarity to or identity with the amino acid sequence as shown in SEQ ID NO: 12 and encoding a protein having alcohol dehydrogenase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the alcohol dehydrogenase genes are not limited to the genes identified by SEQ ID NOs: 11 and 12. For example, it may be a gene comprising an amino acid sequence derived from the amino acid sequence as shown in SEQ ID NO: 12 by substitution, deletion, insertion, or addition of one or several amino acids and encoding a protein having alcohol dehydrogenase. The term "several" used herein refers to, for example, 2 to 30, preferably 2 to 20, more preferably 2 to 10, and most preferably 2 to 5.

Furthermore, the alcohol dehydrogenase genes are not limited to the genes identified by SEQ ID NOs: 11 and 12. For example, it may be a gene hybridizing under stringent conditions to the full-length sequence or a partial sequence of a complementary strand of DNA comprising the nucleotide sequence as shown in SEQ ID NO: 11 and encoding a protein having alcohol dehydrogenase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42° C. to 68° C. and preferably 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 11 or a gene encoding an amino acid sequence that differs from the sequence as shown in SEQ ID NO: 12 would function as the alcohol dehydrogenase gene having activity of converting acetaldehyde into ethanol may be determined by, for example, preparing an expression vector comprising the gene of interest incorporated into an adequate site between a promoter and a terminator, transforming an yeast host using such expression vector, and assaying the alcohol dehydrogenase activity of the protein expressed. Alcohol dehydrogenase activity of converting acetaldehyde into ethanol can be assayed by preparing a solution containing aldehyde and NADH or NADPH as substrates, allowing the target protein to react at adequate temperature, and assaying the generated alcohol or spectroscopically assaying $NAD^+$ or $NADP^+$.

A recombinant yeast strain used in the method for producing ethanol of the present disclosure is preferably characterized by a lowered expression level of the alcohol dehydrogenase gene (the ADH2 gene) having activity of converting ethanol into aldehyde. In order to lower the expression level of such gene, a promoter of the inherent gene of interest may be modified, or such gene may be deleted. In order to delete the gene, either or both of a pair of ADH2 genes present in diploid recombinant yeast may be deleted. Examples of techniques for suppressing gene expression include the transposon technique, the transgene technique, post-transcriptional gene silencing, the RNAi technique, the nonsense mediated decay (NMD) technique, the ribozyme technique, the anti-sense technique, the miRNA (micro-RNA) technique, and the siRNA (small interfering RNA) technique.

The nucleotide sequence of the ADH2 gene of *Saccharomyces cerevisiae* and the amino acid sequence of a protein encoded by such gene are shown in SEQ ID NOs: 13 and 14, respectively. The target alcohol dehydrogenase genes are not limited to the genes identified by SEQ ID NOs: 13 and 14. It may be a paralogous gene or a homologous gene in the narrow sense having different nucleotide and amino acid sequences.

Also, the alcohol dehydrogenase genes are not limited to the genes identified by SEQ ID NOs: 13 and 14. For example, it may be a gene comprising an amino acid sequence having 70% or higher, preferably 80% or higher, more preferably 90% or higher, and most preferably 95% or higher sequence similarity to or identity with the amino acid sequence as shown in SEQ ID NO: 14 and encoding a protein having alcohol dehydrogenase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the alcohol dehydrogenase genes are not limited to the genes identified by SEQ ID NOs: 13 and 14. For example, it may be a gene comprising an amino acid sequence derived from the amino acid sequence as shown in SEQ ID NO: 14 by substitution, deletion, insertion, or addition of one or several amino acids and encoding a protein having alcohol dehydrogenase activity. The term "several" used herein refers to, for example, 2 to 30, preferably 2 to 20, more preferably 2 to 10, and most preferably 2 to 5.

Furthermore, the alcohol dehydrogenase genes are not limited to the genes identified by SEQ ID NOs: 13 and 14. For example, it may be a gene hybridizing under stringent conditions to the full-length sequence or a partial sequence of a complementary strand of DNA comprising the nucleotide sequence as shown in SEQ ID NO: 13 and encoding a protein having alcohol dehydrogenase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42° C. to 68° C. and preferably 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 13 or a gene encoding an amino acid sequence that differs from the sequence as shown in SEQ ID NO: 14 would function as the alcohol dehydrogenase gene having activity of converting ethanol into aldehyde may be determined by, for example, preparing an expression vector comprising the gene of interest incorporated into an adequate site between a promoter and a terminator, transforming an yeast host using such expression vector, and assaying the alcohol dehydrogenase activity of the protein expressed. Alcohol dehydrogenase activity of converting ethanol into aldehyde can be assayed by preparing a solution containing alcohol and NAD⁺ or NADP⁺ as substrates, allowing the target protein to react at adequate temperature, and assaying the generated aldehyde or spectroscopically assaying NADH or NADPH.

Further examples of other genes that can be introduced into a recombinant yeast strain include genes associated with the metabolic pathway of L-arabinose, which is a pentose contained in hemicellulose constituting a biomass. Examples of such genes include an L-arabinose isomerase gene, an L-ribulokinase gene, and an L-ribulose-5-phosphate-4-epimerase gene derived from prokaryotes and an L-arabitol-4-dehydrogenase gene and an L-xylose reductase gene derived from eukaryotes.

In particular, an example of another gene to be introduced into a recombinant yeast strain is a gene capable of promoting the use of xylose in a medium. A specific example thereof is a gene encoding xylulokinase having activity of generating xylulose-5-phosphate using xylose as a substrate. The metabolic flux of the pentose phosphate pathway can be improved through the introduction of the xylulokinase gene.

Further, a gene encoding an enzyme selected from the group of enzymes constituting a non-oxidative process in the pentose phosphate pathway can be introduced into a recombinant yeast strain. Examples of enzymes constituting a non-oxidative process in the pentose phosphate pathway include ribose-5-phosphate isomerase, ribulose-5-phosphate-3-epimerase, transketolase, and transaldolase. It is preferable that one or more genes encoding such enzymes be introduced. It is more preferable that two or more such genes be introduced in combination, further preferable that three or more genes in combination be introduced, and the most preferable that all of the genes above be introduced.

More specifically, the xylulokinase (XK) gene of any origin can be used without particular limitation. A wide variety of microorganisms, such as bacterial and yeast strains, which assimilate xylulose, possess the XK gene. Information concerning XK genes can be obtained by searching the website of NCBI or other institutions, according to need. Preferable examples of such genes include the XK genes derived from yeast strains, lactic acid bacteria, E. coli bacteria, and plants. An example of an XK gene is XKS1, which is an XK gene derived from the S. cerevisiae S288C strain (GenBank: Z72979) (the nucleotide sequence and the amino acid sequence in the CDS coding region).

More specifically, a transaldolase (TAL) gene, a transketolase (TKL) gene, a ribulose-5-phosphate epimerase (RPE) gene, and a ribose-5-phosphate ketoisomerase (RKI) gene of any origin can be used without particular limitation. A wide variety of organisms comprising the pentose phosphate pathway possess such genes. For example, a common yeast strain such as S. cerevisiae possesses such genes. Information concerning such genes can be obtained from the website of NCBI or other institutions, according to need. Genes belonging to the same genus as the host eukaryotic cells, such as eukaryotic or yeast cells, are preferable, and genes originating from the same species as the host eukaryotic cells are more preferable. A TAL1 gene, a TKL1 gene and a TKL2 gene, an RPE1 gene, and an RKI gene can be preferably used as the TAL gene, the TKL genes, the RPE gene, and the RKI gene, respectively. Examples of such genes include a TAL1 gene derived from the S. cerevisiae S288 strain (GenBank: U19102), a TKL1 gene derived from the S. cerevisiae S288 strain (GenBank: X73224), an RPE1 gene derived from the S. cerevisiae S288 strain (GenBank: X83571), and an RKI1 gene derived from the S. cerevisiae S288 strain (GenBank: Z75003).

<Production of Recombinant Yeast Strain>

The recombinant yeast strain of the present disclosure can be produced by, for example, introducing the acetaldehyde dehydrogenase gene and the xylose metabolism-associated gene into a yeast strain having no xylose-metabolizing ability and modifying the yeast strain to lower the NADH dehydrogenase gene expression level in the yeast genome. Alternatively, the recombinant yeast strain of the present disclosure can be produced by, for example, introducing the acetaldehyde dehydrogenase gene into a yeast strain having xylose-metabolizing ability and disrupting the NADH dehydrogenase gene in the yeast genome. When producing the recombinant yeast strain of the present disclosure, other genes described above may be introduced into a yeast strain, or the recombinant yeast strain may be modified to lower the expression level of the alcohol dehydrogenase gene (the ADH2 gene) having activity of converting ethanol into aldehyde.

In order to lower the expression level of, for example, the NADH dehydrogenase gene, a promoter of the inherent gene of interest may be modified, or such gene may be deleted. In order to delete the gene, either or both of a pair of genes present in diploid recombinant yeast may be deleted. Examples of techniques for suppressing gene expression include the transposon technique, the transgene technique, post-transcriptional gene silencing, the RNAi technique, the nonsense mediated decay (NMD) technique, the ribozyme technique, the anti-sense technique, the miRNA (microRNA) technique, and the siRNA (small interfering RNA) technique.

When the xylose metabolism-associated gene, the acetaldehyde dehydrogenase gene, and other genes described above are introduced into a yeast strain, such genes may be simultaneously introduced thereinto, or such genes may be successively introduced with the use of different expression vectors.

Examples of host yeast strains that can be used include, but are not particularly limited to, *Candida Shehatae, Pichia stipitis, Pachysolen tannophilus, Saccharomyces cerevisiae*, and *Schizosaccaromyces pombe*, with *Saccharomyces cerevisiae* being particularly preferable. Experimental yeast strains may also be used from the viewpoint of experimental convenience, or industrial (practical) strains may also be used from the viewpoint of practical usefulness. Examples of industrial strains include yeast strains used for the production of wine, sake, and shochu.

Use of a host yeast strain having homothallic properties is preferable. According to the technique disclosed in JP 2009-34036 A, multiple copies of genes can be easily introduced into a genome with the use of a yeast strain having homothallic properties. The term "yeast strain having homothallic properties" has the same meaning as the term "homothallic yeast strain." Yeast strains having homothallic properties are not particularly limited, and any yeast strains can be used. An example of a yeast strain having homothallic properties is, but is not limited to, the *Saccharomyces cerevisiae* OC-2 train (NBRC2260). Examples of other yeast strains having homothallic properties include an alcohol-producing yeast (Taiken No. 396, NBRCO216) (reference: "*Alcohol kobo no shotokusei*" ("Various properties of alcohol-producing yeast"), Shuken Kaiho, No. 37, pp. 18-22, 1998.8), an ethanol-producing yeast isolated in Brazil and in Japan (reference: "*Brazil to Okinawa de bunri shita Saccharomyces cerevisiae yaseikabu no idengakuteki seishitsu*" ("Genetic properties of wild-type *Saccharomyces cerevisiae* isolated in Brazil and in Okinawa"), the Journal of the Japan Society for Bioscience, Biotechnology, and Agrochemistry, Vol. 65, No. 4, pp. 759-762, 1991.4), and 180 (reference: "*Alcohol Hakkoryoku no tsuyoi kobo no screening*" ("Screening of yeast having potent alcohol-fermenting ability"), the Journal of the Brewing Society of Japan, Vol. 82, No. 6, pp. 439-443, 1987.6). In addition, the HO gene may be introduced into a yeast strain exhibiting heterothallic phenotypes in an expressible manner, and the resulting strain can be used as a yeast strain having homothallic properties. That is, the term "yeast strain having homothallic properties" used herein also refers to a yeast strain into which the HO gene has been introduced in an expressible manner.

The *Saccharomyces cerevisiae* OC-2 strain is particularly preferable since it has heretofore been used for wine brewing, and the safety thereof has been verified. As described in the examples below, the *Saccharomyces cerevisiae* OC-2 strain is preferable in terms of its excellent promoter activity at high sugar concentrations. In particular, the *Saccharomyces cerevisiae* OC-2 strain is preferable in terms of its excellent promoter activity for the pyruvate decarboxylase gene (PDC1) at high sugar concentrations.

Promoters of genes to be introduced are not particularly limited. For example, promoters of the glyceraldehyde-3-phosphate dehydrogenase gene (TDH3), the 3-phosphoglycerate kinase gene (PGK1), and the high-osmotic pressure response 7 gene (HOR7) can be used. The promoter of the pyruvate decarboxylase gene (PDC1) is particularly preferable in terms of its high capacity for expressing target genes in a downstream region at high levels.

Specifically, such gene may be introduced into the yeast genome together with an expression-regulating promoter or another expression-regulated region. Such gene may be introduced into a host yeast genome in such a manner that expression thereof is regulated by a promoter or another expression-regulated region of a gene that is inherently present therein.

The gene can be introduced into the genome by any conventional technique known as a yeast transformation technique. Specific examples include, but are not limited to, electroporation (Meth. Enzym., 194, p. 182, 1990), the spheroplast technique (Proc. Natl. Acad. Sci., U.S.A., 75, p. 1929, 1978), and the lithium acetate method (J. Bacteriology, 153, p. 163, 1983; Proc. Natl. Acad. Sci., U.S.A., 75, p. 1929, 1978; Methods in yeast genetics, 2000 Edition: A Cold Spring Harbor Laboratory Course Manual).

<Production of Ethanol>

When producing ethanol with the use of the recombinant yeast strain described above, ethanol fermentation is carried out by culture in a medium containing at least xylose. Specifically, a medium in which ethanol fermentation is carried out contains at least xylose as a carbon source. The medium may contain another carbon source, such as glucose, in advance.

Xylose that is contained in a medium to be used for ethanol fermentation can be derived from a biomass. In other words, a medium to be used for ethanol fermentation may comprise a cellulosic biomass and hemicellulase that generates xylose through saccharification of hemicellulose contained in a cellulosic biomass. The cellulosic biomass may have been subjected to a conventional pretreatment technique. Examples of pretreatment techniques include, but are not particularly limited to, degradation of a lignin with a microorganism and grinding of a cellulosic biomass. For example, a ground cellulosic biomass may be subjected to pretreatment, such as soaking thereof in a dilute sulfuric acid solution, alkaline solution, or ionic solution, hydrothermal treatment, or fine grinding. Thus, the efficiency of biomass saccharification can be improved.

When producing ethanol with the use of the recombinant yeast strain described above, the medium may further comprise cellulose and cellulase. In such a case, the medium would contain glucose generated by the action of cellulase upon cellulose. When a medium used for ethanol fermentation contains cellulose, such cellulose can be derived from a biomass. In other words, a medium used for ethanol fermentation may comprise cellulase that is capable of saccharifying cellulase contained in a cellulosic biomass.

A saccharified solution resulting from saccharification of a cellulosic biomass may be added to the medium used for ethanol fermentation. In such a case, the saccharified solution contains remaining cellulose or cellulase and xylose derived from hemicellulose contained in a cellulosic biomass.

As described above, the method for producing ethanol of the present disclosure comprises a step of ethanol fermentation involving the use of at least xylose as a saccharide source. According to the method for producing ethanol of the present disclosure, ethanol can be produced through ethanol fermentation using xylose as a saccharide source. According to the method for producing ethanol with the use of the recombinant yeast strain of the present disclosure, ethanol fermentation is followed by recovery of ethanol from the medium. Ethanol may be recovered by any conventional means without particular limitation. After the completion of the process of ethanol fermentation mentioned above, for example, a liquid layer containing ethanol is separated from a solid layer containing the recombinant yeast strain or solid matter via solid-solution separation. Thereafter, ethanol contained in a liquid layer is separated and purified by distillation, so that highly purified ethanol can be recovered. The degree of ethanol purification can be adequately determined in accordance with the purpose of use of the ethanol.

When producing ethanol with the use of a saccharide derived from a biomass, in general, a fermentation inhibitor, such as acetic acid or furfural, may occasionally be generated in the process of pretreatment or saccharification. In particular, acetic acid is known to inhibit the growth and multiplication of yeast strains and to lower the efficiency for ethanol fermentation conducted with the use of xylose as a saccharide source.

The recombinant yeast strain of the present disclosure, however, is modified to show a lowered expression level of the NADH dehydrogenase gene as described above. It is thus considered that NADH is accumulated in cells. NADH accumulated in cells is used for a reaction for metabolizing and degrading acetic acid by acetaldehyde dehydrogenase. Thus, the recombinant yeast strain of the present disclosure can maintain the acetic acid concentration in a medium at a low level. Accordingly, the method for producing ethanol of the present disclosure can achieve an ethanol yield superior to that achieved with the use of a recombinant yeast strain in which the NADH dehydrogenase gene has not been suppressed.

According to the method for producing ethanol of the present disclosure, acetic acid concentration in a medium remains low after the recombinant yeast strain has been cultured for a given period of time. Even if part of the medium after such given period of time is used for a continuous culture system in which a new culture process is initiated, accordingly, the amount of acetic acid carry-over can be reduced. According to the method for producing ethanol of the present disclosure, therefore, the amount of acetic acid carry-over can be reduced even when cells are recovered and reused after the completion of the process of ethanol fermentation.

The method for producing ethanol of the present disclosure may employ the so-called simultaneous saccharification and fermentation process, in which the step of saccharification of cellulose contained in a medium with a cellulase proceeds simultaneously with the process of ethanol fermentation carried out with the use of saccharide sources (i.e., xylose and glucose generated by saccharification). With the simultaneous saccharification and fermentation process, the step of saccharification of a cellulosic biomass is carried out simultaneously with the process of ethanol fermentation.

Methods of saccharification are not particularly limited, and, for example, an enzymatic method involving the use of a cellulase preparation, such as cellulase or hemicellulase, may be employed. A cellulase preparation contains a plurality of enzymes involved in degradation of a cellulose chain and a hemicellulose chain, and it exhibits a plurality of types of activity, such as endoglucanase activity, endoxylanase activity, cellobiohydrolase activity, glucosidase activity, and xylosidase activity. Cellulase preparations are not particularly limited, and examples include cellulases produced by *Trichoderma reesei* and *Acremonium cellulolyticus*. Commercially available cellulase preparations may also be used.

In the simultaneous saccharification and fermentation process, a cellulase preparation and the recombinant microorganism are added to a medium containing a cellulosic biomass (a biomass after pretreatment may be used), and the recombinant yeast strain is cultured at a given temperature. Culture may be carried out at any temperature without particular limitation, and the temperature may be 25° C. to 45° C., and preferably 30° C. to 40° C. from the viewpoint of ethanol fermentation efficiency. The pH level of the culture solution is preferably 4 to 6. When conducting culture, stirring or shaking may be carried out. Alternatively, the simultaneous saccharification and fermentation process may be carried out irregularly in such a manner that saccharification is first carried out at an optimal temperature for an enzyme (40° C. to 70° C.), temperature is lowered to a given level (30° C. to 40° C.), and a yeast strain is then added thereto.

EXAMPLES

Hereafter, the present disclosure is described in greater detail with reference to the examples, although the technical scope of the present disclosure is not limited to these examples.

Example 1

In the present example, a recombinant yeast strain was prepared through introduction of a xylose isomerase gene and an acetaldehyde dehydrogenase gene of *E. coli* and disruption of the NADH dehydrogenase gene, and the acetic acid metabolizing ability of the recombinant yeast strain was evaluated.

<Production of Vectors for Gene Introduction>

(1) Plasmid for XI, XKS1, TKL1, TAL1, RKI1, and RPE1 Gene Introduction and for GRE3 Gene Disruption A plasmid (pUC-5U_GRE3-P_HOR7-TKL1-TAL1-FBA1_P-P_ADH1-RPE1-RKI1-TEF1_P-P_TDH1-XI_N337C-T_DIT1-P_TDH3-XKS1-T_HIS3-LoxP-G418-LoxP-3U_GRE3) was prepared. This plasmid comprises, at the GRE3 gene locus, a sequence necessary for disruption of the GRE3 gene and introduction of the following genes into yeast: a mutant gene with an improved xylose assimilation speed resulting from substitution of asparagine with threonine at amino acid 377 of the xylose isomerase gene derived from the intestinal protozoa of *Reticulitermes speratus* (see XI_N377C; WO 2014/156194), a yeast-derived xylulokinase (XKS1) gene, the transketolase1 (TKL1) gene of the pentose phosphate pathway, the transaldolase1 (TAL1) gene, the ribulose-phosphate-epimerase 1 (RPE1) gene, and the ribose-phosphate ketoisomerase (RKI1) gene.

This plasmid was constructed to comprise: the TKL1 gene derived from the *Saccharomyces cerevisiae* BY4742 strain in which an HOR7 promoter is added on the 5' side; the TAL1 gene in which an FBA1 promoter is added; the RKI1 gene in which an ADH1 promoter is added; the RPE1 gene in which a TEF1 promoter is added; XI_N337C in which a TDH1 promoter and a DIT1 terminator are added (prepared through the total synthesis on the basis of a sequence designed by changing codons over the entire region in accordance with the frequency of codon usage of the yeast strain); the XKS1 gene in which a TDH3 promoter and an HIS3 terminator are added; a gene sequence (5U_GRE3) of an upstream region of approximately 700 bp from the 5' terminus of the GRE3 gene and a DNA sequence (3U_GRE3) of a downstream region of approximately 800 bp from the 3' terminus of the GRE3 gene, which are regions to be integrated into the yeast genome via homologous recombination; and a gene sequence (a G418 marker) comprising the G418 gene, which is a marker. The LoxP sequences were introduced on the both sides of the marker gene, so that the marker can be removed.

In addition, each DNA sequence can be amplified via PCR using the primers listed in Table 1 below. In order to ligate DNA fragments, a desired plasmid to be obtained as a final product was prepared in the following manner. A DNA sequence was added to each primer, so that the DNA sequence would overlap with its adjacent DNA sequence by approximately 15 bp. The primers were used to amplify desired DNA fragments using, as templates, *Saccharomyces cerevisiae* BY4742 genome, DNA of the XI_N337C-synthesizing gene, and synthetic DNA of the LoxP sequence. The DNA fragments were sequentially ligated using an In-Fusion HD Cloning Kit (Takara Bio Inc.) or the like, followed by cloning into the pUC19 plasmid.

TABLE 1

| Amplified DNA fragment | Primer sequence (5'-3') | SEQ ID No: |
|---|---|---|
| 5U_GRE3 | TGGGAATATTACCGCTCGAAG | 17 |
|  | CTTTAAAAAATTTCCAATTTTCCTTTACG | 18 |
| HOR7 promoter | GGAAATTTTTTAAAGTCGCAGCCACGGGTCAAC | 19 |
|  | GTGAATTGAGTCATTTTTTATTATTAGTCTTTTTTTTTTTGACAATATC | 20 |

TABLE 1-continued

| Amplified DNA fragment | Primer sequence (5'-3') | SEQ ID No: |
|---|---|---|
| TKL1 (terminator region included) | ATGACTCAATTCACTGACATTGATAAGCTAG<br>CCTTAAATCAACGTCATATTCTTTATTGGCTTTATAC | 21<br>22 |
| TAL1 (terminator region included) | GACGTTGATTTAAGGTGGTTCCGG<br>ATGTCTGAACCAGCTCAAAAGAAAC | 23<br>24 |
| FBA1 promoter | AGCTGGTTCAGACATTTTGAATATGTATTACTTGGTTATGGTTATATATGAC<br>ACTGGTAGAGAGCGACTTTGTATGC | 25<br>26 |
| ADH1 promoter | CAAAGTCGCTCTCTACCAGTCGCTTTCAATTCATTTGGGTG<br>TGTATATGAGATAGTTGATTGTATGC | 27<br>28 |
| RPE1 (terminator region included) | ACTATCTCATATACAATGGTCAAACCAATTATAGCTCCC<br>AAATGGATATTGATCTAGATGGCGG | 29<br>30 |
| RKI1 (terminator region included) | GATCAATATCCATTTCTTGGTGTGTCATCGGTAGTAACGCC<br>AGTTTTAATTACAAAATGGCTGCCGGTGTCCCAAA | 31<br>32 |
| TEF1 promoter | TTGTAATTAAAACTTAGATTAGATTGCTATGCTTTC<br>AGGAACAGCCGTCAAGGG | 33<br>34 |
| TDH1 promoter | TTGACGGCTGTTCCTCTTCCCTTTTACAGTGCTTC<br>TTTGTTTTGTGTGTAAATTTAGTGAAGTACTG | 35<br>36 |
| XI_N337C | TACACACAAAACAAAATGTCTCAAATTTTTAAGGATATCCC<br>AGCGCTCTTACTTTAGCGATCGCACTAGTTTATTGAAAC | 37<br>38 |
| DIT1 terminator | TAAAGTAAGAGCGCTACATTGGTCTACC<br>TAACATTCAACGCTATTACTCCGCAACGCTTTTCTG | 39<br>40 |
| TDH3 promoter | TAGCGTTGAATGTTAGCGTCAACAAC<br>TTTGTTTGTTTATGTGTGTTTATTCGAAACTAAGTTCTTGG | 41<br>42 |
| XKS1 | ACATAAACAAACAAAATGTTGTGTTCAGTAATTCAGAGACAG<br>AAATAATCGGTGTCATTAGATGAGAGTCTTTTCCAGTTC | 43<br>44 |
| HIS3 terminator | TGACACCGATTATTTAAAGCTGCAG<br>AGAGCGCGCCTCGTTCAG | 45<br>46 |
| LoxP (linker sequence included) | AACGAGGCGCGCTCTAATTCCGCTGTATAGCTC<br>ATAATGTATGCTATACGAAGTTATAGGGAAAGATATGAGCTATAC | 47<br>48 |
| CYC1 promoter | TATAGCATACATTATACGAAGTTATACGACATCGTCGAATATG<br>TATTAATTTAGTGTGTGTATTTGTGTTTGTGTG | 49<br>50 |
| G418 | CACACTAAATTAATAATGAGCCATATTCAACGGG<br>TTTAGTAGACATGCATTACAACCAATTAACCAATTCTG | 51<br>52 |
| URA3 terminator | TGCATGTCTACTAAACTCACAAATTAGAGCTTCAATT<br>ATAATGTATGCTATACGAAGTTATGGGTAATAACTGATATAATTAAATTGAAGC | 53<br>54 |
| LoxP (linker sequence included) | TATAGCATACATTATACGAAGTTATTGACACCGATTATTTAAAGCTG<br>ATTTTACTGGCTGGAGTATGCTGCAGCTTTAAATAATCG | 55<br>56 |
| 3U_GRE3 | TCCAGCCAGTAAAATCCATACTCAAC<br>GTCTTTTTGCCAGCCAGTCC | 57<br>58 |
| pUC19 | CACACCTTCCCCCTTGATCCTCTAGAGTCGACC<br>GCGGTAATATTCCCAGATCCCCGGGTACCGAGCTC | 59<br>60 |

(2) Plasmid for mhpF and ADH1 Gene Introduction and ADH2 Gene Disruption

A plasmid (pUC-5U_ADH2-P_TDH3-ADH1-T_ADH1-DIT1_T-mhpF-HOR7_P-URA3-3U_ADH2) was prepared. This plasmid comprises, at the ADH2 gene locus, a sequence necessary for disruption of the ADH2 gene and for introduction of the acetaldehyde dehydrogenase gene (mhpF) derived from E. coli and the alcohol dehydrogenase 1 (ADH1) gene derived from yeast into yeast.

This plasmid was constructed to comprise: the ADH1 gene derived from the Saccharomyces cerevisiae BY4742 strain in which a TDH3 promoter is added on the 5' side; the mhpF gene in which an HOR7 promoter and a DIT1 terminator are added (NCBI Accession Number 945008, prepared through the total synthesis on the basis of a sequence designed by codons over the entire region in accordance with the frequency of codon usage of the yeast strain); a gene sequence (5U_ADH2) comprising an upstream region of approximately 700 bp from the 5' terminus of the ADH2 gene and a DNA sequence (3U_ADH2) comprising a downstream region of approximately 800 bp from the 3' terminus of the ADH2 gene, which are regions to be integrated into the yeast genome via homologous recombination; and a gene sequence (a URA3 marker) comprising the URA3 gene, which is a marker.

In addition, each DNA sequence can be amplified via PCR using the primers listed in Table 2 below. In order to ligate DNA fragments, a desired plasmid to be obtained as a final product was prepared in the following manner. A DNA sequence was added to each primer, so that the DNA sequence would overlap with its adjacent DNA sequence by approximately 15 bp. The primers were used to amplify desired DNA fragments using, as a template, *Saccharomyces cerevisiae* BY4742 genome or DNA of the mhpF-synthesizing gene. The DNA fragments were sequentially ligated using an In-Fusion HD Cloning Kit or the like, followed by cloning into the pUC19 plasmid.

TABLE 2

| Amplified DNA fragment | Primer sequence (5'-3') | SEQ ID No: |
|---|---|---|
| 5U_ADH2 | CGGTACCCGGGGATCCTATGGGACTTCCGGGAA | 61 |
| | TAACATTCAACGCTATGTGTATTACGATATAGTTAATAGTTGATAG | 62 |
| TDH3 promoter | TAGCGTTGAATGTTAGCGTCAACAAC | 63 |
| | TTTGTTTGTTTATGTGTGTTTATTCGAAACTAAGTTCTTGG | 64 |
| ADH1 (terminator region included) | ACATAAACAAACAAAATGTCTATCCCAGAAACTCAAAAAG | 65 |
| | TTGTCCTCTGAGGACATAAAATACACACCG | 66 |
| DIT1 terminator | GTCCTCAGAGGACAATTACTCCGCAACGCTTTTC | 67 |
| | GGAGAGGCCGCATAATAAAGTAAGAGCGCTACATTGG | 68 |
| mhpF | TTATGCGGCCTCTCCTGC | 69 |
| | AGACTAATAATAAAAATGTCAAAGAGAAAAGTTGCTATTATCG | 70 |
| HOR7 promoter | TTTTTATTATTAGTCTTTTTTTTTTTGACAATATCTGTATGATTTG | 71 |
| | GGAGATTACCGAATCTCGCTCGCAGCCACGGGT | 72 |
| URA3 (promoter and terminator regions included) | GATTCGGTAATCTCCGAGCAG | 73 |
| | ACATAAGAGATCCGCGGGTAATAACTGATATAATTAAATTG | 74 |
| 3U_ADH2 | GCGGATCTCTTATGTCTTTACGATTTATAGTTTTC | 75 |
| | GAGGGTTGGGCATTCATCAG | 76 |
| pUC19 | AATGCCCAACCCTCGATCCTCTAGAGTCGACC | 77 |
| | GATCCCCGGGTACCGAGC | 78 |

(3) Plasmid for adhE and ADH1 Gene Introduction and ADH2 Gene Disruption

A plasmid (pUC-5U_ADH2-P_TDH3-ADH1-T_ADH1-DIT1 T-adhE-HOR7_P-URA3-3U_ADH2) was prepared. This plasmid comprises, at the ADH2 gene locus, a sequence necessary for disruption of the ADH2 gene and for introduction of the *E. coli*-derived acetaldehyde dehydrogenase gene (adhE) and the yeast-derived alcohol dehydrogenase 1 (ADH1) gene into yeast.

This plasmid was constructed to comprise: the ADH1 gene derived from the *Saccharomyces cerevisiae* BY4742 strain in which a TDH3 promoter is added on the 5' side; the adhE gene in which an HOR7 promoter and a DIT1 terminator are added (NCBI Accession Number 945837, prepared through the total synthesis on the basis of a sequence designed by changing codons over the entire region in accordance with the frequency of codon usage of the yeast strain), a gene sequence (5U_ADH2) comprising an upstream region of approximately 700 bp from the 5' terminus of the ADH2 gene and a DNA sequence (3U_ADH2) comprising a downstream region of approximately 800 bp from the 3' terminus of the ADH2 gene, which are regions to be integrated into the yeast genome via homologous recombination; and a gene sequence (a URA3 marker) comprising the URA3 gene, which is a marker.

In addition, each DNA sequence can be amplified via PCR using the primers listed in Table 3 below. In order to ligate DNA fragments, a desired plasmid to be obtained as a final product was prepared in the following manner. A DNA sequence was added to each primer, so that the DNA sequence would overlap with its adjacent DNA sequence by approximately 15 bp. The primers were used to amplify desired DNA fragments using, as a template, the pUC-5U_ADH2-P_TDH3-ADH1-T_ADH1-DIT1_T-mhpF-HOR7_P-URA3-3U_ADH2 plasmid or DNA of the adhE-synthesizing gene. The DNA fragments were sequentially ligated using an In-Fusion HD Cloning Kit or the like, followed by cloning into the pUC19 plasmid.

TABLE 3

| Amplified DNA fragment | Primer sequence (5'-3') | SEQ ID No: |
|---|---|---|
| Sequence other than adhE | TTTTATTATTAGTCTTTTTTTTTTTGACAATATCTG | 79 |
|  | TAAAGTAAGAGCGCTACATTGGTCTACC | 80 |
| adhE | AGCGCTCTTACTTTATTAAGCTGATTTCTTTGCTTTCTTC | 81 |
|  | AGACTAATAATAAAAATGGCAGTTACGAACGTTGCAG | 82 |

(4) Plasmid for NDE1 Gene Disruption

A plasmid (PUC19-5U_NDE1-RPL41B_T-eutE-TDH3_P-LoxP66-P_CYC1-HPH-T_URA3-CYC1_T-Crei-GAL1_P-LoxP71-3U_NDE1) was prepared. This plasmid comprises a sequence necessary for disruption of the NDE1 gene. This plasmid was constructed to comprise: a DNA sequence (5U_NDE1) comprising an upstream region of approximately 800 bp of the NDE1 gene, a DNA sequence (3U_NDE1) comprising a downstream region of approximately 1050 bp of the NDE1 gene, and the eutE gene in which a TDH3 promoter and a RPL41B terminator are added (NCBI Accession Number 946943, prepared through the total synthesis on the basis of a sequence designed by changing codons over the entire region in accordance with the frequency of codon usage of the yeast strain), which are regions to be integrated into the yeast genome via homologous recombination and for disruption of the NDE1 gene, and, as a marker, a gene sequence (an HPH marker) comprising a hygrocymin-resistant gene.

In addition, each DNA sequence can be amplified via PCR using the primers listed in Table 4 below. In order to ligate DNA fragments, a desired plasmid to be obtained as a final product was prepared in the following manner. A DNA sequence was added to each primer, so that the DNA sequence would overlap with its adjacent DNA sequence by approximately 15 bp. The primers were used to amplify desired DNA fragments using, as a template, genome DNA of the yeast OC2 strain or a plasmid containing a hygromycin-resistant gene. The DNA fragments were sequentially ligated using an In-Fusion HD Cloning Kit or the like, followed by cloning into the pUC19 plasmid.

The eutE gene encodes an aldehyde oxidoreductase derived from *E. coli*. SEQ ID NO: 15 and SEQ ID NO: 16 show the nucleotide sequence of the coding region of the eutE gene and the amino acid sequence of the aldehyde oxidoreductase encoded by the eutE gene, respectively.

TABLE 4

| Amplified DNA fragment | Primer sequence (5'-3') | SEQ ID No: |
|---|---|---|
| 5U_NDE1 | CGGTACCCGGGGATCATTTTGATGCTGATGTTGATGTATAGTAAAC | 83 |
|  | AAGATATGAGCTATACAGCGGAATTCAATCGACACACTTATAGTTCTAGCCCC | 84 |
| RPL41B | AGAGGCATAGCGGCAAACTAAG | 85 |
|  | GCGGATTGAGAGCAAATCGTTAAGT | 86 |
| eutE | TTGCTCTCAATCCGCCTAAACAATTCTGAATGCATCGAC | 87 |
|  | ACATAAACAAACAAAATGAACCAACAAGACATAGAACAAG | 88 |
| TDH3P | TTTGTTTGTTTATGTGTGTTTATTCGAAACTAAGTTCTTGGTGTTTTAAAACTAA | 89 |
|  | TAGCGTTGAATGTTAGCGTCAACAAC | 90 |
| Hygromycin resistance marker | AATTCCGCTGTATAGCTCATATCTTTC | 91 |
|  | GTATGCTGCAGCTTTAAATAATCGG | 92 |
| 3U_NDE1 | AAAGCTGCAGCATACGCAGAGGCCTTGTCCCTTTTTTATG | 93 |
|  | CGACTCTAGAGGATCCAGTCGAGGCATGAAGTGGAAG | 94 |
| pUC19 | GATCCTCTAGAGTCGACCTGCAGGC | 95 |
|  | GATCCCCGGGTACCGAGC | 96 |

(5) Fragment for URA3 Gene Introduction

A wild-type URA3 gene fragment used for reversion of a non-functioning URA3 gene at the URA3 gene locus back to the wild-type gene via homologous recombination was amplified from the OC2 strain. This DNA fragment can be amplified via PCR using the primers listed in Table 5 below.

TABLE 5

| Amplified DNA fragment | Primer sequence (5'-3') | SEQ ID No: |
|---|---|---|
| | AGGCTACTGCGCCAATTGAT | 97 |
| | TGCCCTACACGTTCGCTATG | 98 |

(6) Plasmid for Cre Gene Expression

The pYES-Cre plasmid to allow expression of multiple copies of the Cre gene was prepared. This plasmid was constructed by introducing the Cre gene (NCBI Accession Number NP_415757.1, prepared through the total synthesis on the basis of a sequence designed by changing codons over the entire region in accordance with the frequency of codon usage of the yeast strain) fused to the GAL1 promoter, which is induced by galactose, into pYES6/CT (Life Technologies).

Each DNA sequence necessary for plasmid construction can be amplified using the primers listed in Table 6 below. In order to ligate DNA fragments, a desired plasmid to be obtained as a final product was prepared in the following manner. A DNA sequence was added to each primer, so that the DNA sequence would overlap with its adjacent DNA sequence by approximately 15 bp. The primers were used to amplify desired DNA fragments using, as a template, the YES6/CT plasmid or DNA of the Cre-synthesizing gene. The DNA fragments were ligated using an In-Fusion HD Cloning Kit or the like.

TABLE 6

| Amplified DNA fragment | Primer sequence (5'-3') | SEQ ID No: |
|---|---|---|
| pYES6/CT | GGTTTTTTCTCCTTGACGTTAAAGTATAG | 99 |
| | TTAGTTATGTCACGCTTACATTCACG | 100 |
| Cre | ATGTCTAACTTGTTGACTGTTC | 101 |
| | TCAATCACCATCTTCCAACAATC | 102 |

<Production of Yeast Strains Comprising Vectors Introduced Thereinto>

The diploid yeast strains, *Saccharomyces cerevisiae* OC2-T (NBRC2260), were selected in a 5-fluoroorotic acid-supplemented medium (Boeke, J. D., et al., 1987, Methods Enzymol., 154: 164-75), and uracil auxotrophic strains (OC2U) were designated as host strains. Yeast strains were transformed using the Frozen-EZ Yeast Transformation II (ZYMO RESEARCH) in accordance with the protocols included therein.

A homologous recombination region of the plasmid prepared in (1) above (pUC-5U_GRE3-P_HOR7-TKL1-TAL1-FBA1_P-P_ADH1-RPE1-RKI1-TEF1_P-P_TDH1-XI_N337C-T_DIT1-P_TDH3-XKS1-T_HIS3-LoxP-G418-LoxP-3U_GRE3) was amplified via PCR, the OC2U strains were transformed using the resulting fragment, the resulting transformants were applied to a G418-containing YPD agar medium, and the grown colonies were then subjected to acclimatization. The acclimatized elite strain was designated as the Uz1252 strain. This strain was applied to a sporulation medium (1% potassium phosphate, 0.1% yeast extract, 0.05% glucose, and 2% agar) for sporulation, and a diploid of the strain was formed by utilizing homothallism. The strain in which the mutant XI, TKL1, TAL1, RPE1, RKI1, and XKS1 genes had been incorporated into the GRE3 gene locus of a diploid chromosome and the GRE3 gene had been disrupted was obtained. The resulting strain was designated as the Uz1252 strain. The plasmid for Cre gene expression was introduced into the Uz1252 strain, the G418 marker gene flanked by the LoxP sequences was removed via Cre/LoxP site-directed recombination, a strain from which the Cre plasmid had been removed was selected in the end, and the elite strain was designated as the Uz1252m strain.

Subsequently, fragments amplified via PCR from the homologous recombination regions of the plasmid prepared in (2) above (pUC-5U_ADH2-P_TDH3-ADH1-T_ADH1-DIT1_T-mhpF-HOR7_P-URA3-3U_ADH2) and the plasmid prepared in (3) above (pUC-5U_ADH2-P_TDH3-ADH1-T_ADH1-DIT1_T-adhE-HOR7_P-URA3-3U_ADH2) and a fragment for URA3 gene introduction directly amplified from the genome of the OC2 strain were used to transform the Uz1252m strain, the resulting strains were applied to a uracil-free SD agar medium or G418-containing YPD agar medium, and the grown colonies were subjected to acclimatization. The acclimatized elite strains were designated as the Uz1298 strain and the Uz1317 strain.

Heterozygous recombination (1 copy) was observed in the above strains. Sporulation was induced in a sporulation medium for the Uz1298 strain and the Uz1317 strain. The strains obtained through diploid formation by utilizing homothallism were designated as the Uz1319 strain and the Uz1318 strain, respectively.

Subsequently, a fragment amplified via PCR from the homologous recombination region of the plasmid prepared in (4) above (UC19-5U_NDE1-RPL41B_T-eutE-TDH3_P-LoxP66-P_CYC1-HPH-T_URA3-CYC1_T-Crei-GAL1_P-LoxP71-3U_NDE1) was used to transform the Uz1252m strain, the Uz1318 strain, and the Uz1319 strain, the resulting strains were applied to a hygromycin-containing YPD agar medium, and the grown colonies were subjected to acclimatization. The acclimatized elite strains were designated as the Uz2452 strain, the Uz2454 strain, and the Uz2456 strain, respectively. Sporulation was induced in a sporulation medium for the Uz2452, Uz2454, and Uz2456 strains, respectively. The strains obtained through diploid formation by utilizing homothallism were designated as the Uz2452dS strain, the Uz2454dS strain, and the Uz2456dS strain, respectively.

The genotypes of the strains produced in the examples are summarized in Table 7.

TABLE 7

| Strain | | | Genotype |
|---|---|---|---|
| Uz1252m | | | gre3:: XI_N337C XKS1 TKL1 TAL1 RKI1 RPE1 |
| Uz1319 | | adh2:: mhpF ADH1 | gre3:: XI_N337C XKS1 TKL1 TAL1 RKI1 RPE1 |
| Uz1318 | | adh2:: adhE ADH1 | gre3:: XI_N337C XKS1 TKL1 TAL1 RKI1 RPE1 |
| Uz2452 | nde1::NDE1/eutE | | gre3:: XI_N337C XKS1 TKL1 TAL1 RKI1 RPE1 |
| Uz2454 | nde1::NDE1/eutE | adh2:: adhE ADH1 | gre3:: XI_N337C XKS1 TKL1 TAL1 RKI1 RPE1 |

TABLE 7-continued

| Strain | Genotype | | |
|---|---|---|---|
| Uz2456 | nde1::NDE1/eutE | adh2:: mhpF ADH1 | gre3:: XI_N337C XKS1 TKL1 TAL1 RKI1 RPE1 |
| Uz2452dS | nde1::eutE | | gre3:: XI_N337C XKS1 TKL1 TAL1 RKI1 RPE1 |
| Uz2454dS | nde1::eutE | adh2:: adhE ADH1 | gre3:: XI_N337C XKS1 TKL1 TAL1 RKI1 RPE1 |
| Uz2456dS | nde1::eutE | adh2:: mhpF ADH1 | gre3:: XI_N337C XKS1 TKL1 TAL1 RKI1 RPE1 |

<Fermentation Test>

From among the strains obtained in the manner described above, strains exhibiting high fermentation ability were selected and subjected to a fermentation test in flasks in the manner described below. The test strains were inoculated into 100-ml baffled flasks each comprising 20 ml of YPD liquid medium (yeast extract concentration: 10 g/l; peptone concentration: 20 g/l; and glucose concentration: 20 g/l), and culture was conducted at 30° C. and 120 rpm for 24 hours. The strains were harvested and inoculated into 10-ml flasks each comprising 8 ml of a medium for ethanol production (glucose concentration: 46 g/l; xylose concentration: 40 g/l; yeast extract concentration: 10 g/l; peptone concentration: 20 g/l; and acetic acid concentration: 3.0 g/l) (concentration: 0.3 g dry cells/l), and the fermentation test was carried out via agitation culture (80 rpm; an amplitude: 35 mm; 30° C.) while adjusting a temperature at 31° C. or 34° C. A rubber stopper into which a needle (i.d.: 1.5 mm) has been inserted was used to cap each flask, and a check valve was mounted on the tip of the needle to maintain the anaerobic conditions in the flask.

Ethanol and acetic acid in the fermentation liquor were assayed via HPLC (LC-10A; Shimadzu Corporation) under the conditions described below.

Column: Aminex HPX-87H

Mobile phase: 0.01N $H_2SO_4$

Flow rate: 0.6 ml/min

Temperature: 30° C.

Detection apparatus: Differential refractometer (RID-10A)

<Results of Fermentation Test>

The results of fermentation test are shown in Table 8 and FIG. 1.

TABLE 8

| | Acetic acid concentration (g/l) | Ethanol concentration (g/l) |
|---|---|---|
| Uz1252m control | 2.24 | 34.36 |
| Uz2452 NDE1/nde1 eutE | 1.36 | 33.11 |
| Uz2452dS nde1 eutE | 0 | 32.2 |
| Uz2454 adh2:: adhE ADH1 NDE1/nde1 eutE | 2.16 | 34.2 |
| Uz2454dS adh2::adhE ADH1 nde1 eutE | 0.02 | 34.5 |
| Uz2456 adh2::mhpF ADH1 NDE1/nde1 eutE | 2.04 | 34.3 |
| Uz2456dS adh2::mhpF ADH1 nde1 eutE | 0.03 | 34.6 |

As shown in Table 8 and FIG. 1, compared with a strain in which the NDE1 gene was not disrupted (i.e., the Uz1252m strain), acetic acid concentration in a medium was found to be much lower when the strain in which one copy of the 2 NDE1 gene copies had been heterozygously disrupted (i.e., Uz2452, Uz2454, and Uz2456 strains) and the strain in which 2 copies of the NDE1 gene had been homozygously disrupted (i.e., Uz2452dS, Uz2454dS, and Uz2456dS strains). The examples of the present disclosure demonstrate that a recombinant yeast strain modified to lower the expression level of the NADH dehydrogenase gene has an excellent ability for metabolizing and degrading acetic acid in the medium.

When the strains in which the NDE1 genes had been homozygously disrupted (i.e., Uz2452dS, Uz2454dS, and Uz2456dS strains) were used, acetic acid contained in the medium was almost completely metabolized. This demonstrates that a lowered expression level of the NADH dehydrogenase gene leads to an improved acetic acid metabolizing ability.

What is claimed is:

1. A recombinant yeast strain having xylose-metabolizing ability comprising an acetaldehyde dehydrogenase gene introduced thereinto, wherein a gene encoding NADH dehydrogenase involved in reoxidation of cytoplasmic NADH on the mitochondrial outer membrane is suppressed, and
wherein in said recombinant yeast strain, the only gene(s) that are suppressed as compared to a corresponding wild-type yeast consist of: (a) said NADH dehydrogenase; or (b) said NADH dehydrogenase and an alcohol dehydrogenase gene.

2. The recombinant yeast strain according to claim 1, wherein the gene encoding NADH dehydrogenase encodes a protein (a) or (b) below:
   (a) a protein comprising the amino acid sequence as shown in SEQ ID NO: 2 or 4; or
   (b) a protein comprising an amino acid sequence exhibiting 70% or higher identity with the amino acid sequence as shown in SEQ ID NO: 2 or 4 and having enzymatic activity of catalyzing a reaction of converting NADH into $NAD^+$.

3. The recombinant yeast strain according to claim 1 comprising a xylose isomerase gene introduced thereinto.

4. The recombinant yeast strain according to claim 3, wherein the xylose isomerase gene encodes a protein (a) or (b) below:
   (a) a protein comprising the amino acid sequence as shown in SEQ ID NO: 6; or
   (b) a protein comprising an amino acid sequence exhibiting 70% or higher identity with the amino acid sequence as shown in SEQ ID NO: 6 and having enzymatic activity of converting xylose into xylulose.

5. The recombinant yeast strain according to claim 1, which further comprises a xylulokinase gene introduced thereinto.

6. The recombinant yeast strain according to claim 1, which comprises a gene encoding an enzyme selected from a group of enzymes constituting a non-oxidative process in the pentose phosphate pathway introduced thereinto.

7. The recombinant yeast strain according to claim 6, wherein the group of enzymes constituting a non-oxidative process in the pentose phosphate pathway includes ribose-5-phosphate isomerase, ribulose-5-phosphate-3-epimerase, transketolase, and transaldolase.

8. The recombinant yeast strain according to claim 1, in which an alcohol dehydrogenase gene having activity of converting acetaldehyde into ethanol is introduced.

9. The recombinant yeast strain according to claim 1, wherein said alcohol dehydrogenase gene is disrupted.

10. A method for producing ethanol comprising a step of culturing the recombinant yeast strain according to claim 1 in a xylose-containing medium to perform ethanol fermentation.

11. The method for producing ethanol according to claim 10, wherein the medium contains cellulose and the ethanol fermentation proceeds simultaneously with saccharification by at least a cellulase.

* * * * *